United States Patent [19]

Suzuki et al.

[11] Patent Number: 5,508,421

[45] Date of Patent: Apr. 16, 1996

[54] PYRROLOTRIAZOLE AZOMETHINE DYE, AND HEAT TRANSFER DYE PROVIDING MATERIAL CONTAINING A PYRROLOTRIAZOLE AZOMETHINE DYE

[75] Inventors: Makoto Suzuki; Hisashi Mikoshiba; Seiiti Kubodera; Osamu Takahashi; Yasuhiro Shimada; Koushin Matsuoka; Shigeru Yamazaki; Katsuyoshi Yamakawa; Kozo Sato, all of Kanagawa, Japan

[73] Assignee: Fuji Photo Film Co., Ltd., Kanagawa, Japan

[21] Appl. No.: 279,191

[22] Filed: Jul. 22, 1994

Related U.S. Application Data

[62] Division of Ser. No. 894,573, Jun. 5, 1992, Pat. No. 5,362,882.

[30] Foreign Application Priority Data

| | | | |
|---|---|---|---|
| Jun. 7, 1991 | [JP] | Japan | 3-162323 |
| Jun. 7, 1991 | [JP] | Japan | 3-162324 |
| Jun. 7, 1991 | [JP] | Japan | 3-162325 |
| Nov. 27, 1991 | [JP] | Japan | 3-311212 |
| Nov. 27, 1991 | [JP] | Japan | 3-335861 |
| Feb. 21, 1992 | [JP] | Japan | 4-069980 |

[51] Int. Cl.$^6$ .......................... C07D 487/04; G03C 7/38; G03C 7/36

[52] U.S. Cl. ...................... 548/262.4; 430/337; 430/372; 430/376; 430/381; 430/385; 430/386; 430/387; 430/428; 430/429; 430/463; 430/542; 430/551; 430/554; 430/558; 430/559; 430/546

[58] Field of Search .................. 548/262.4; 430/372, 430/376, 381, 385, 546; 534/728

[56] References Cited

U.S. PATENT DOCUMENTS

| | | | |
|---|---|---|---|
| 3,705,896 | 12/1972 | Bailey | 548/262.4 |
| 4,093,728 | 6/1978 | Wade et al. | 548/262.4 X |
| 4,910,127 | 3/1990 | Sasaki et al. | 430/546 |
| 4,921,968 | 5/1990 | Yokoyama et al. | 548/262.4 |
| 4,925,481 | 5/1990 | Blume et al. | 548/262.4 X |
| 5,118,812 | 6/1992 | Yokoyama et al. | 548/262.4 |
| 5,122,611 | 6/1992 | Tanaka et al. | 548/262.4 |
| 5,362,882 | 11/1994 | Suzuki et al. | 548/262.4 |

FOREIGN PATENT DOCUMENTS

| | | | |
|---|---|---|---|
| 0252288 | 1/1988 | European Pat. Off. | 430/546 |
| 60-186567 | 9/1985 | Japan | 548/262.4 |
| 1-261738 | 11/1986 | Japan | 548/262.4 |
| 62-279340 | 12/1987 | Japan . | |
| 62-278552 | 12/1987 | Japan | 548/262.4 |
| 2-115183 | 4/1990 | Japan | 548/262.4 |
| 4-359968 | 12/1992 | Japan | 548/262.4 |
| 4-359967 | 12/1992 | Japan | 548/262.4 |
| 811765 | 4/1959 | United Kingdom | 548/262.4 |

OTHER PUBLICATIONS

Patent Abstracts of Japan, vol. 12, No. 180 (P-709) published May 27, 1988 for JP-A-62-289837 published Dec. 16, 1987, Konica.

"Electrophilic Substitution Reactions in the 1N–Pyrrolo(1, 2–b)S–Triazole Series", Ukrainskii Khimicheskii Zhurnal, vol. 41, No. 2, pp. 181–185 (1975), Babichev et al.

"π–Electron Structure and Reactivities of Isomeric Pyrrolo-–sym–Triazoles", Khimiya Geterotsiklicheskikh Soedinenii, No. 2, pp. 261–267, Feb. 1974. Savranskii et al.

"Absorption Characteristics of Pyrazoloazole-Based Magenta Azomethine Dyes", Preprint of Annual Meeting of SPSTJ '85, A–24, pp. 108–110 (May 23–24, 1985).

Abstract of JP–A–3–114891 published May 16, 1991.

Primary Examiner—Floyd D. Higel
Attorney, Agent, or Firm—Sughrue, Mion, Zinn, Macpeak & Seas

[57] ABSTRACT

A pyrrolotriazole azomethine dye represented by formula (I), (II) or (IV) is disclosed:

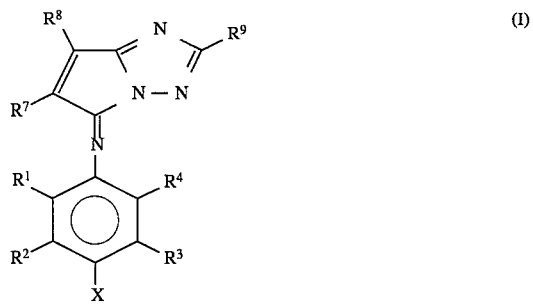

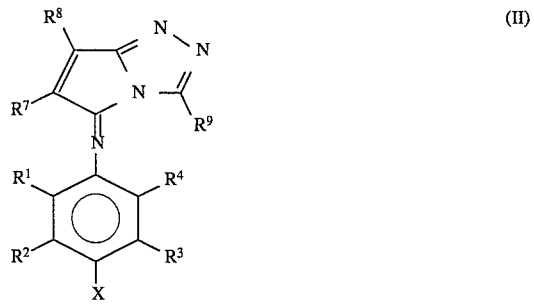

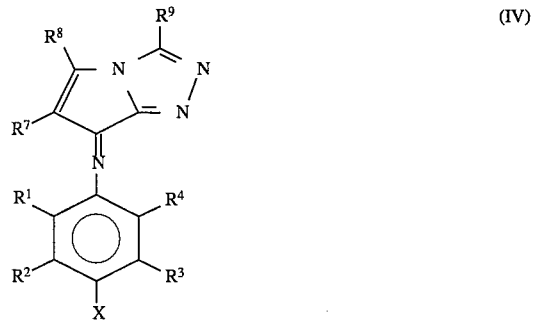

Also, a heat transfer dye providing material is disclosed, in which the material includes a support having thereon a dye providing layer containing a heat migrating dye, with the dye providing layer containing at least one pyrrolotriazole azomethine dye represented by any of the above formulae (I), (II) and (IV).

9 Claims, 2 Drawing Sheets

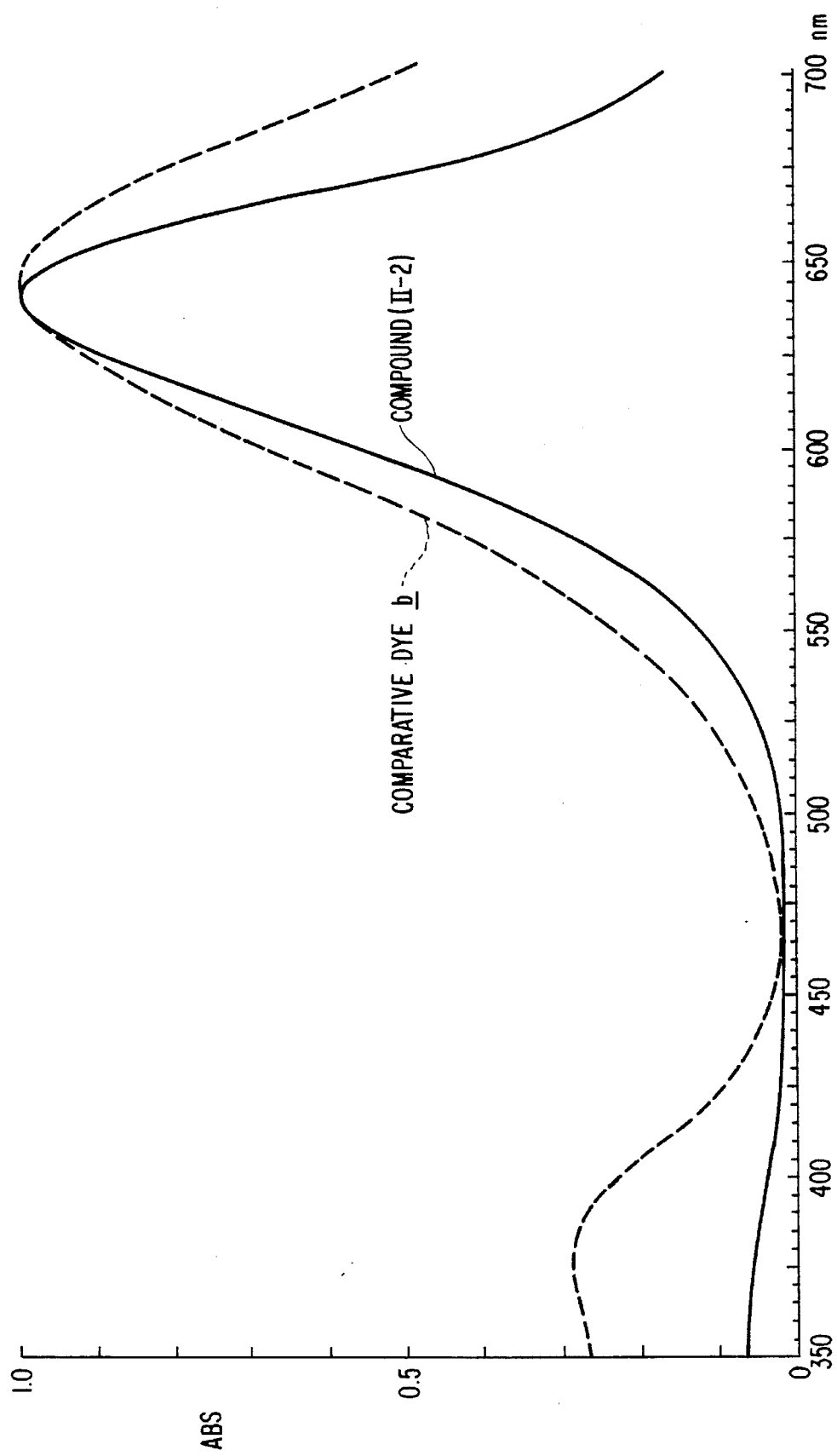

PYRROLOTRIAZOLE AZOMETHINE DYE, AND HEAT TRANSFER DYE PROVIDING MATERIAL CONTAINING A PYRROLOTRIAZOLE AZOMETHINE DYE

This is a divisional of application No. 07/894,573 filed Jun. 5, 1992, now issued as U.S. Pat. No. 5,362,882.

FIELD OF THE INVENTION

The present invention relates to a novel pyrrolotriazole derivative, a pyrrolotriazole azomethine dye, and also to a heat transfer dye providing material containing a pyrrolotriazole azomethine dye.

BACKGROUND OF THE INVENTION

1H-Pyrrolo-[1,2-b][1,2,4]triazole derivaties are useful as synthesis intermediates of physiologically active substances such as pharmaceutical preparations and pesticides. These derivatives are also known as coupler nuclei and dyes which exhibit reduced secondary absorption in the field of photographic chemistry (proceedings of the 60th Annual Conference of The Society of Photographic Science and Technology of Japan). However, 1H-pyrrolo-[1,2-b][1,2,4]triazole dyes which have heretofore been known exhibit a maximum absorption wavelength of lower than 560 nm. No 1H-pyrrolo-[1,2-b][1,2,4]triazole dyes which exhibit a maximum absorption wavelength of higher than 600 nm have been known.

In recent years, 1H-pyrrolo-[1,2-b][1,2,4]triazole dyes which exhibit a maximum absorption wavelength of higher than 560 nm, particularly 600 nm have been desired. In other words, dyes containing a 1H-pyrrolo-[1,2-b][1,2,4]triazole nucleus which exhibit reduced secondary absorption and a primary absorption wavelength of higher than 600 nm have been keenly desired.

Furthermore, in recent years, new color image formation methods such as color electrophotography, ink jet printing process and heat-sensitive transfer process have been proposed. On the other hand, with the development of electronic imaging technique, the demand for solid state image pick-up tube and filter for color liquid crystal television set has increased. Thus, azomethine dyes have been applied and reviewed in color photography as well as various systems or merchandise.

As cyan azomethine dyes in these applications there have been known phenol and naphthol azomethine dyes. Furthermore, imidazole azomethine dyes and hydroxypyridine azomethine dyes have been known.

Moreover, pyrazoloazole azomethine dyes, pyrazolopyrimidin-5-one azomethine dyes, pyrazoloquinazolone azomethine dyes, pyrazolotriazine azomethine dyes and cyan azomethine dyes have been known.

However, these known azomethine dyes have various disadvantages. For example, phenol and naphthol azomethine dyes exhibit too broad an absorption to serve as dyes for filter. Further, imidazole azomethine dyes are disadvantageous in that they exhibit a low fastness to light. Moreover, pyrazolopyrimidin-5-one azomethine dyes, pyrazoloquinazolone azomethine dyes and pyrazolotriazine azomethine dyes exhibit too broad an absorption. Further, pyrazolotriazole azomethine dyes exhibit a low fastness to light. Moreover, hydroxypyridine azomethine dyes can hardly be synthesized and exhibit a low fastness to light.

Thus, among known azomethine dyes, there are no dyes which exhibit an absorption waveform suitable for cyan color and a high fastness to light and heat. Therefore, the development of azomethine dyes which exhibit a sharp absorption and a high fastness has been keenly desired.

In order to overcome these difficulties, the inventors made a study on novel azomethine dyes. As a result, it was found that pyrrolotriazole azomethine dyes having a specific structure which has never been known exhibit a sharp absorption and a high fastness to light. Thus, the present invention was worked out.

Pyrrolotriazole couplers are disclosed in JP-A-62-279340 and 62-278552 (the term "JP-A" as used herein means an "unexamined published Japanese patent application").

Even if the foregoing techniques are known, the present invention is by no means limited thereby.

The above mentioned known couplers are considered to undergo color development to produce azomethine dyes. According to the above cited references, the color of the dyes thus produced are magenta.

The inventors' study showed that pyrrolotriazole azomethine dyes represented by formulae (I) to (IV) given later exhibit a cyan color when its coupler portion is such that Hammett's substituent constant $\sigma_p$ of $R^7$ is 0.15 or more and the sum of Hammett's substituent constant $\sigma_p$ of $R^7$ and $R^8$ is 0.65 or more.

In the above cited references, there is no reference to couplers which will give an azomethine dye that exhibits a cyan color. There is neither reference that gives an expectation of a specific structure that exhibits a cyan color.

In other words, it was disclosed for the first time by the inventors, who made a study on the relationship between the substituents $R^7$ and $R^8$ and the absorption characteristics of dye, that novel pyrrolotriazole azomethine dyes of the present invention exhibit an excellent cyan color. It is extremely difficult to expect this fact from the above cited references.

Moreover, in recent years, with the rapid progress of the communication industry, various data processing systems have been developed, and recording processes and apparatus suitable for these data processing systems have been developed and applied. Among these recording processes, the heat transfer recording process can be operated by means of a light weight and compact apparatus which gives no noise and excellent handleability and maintenance. The heat transfer recording process can also be operated in a color system. Thus, the heat transfer recording process has been widely employed in recent years.

Examples of the heat transfer recording process include a process which comprises heating a heat transfer dye providing material comprising a hot-melt ink layer carried on a support by a thermal head to melt the ink which is then transferred to an image-receiving material (melt transfer process), and a process which comprises heating a heat transfer dye providing material comprising a dye providing layer containing a heat migrating dye and a binder by a heat head to allow the heat migration of the dye alone to an image-receiving layer in an image-receiving material to effect recording (heat migration process, generally referred also to as "sublimation type heat-sensitive transfer process").

The present invention relates to a heat transfer dye providing material for use in the heat migration process. The term "heat migrating dye" as used herein means a dye which can undergo sublimation or diffusion in a medium to effect transfer from a heat transfer dye providing material to a heat transfer image-receiving material.

However, heat migrating dyes for use in this process have heretofore encountered various limitations. There is little heat migrating dye which fully satisfies necessary properties. Examples of such necessary properties include spectral characteristics suitable for color reproduction, ease of heat migration, insusceptiblity to discoloration due to heat and light, reduced denaturation by various chemicals, insusceptibility to sharpness drop after image formation, insusceptibility to re-transfer of image, and ease of preparation of heat transfer dye providing material.

Particularly important among these properties is insusceptiblity to discoloration due to heat and light. However, heat migrating dyes which have heretofore been used leave much to be desired in this respect and thus can be subject to discoloration in a slight period of time. Therefore, these heat migrating dyes have been improved from the standpoint of image preservability. Further, most of these known dyes exhibit a broad absorption. Thus, the development of dyes which exhibit a sharp absorption has been desired.

SUMMARY OF THE INVENTION

It is therefore an object of the present invention to provide a novel pyrrolotriazole derivative.

It is another object of the present invention to provide a pyrrolotriazole azomethine dye which exhibits a sharp absorption and a high fastness to heat and light.

It is a further object of the present invention to provide a heat transfer dye providing material which gives a highly color-reproduced image having a high fastness to heat and light.

These and other objects of the present invention will become more apparent from the following detailed description and examples.

These objects of the present invention are accomplished with pyrrolotriazole derivatives represented by formulae (I) to (V):

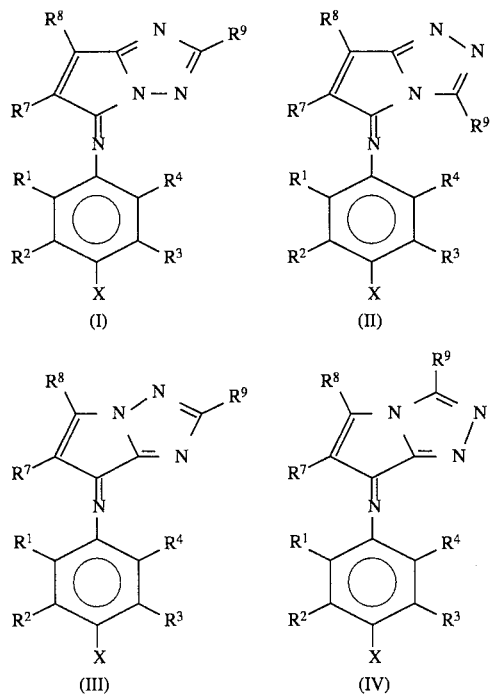

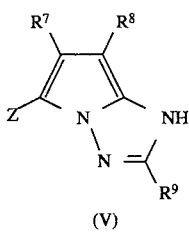

In the above formulae (I) to (V), $R^1$, $R^2$, $R^3$ and $R^4$ each independently represents a hydrogen atom or nonmetallic atomic group.

X represents —OH or —$NR^5R^6$.

$R^5$ and $R^6$ each independently represents a hydrogen atom, alkyl group, aryl group or heterocyclic group.

$R^7$ represents an electrophilic group having a Hammett's substituent constant $\sigma_p$ of 0.15 or more.

$R^8$ and $R^9$ each independently represents a hydrogen atom or nonmetallic atomic group.

The sum of Hammett's substituent constant $\sigma_p$ of $R^7$ and $R^8$ is 0.65 or more.

$R^1$ and $R^2$, and/or $R^2$ and $R^5$, and/or $R^5$ and $R^6$, and/or $R^6$ and $R^3$, and/or $R^3$ and $R^4$ may be connected to each other to form a cyclic structure.

$R^7$ and $R^8$ may be connected to each other to form a cyclic structure.

Z represents a hydrogen atom, halogen atom, arylthio group, heterocyclic thio group, arylsulfinyl group or nitroso group.

BRIEF DESCRIPTION OF THE DRAWINGS

FIG. 1 shows the absorption spectrum of ethyl acetate solution of an exemplary compound (I-2) and a comparative dye a; and FIG. 2 shows the absorption spectrum of ethyl acetate solution of an exemplary compound (II-2) and a comparative dye b.

DETAILED DESCRIPTION OF THE INVENTION

Figure 1:
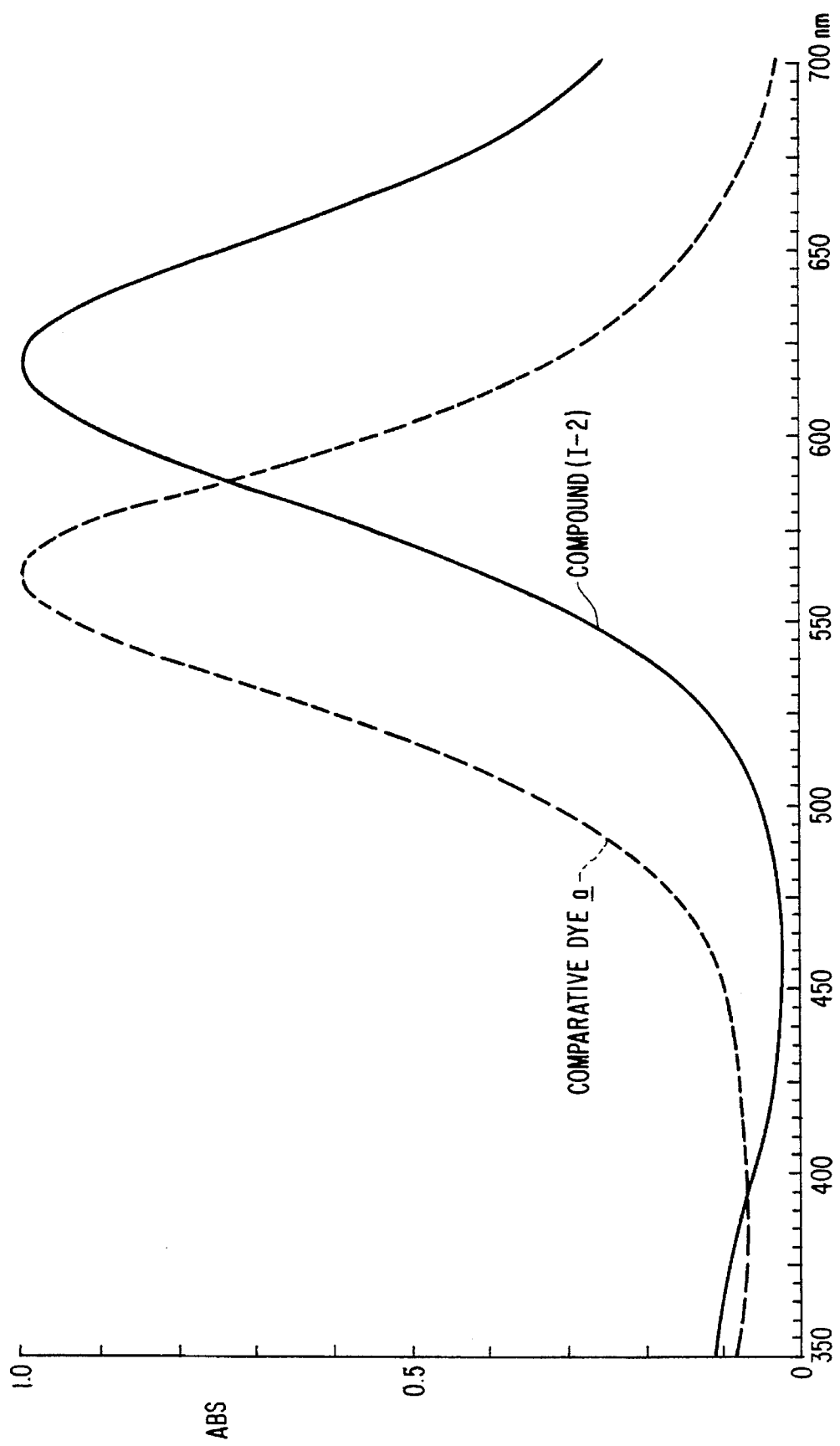

Among the compounds represented by formulae (I) to (V), those represented by formulae (I) to (IV) are useful as cyan dyes. A heat transfer dye providing material comprising a dye providing layer containing a heat migrating dye provided on a support can provide an image having excellent absorption characteristics and a high fastness to heat and light if these compounds are incorporated in the dye providing layer.

Further, the 1H-pyrrolo-[1,2-b][1,2,4]triazole derivatives represented by formula (V) are useful as synthesis intermediates of the compounds represented by formulae (I) to (IV), or physiologically active substances such as pharmaceutical preparations and pesticides.

Formulae (I) to (V) will be further described hereinafter.

Hammett's substituent constant as used herein will be now briefly discussed. Hammett's rule is an empirical law which was proposed in 1935 by L. P. Hammett to give a quantative discussion of the effect of substituents on the reaction or equilibrium of benzene derivatives. This rule is now widely considered reasonable. Substituent constants determined by Hammett's rule include $\sigma_p$ value and $\sigma_m$ value which can be found in many general references, e.g., J. A. Dean, *Lange's Handbook of Chemistry*, vol. 12, 1979 (McGraw-Hill), and *Kagaku No Ryoiki* (The Domain of Chemistry), extra edition, No. 122, pp. 96–103, 1979 (Nankodo). In the present invention, various substituents are limited or illustrated by Hammett's substituent constant $\sigma_p$. However, this doesn't mean that these substituents are limited to those having known $\sigma_p$ values found in the above cited references. It goes without saying that even when these substituents exhibit $\sigma_p$ values unknown in any reference, they are included in those having $\sigma_p$ values that would be included in the range known in these references when measured according to Hammett's rule. The value of $\sigma_p$ will be hereinafter defined in this manner.

$R^1$, $R^2$, $R^3$ and $R^4$ each independently represents a hydrogen atom or nonmetallic atomic group. Examples of the nometallic atomic group include halogen atom, alkyl group, aryl group, heterocyclic group, cyano group, hydroxyl group, nitro group, carboxyl group, sulfonic acid group, amino group (including substituted amino group), alkoxy group, aryloxy group, acylamino group, aminocarbonylamino group, sulfamoylamino group, alkylthio group, arylthio group, alkoxycarbonylamino group, sulfonylamino group, carbamoyl group, sulfamoyl group, sulfonyl group, alkoxycarbonyl group, heterocyclic oxy group, azo group, acyloxy group, carbamoyloxy group, silyloxy group, aryloxycarbonyl group, imido group, heterocyclic thio group, sulfinyl group, phosphoryl group, formyl group, acyl group, and azolyl group. Of these nonmetallic atomic groups, those which can contain substituents may be substituted by substituents such as halogen atom, hydroxyl group, carboxyl group, sulfo group, cyano group, nitro group, amino group, alkyl group, alkenyl group, alkynyl group, aryl group, alkoxy group, aryloxy group, alkylthio group, arylthio group, alkylsulfonyl group, arylsulfonyl group, acyl group, acyloxy group, alkoxycarbonyl group, aryloxycarbonyl group, carbonamido group, sulfonamido group, carbamoyl group, sulfamoyl group, ureido group, alkoxycarbonylamino group, sulfamoylamino group, alkoxysulfonyl group, imido group and heterocyclic group (these substituents will be hereinafter referred to as "substituent group A").

Specific examples of $R^1$, $R^2$, $R^3$ and $R^4$ include hydrogen atom, alkyl group (preferably alkyl group having a total carbon atom number of from 1 to 30 (hereinafter expressed as alkyl group), e.g., methyl, ethyl, propyl, butyl), alkoxy group (preferably $C_{1-30}$ alkoxy group, e.g., methoxy, ethoxy, methoxyethoxy, isopropoxy), halogen atom (e.g., bromine, fluorine, chlorine), acylamino group (preferably $C_{1-30}$ alkylcarbonylamino group, e.g., formylamino, acetylamino, propionylamino, cyanoacetylamino, or preferably $C_{7-30}$ arylcarbonylamino group, e.g., benzoylamino, p-toluylamino, pentafluorobenzoylamino, m-methoxybenzoylamino), alkoxycarbonyl group (preferably $C_{2-30}$ alkoxycarbonyl group, e.g., methoxycarbonyl, ethoxycarbonyl), cyano group, sulfonylamino group (preferably $C_{2-30}$ sulfonylamino group, e.g., methanesulfonylethanesulfonylamino, N-methylmethanesulfonylamino), amino, carbamoyl group (preferably $C_{2-30}$ carbamoyl group, e.g., methylcarbamoyl, dimethylcarbamoyl, butylcarbamoyl, isopropylcarbamoyl, t-butylcarbamoyl, cyclopentylcarbamoyl, cyclohexylcarbamoyl, methoxyethylcarbamoyl, chloroethylcarbamoyl, cyanoethylcarbamoyl, ethylcyanoethylcarbamoyl, benzylcarbamoyl, ethoxycarbonylmethylcarbamoyl, furfurylcarbamoyl, tetrahydrofurfurylcarbamoyl, phenoxymethylcarbamoyl, allylcarbamoyl, crotylcarbamoyl, prenylcarbamoyl, 2,3-dimethyl-2-butenylcarbamoyl, homoallylcarbamoyl, homocrotylcarbamoyl, homoprenylcarbamoyl, preferably $C_{7-30}$ arylcarbamoyl group, e.g., phenylcarbamoyl, p-toluylcarbamoyl, m-methoxyphenylcarbamoyl, 4,5-dichlorophenylcarbamoyl, p-cyanophenylcarbamoyl, p-acetylaminophenylcarbamoyl, p-methoxycarbonylphenylcarbamoyl, m-trifluoromethylphenylcarbamoyl, o-fluorophenylcarbamoyl, 1-naphthylcarbamoyl, or preferably $C_{4-30}$ heterylcarbamoyl group, e.g., 2-pyridylcarbamoyl, 3-pyridylcarbamoyl, 4-pyridylcarbamoyl, 2-thiazolylcarbamoyl, 2-benzthiazolylcarbamoyl, 2-benzimidazolylcarbamoyl, 2-(4-methylphenyl)-1,3,4-thiazolylcarbamoyl), sulfamoyl group (preferably $C_{0-30}$ sulfamoyl group, e.g., methylsulfamoyl, dimethylsulfamoyl), aminocarbonylamino group (preferably $C_{1-30}$ aminocarbonylamino group, e.g., methylaminocarbonylamino, dimethylaminocarbonylamino), alkoxycarbonylamino group (preferably $C_{2-30}$ alkoxycarbonylamino group, e.g., methoxycarbonylamino, ethoxycarbonylamino), hydroxyl group, carboxyl group (including salts thereof), sulfonic acid group (including salts thereof), amino group (preferably $C_{0-30}$ amino group, e.g., amino, methylamino, dimethylamino, anilino), aryl group (preferably $C_{6-30}$ aryl group, e.g., phenyl, macetylphenyl, p-methoxyphenyl), heterocyclic group (preferably $C_{3-30}$ heterocyclic group, e.g., 2-pyridyl, 2-furyl, 2-tetrahydrofuryl), nitro group, aryloxy group (preferably $C_{6-30}$ aryloxy group, e.g., phenoxy, p-methoxyphenoxy, o-chlorophenoxy), sulfamoylamino group (preferably $C_{0-30}$ sulfamoylamino group, e.g., methylsulfamoyl, dimethylsulfamoyl), alkylthio group (preferably $C_{1-30}$ alkylthio group, e.g., methylthio, ethylthio), arylthio group (preferably $C_{6-30}$ arylthio group, e.g., phenylthio, p-methoxyphenylthio, o-chlorophenylthio), sulfonyl group (preferably $C_{3-30}$ sulfonyl group, e.g., methanesulfonyl, p-toluenesulfonyl), formyl group, acyl group (preferably $C_{1-30}$ acyl group, e.g., acetyl, benzoyl, p-toluyl), heterocyclic oxy group (preferably $C_{1-30}$ heterocyclic oxy group), azo group (preferably $C_{3-30}$ azo group, e.g., p-nitrophenylazo), acyloxy group (preferably $C_{1-30}$ acyloxy group, e.g., acetyloxy, benzoyloxy), carbamoyloxy group (preferably $C_{1-30}$ carbamoyloxy group, e.g., methylcarbamoyloxy), silyloxy group (preferably $C_{3-30}$ silyloxy group, e.g., trimethylsilyloxy), aryloxycarbonyl group (preferably $C_{7-30}$ aryloxycarbonyl group, e.g., phenoxycarbonyl), imido group (preferably $C_{4-30}$ imido group, e.g., phthalimido), heterocyclic thio group (preferably $C_{3-30}$ heterocyclic thio group), sulfinyl group (preferably $C_{1-30}$ sulfinyl group, e.g., diethylaminosulfinyl), phsophoryl group (preferably $C_{0-30}$ phosphoryl group, e.g., diaminophosphoryl), and azolyl group (preferably $C_{2-30}$ azolyl group, e.g., 2-pyrazolyl).

Preferred among the groups represented by $R^2$, $R^3$ and $R^4$ is hydrogen atom.

Preferred among the groups represented by $R^1$ are hydrogen atom, $C_{1-30}$ alkyl group, $C_{1-30}$ alkoxy group, halogen atom (e.g., fluorine, chlorine, bromine), $C_{1-30}$ acylamino group, $C_{1-30}$ sulfonylamino group, $C_{1-30}$ aminocarbonylamino group, and $C_{2-30}$ alkoxycarbonylamino group. Particularly preferred among these groups are hydrogen atom, alkyl group, and acylamino group.

X represents —OH or —NR$^5$R$^6$.

$R^3$ and $R^6$ each independently represents a hydrogen atom, alkyl group, aryl group, or heterocyclic group. The alkyl group, aryl group, and heterocyclic group may be substituted by substituents such as substituent group A.

Specific examples of $R^5$ and $R^6$ include a hydrogen atom, alkyl group (preferably $C_{1-30}$ alkyl group, e.g., methyl, ethyl, propyl, isopropyl, butyl, octyl, 2-aminoethyl, 2-carbamoylethyl, 2-carboxyethyl, 4-sulfobutyl, 3-(4-methoxyphenoxy)propyl, 2-methanesulfonamidoethyl, 2-hydroxyethyl, 3-hydroxypropyl, 4-hydroxybutyl, 2-methoxyethyl, 3-methoxypropyl, ethoxyethyl, 2-phenylethyl, 2-cyanoethyl, cyanomethyl, 2-chloroethyl, 3-bromopropyl, 2-methoxycarbonylethyl, 3-ethoxycarbonylpropyl, 2-(N-methylaminocarbonyl)ethyl, 3-(N,N-dimethylaminocarbonyl)propyl, 2-acetylaminoethyl, 3-(ethylcarbonylamino)propyl, allyl, homoallyl, prenyl, n-dodecyl, 2-acetyloxyethyl), aryl group (preferably $C_{6-30}$ aryl group, e.g., phenyl, p-tolyl, p-methoxyphenyl, 2,4-dichlorophenyl, p-nitrophenyl, 2,4-dicyanophenyl, 2-naphthyl) or heterocyclic group (including those containing substituents, preferably $C_{3-30}$ heterocyclic group such as those represented by the following formulae).

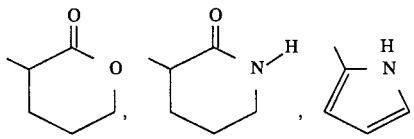

Preferred among the groups represented by $R^5$ and $R^6$ is a $C_{1-30}$ alkyl group which may be substituted (e.g., methyl, ethyl, propyl, 2-cyanoethyl, 2-acetyloxyethyl, 2-ethoxycarbonylethyl, 2-methoxyethyl, 2-methanesulfonamidoethyl, 2-hydroxyethyl, 3-hydroxypropyl, allyl, homoallyl, prenyl).

Examples of the ring which $R^5$ and $R^6$ may be connected to each other to form include those represented by the following formulae:

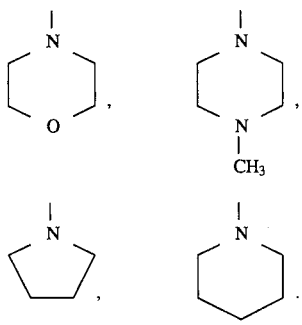

Preferred examples of the ring which $R^2$ and $R^5$, and/or $R^3$ and $R^6$, may be connected to each other to form include those represented by the following formulae:

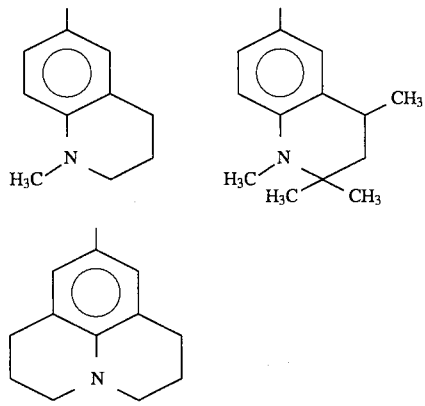

$R^7$ represents an electrophilic group having a Hammett's substituent constant $\sigma_p$ of 0.15 or more.

Examples of $R^7$ include formyl group, acyl group, acyloxy group, carbamoyl group, alkoxycarbonyl group, aryloxycarbonyl group, cyano group, carboxyl group, nitro group, dialkylphosphono group, diarylphosphono group, diarylphosphinyl group, alkylsulfinyl group, arylsulfinyl group, alkylsulfonyl group, arylsulfonyl group, arylthio group, sulfonyloxy group, acylthio group, sulfamoyl group, isocyanato group, thiocyanato group, thiocarbonyl group, alkyl group substituted by at least two halogen atoms, alkoxy group substituted by at least two halogen atoms, aryloxy group substituted by at least two halogen atoms, alkylamino group substituted by at least two halogen atoms, alkylthio group substituted by at least two halogen atoms, aryl group substituted by other electrophilic groups having a Hammett's substituent constant $\sigma_p$ of 0.15 or more, heterocyclic group, chlorine atom, bromine atom, and selenocyanato group. Of these groups, those which can contain substituents may be substituted by substituents such as substituent group A.

Specific examples of $R^7$ include acyl group (e.g., acetyl, 3-phenylpropanoyl, benzoyl, 4-dodecyloxybenzoyl), acyloxy group (e.g., acetoxy), carbamoyl group (e.g., N-ethylcarbamoyl, N,N-dibutylcarbamoyl, N-(2-dodecyloxyethyl)carbamoyl, N-methyl-N-dodecylcarbamoyl, N-[3-(2,4-di-t-amylphenoxy)propyl] carbamoyl), alkoxycarbonyl group (preferably straight-chain, branched or cyclic alkoxycarbonyl group, e.g., methoxycarbonyl, ethoxycarbonyl, isopropoxycarbonyl, isobutoxycarbonyl, n-octyloxycarbonyl, n-decyloxycarbonyl, ndodecyloxycarbonyl, n-hexadecyloxycarbonyl, 2-ethylhexyloxycarbonyl, 3,5,5-trimethylhexyloxycarbonyl, 2-ethyl-4-methylpentyloxycarbonyl, 2-hexyldecyloxycarbonyl, 2-heptylundecyloxycarbonyl, 2-octyldodecyloxycarbonyl, 2,4,6-trimethylheptyloxycarbonyl, 2,4,6,8-tetramethylnonyloxycarbonyl, benzyloxycarbonyl, 2-phenethyloxycarbonyl, 3-(t-octylphenoxy)propoxycarbonyl, 3-(2,4-di-t-pentylphenoxy)propoxycarbonyl, 2-(4-biphenyloxy)ethoxycarbonyl, 3-dodecyloxypropoxycarbonyl, 2-dodecylthioethoxycarbonyl, 9,10-epoxyoctadecyloxycarbonyl, dodecyloxycarbonylmethoxycarbonyl, 2-(2-naphthyloxy)ethoxycarbonyl, 7,7-dimethyl-2-(3',3'-dimethylbutyl)-5-methyloctyloxycarbonyl, 2-methyl-cyclohexyloxycarbonyl, 2-hexyl-cyclohexyloxycarbonyl), aryloxycarbonyl group (e.g., phenoxycarbonyl), cyano group, carboxyl group, nitro group, dialkylphosphono group (e.g., dimethylphosphono), diarylphosphono group (e.g., diphenylphosphono), diarylphosphinyl group (e.g., diphenylphosphinyl), alkylsulfinyl group (e.g., 3-phenoxypropylsulfinyl), arylsulfinyl group (e.g., 3-pentadecylphenylsulfinyl), alkylsulfonyl group (e.g., methanesulfonyl, octanesulfonyl), arylsulfonyl group (e.g., benzenesulfonyl, toluenesulfonyl), alkylthio group (e.g., methylthio, octylthio, tetradecylthio, 2-phenoxyethylthio, 3-phenoxypropylthio, 3-(4-t-butylphenoxy)propylthio), arylthio group (e.g., phenylthio, 2-butoxy-5-t-octylphenylthio, 3-pentadecylphenylthio, 2-carboxyphenylthio, 4-tetradecanamidophenylthio), sulfonyloxy group (e.g., methanesulfonyloxy, toluenesulfonyloxy), acylthio group (e.g., acetylthio, benzoylthio), sulfamoyl group (e.g., N-ethylsulfamoyl, N,N-dipropylsulfamoyl, N-(2-dodecyloxyethyl) sulfamoyl, N-ethyl-N-dodecylsulfamoyl, N, N-diethylsulfamoyl), isocyanato group, thiocyanato group, thiocarbonyl group (e.g., methylthiocarbonyl, phenylthiocarbonyl), alkyl group substituted by at least two halogen atoms (e.g., trifluoromethane, heptafluoropropane), alkoxy group substituted by at least two halogen atoms (e.g., trifluoromethyloxy), aryloxy group substituted by at least two halogen atoms (e.g., pentafluorophenyloxy), alkylamino group substituted by at least two halogen atoms (e.g., N,N-di-(trifluoromethyl)amino), alkylthio group substituted by at least two halogen atoms (e.g., difluoromethylthio, 1,1,2,2-tetrafluoroethylthio), aryl group substituted by two or more electrophilic groups having a Hammett's substituent constant $\sigma_p$ of 0.15 or more (e.g., 2,4-dinitrophenyl, 2,4,6-trichlorophenyl, pentachlorophenyl), heterocyclic group (e.g., 2-benzoxazolyl, 2-benzothiazolyl, 1-phenyl-2-benzimidazolyl, 5-chloro-1-tetrazolyl, 1-pyrrolyl), chlorine atom, bromine atom, and selenocyanato group.

Among these substituents, those which can further contain substituents may further contain halogen atoms or substituents connected via carbon atom, oxygen atom, nitrogen atom or sulfur atom thereto.

Examples of $\sigma$ values of typical electrophilic groups having a Hammett's substituent constant $\sigma_p$ of 0.15 or more include 0.66 for cyano group, 0.45 for carboxyl group, 0.78 for nitro group, 0.54 for trifluoromethyl group, 0.50 for acetyl group, 0.92 for trifluoromethanesulfonyl group, 0.72 for methanesulfonyl group, 0.70 for benzenesulfonyl group, 0.49 for methanesulfinyl group, 0.36 for carbamoyl group, 0.45 for methoxycarbonyl group, 0.44 for phenoxycarbonyl group, 0.37 for pyrazolyl group, 0.36 for methanesulfonyloxy group, 0.33 for benzenesulfonyloxy group, 0.60 for dimethoxyphosphoryl group, 0.57 for sulfamoyl group, 0.42 for formyl group, 0.31 for acetoxy group, 0.18 for phenylthio group, 0.44 for acetylthio group, 0.23 for chlorine atom, 0.23 for bromine atom, 0.29 for tribromomethyl group, 0.33 for trifluoromethyl group, 0.54 for trifluoromethyl group, 0.41 for pentafluorophenyl group, 0.35 for trifluoroalkoxy group, 0.53 for N,N-trifluoromethanamino group, and 0.30 for 2,4,6-trinitrophenyl group.

Preferred among the groups represented by $R^7$ are formyl group, acyl group, acyloxy group, carbamoyl group, alkoxycarbonyl group, aryloxycarbonyl group, cyano group, nitro group, alkylsulfinyl group, arylsulfinyl group, alkylsulfonyl group, arylsulfonyl group, alkylsulfonyl group, sulfamoyl group, halogenated alkyl group, halogenated alkyloxy group, halogenated alkylthio group, halogenated aryloxy group, aryl group substituted by two or more electrophilic groups having a Hammett's substituent constant $\sigma_p$ of 0.15 or more, and heterocyclic group.

Further preferred among these groups are formyl group, carbamoyl group, alkoxycarbonyl group, aryloxycarbonyl group, and cyano group. Particularly preferred among these groups are cyano group, alkoxycarbonyl group, and aryloxycarbonyl group.

That is, $R^7$ is preferably a cyano group or —COR wherein R is preferably a hydrogen atom, $C_{0-36}$ amino group, preferably $C_{1-24}$ straight-chain, branched or cyclic alkoxy group, or $C_{6-36}$, preferably $C_{6-24}$ aryloxy group. These amino, alkoxy and aryloxy groups may be substituted by substituents such as substituent group A.

Alternatively, $R^7$ is preferably a cyano group or —COR wherein R is preferably an unsubstituted, alkyl-substituted, aryl-substituted or heterocyclic group-substituted amino group (these alkyl-substituted, aryl-substituted and heterocyclic group-substituted amino groups may be further substituted by the substituent group A; the alkyl in the alkyl-substituted amino group may be a straight-chain, branched or cyclic alkyl group; examples of such alkyl-substituted amino groups include amino, ethylamino, n-dodecylamino, anilino, 2-chloroanilino, 2-naphthylamino, 2-pyridyl-2-amino), straight-chain, branched or cyclic unsubstituted alkoxy group or alkoxy group containing substituents such as alkoxy group, alkylthio group, aryloxy group, arylthio group, alkylsulfonyl group, arylsulfonyl group, aryl group, alkoxycarbonyl group, epoxy group, cyano group and halogen atom (e.g., methoxy, ethoxy, isopropoxy, isobutoxy, n-octyloxy, n-decyloxy, n-dodecyloxy, n-hexadecyloxy, 2-ethylhexyloxy, 3,5,5-trimethylhexyloxy, 2-ethyl-4-methylpentyloxy, 2-hexyldecyloxy, 2-heptylundecyloxy, 2-octyldodecyloxy, 2,4,6-trimethylheptyloxy, 2,4,6,8-tetramethylnonyloxy, benzyloxy, 2-phenethyloxy, 3-(t-octylphenoxy)propoxy, 3-(2,4-di-t-pentyphenoxy)propoxy, 2-(4-biphenyloxy)ethoxy, 3-dodecyloxypropoxy, 2-dodecylthioethoxy, 9,10-epoxyoctadecyloxy, dodecyloxycarbonylmethoxy, 2-(2-naphthyloxy)ethoxy, 7,7-dimethyl-2-(3',3'-dimethylbutyl)-5-methyloctyloxy, 2-methyl-cyclohexyloxy, 2-hexyl-cyclohexyloxy), unsubstituted aryloxy group or aryloxy group containing substituents (substituent group A) (e.g., phenoxy, 2-t-amylphenoxy, 4-dodecyloxyphenoxy).

$R^8$ and $R^9$ each independently represents a hydrogen atom or nonmetallic atomic group. In particular, $R^8$ and $R^9$ each independently represents a hydrogen atom, aryl group, heterocyclic group, alkyl group, cyano group, carboxyl group, formyl group, acyl group, carbamoyl group, alkoxycarbonyl group, aryloxycarbonyl group, acylamino group, alkoxycarbonylamino group, aryloxycarbonylamino group, sulfonylamino group, aminocarbonylamino group, sulfamoylamino group, amino group (including anilino group), alkoxy group, aryloxy group, silyloxy group, heteryloxy group, alkylthio group, arylthio group, heterylthio group, halogen atom, hydroxyl group, nitro group, sulfamoyl group, sulfonyl group, azo group, acyloxy group, carbamoyloxy group, imido group, sulfinyl group, phosphoryl group or azolyl group. Of these nonmetallic atomic groups, those which can contain substituents may be substituted by substituents such as substituent group A.

Specific examples of $R^8$ and $R^9$ include hydrogen atom, aryl group (preferably $C_{6-30}$ aryl group, e.g., phenyl, macetylaminophenyl, p-methoxyphenyl), alkyl group (preferably $C_{1-30}$ alkyl group, e.g., methyl, ethyl, isopropyl, t-butyl, noctyl, n-dodecyl), cyano group, carboxyl group, acyl group (preferably $C_{1-30}$ acyl group, e.g., acetyl, pivaloyl, benzoyl, furoil, 2-pyridylcarbonyl), carbamoyl group (preferably $C_{1-30}$ carbamoyl group, e.g., methylcarbamoyl, ethylcarbamoyl, dimethylcarbamoyl, n-octylcarbamoyl), alkoxycarbonyl group (preferably $C_{1-30}$ alkoxycarbonyl group, e.g., methoxycarbonyl, ethoxycarbonyl, isopropoxycarbonyl), aryloxycarbonyl group (preferably $C_{7-30}$ aryl group, e.g., phenoxycarbonyl, p-methoxyphenoxycarbonyl, m-chlorophenoxycarbonyl, o-methoxyphenoxycarbonyl), acylamino group (preferably $C_{1-30}$ alkylcarbonylamino group, e.g., formylamino, acetylamino, propionylamino, cyanoacetylamino, $C_{7-30}$ arylcarbonylamino group, e.g., benzoylamino, p-toluylamino, pentafluorobenzoylamino, m-methoxybenzoylamino, or $C_{4-30}$ heterylcarbonylamino group, e.g., 2-pyridylcarbonylamino, 3-pyridylcarbonylamino, furoylamino), alkoxycarbonylamino group (preferably $C_{2-30}$ alkoxycarbonylamino group, e.g., methoxycarbonylamino, ethoxycarbonylamino, methoxyethoxycarbonylamino), aryloxycarbonylamino group (preferably $C_{7-30}$ aryloxycarbonylamino group, e.g., phenoxycarbonylamino, p-methoxyphenoxycarbonylamino, p-methylphenoxycarbonylamino, m-chlorophenoxycarbonylamino, o-chlorophenoxycarbonylamino), sulfonylamino group (preferably $C_{1-30}$ sulfonylamino group, e.g., methanesulfonylamino, benzenesulfonylamino, toluenesulfonylamino), aminocarbonylamino group (preferably $C_{1-30}$ aminocarbonylamino group, e.g., methylaminocarbonylamino, ethylaminocarbonylamino, anilinocarbonylamino, dimethylaminocarbonylamino), sulfamoylamino group (preferably $C_{1-30}$ group, e.g., methylaminosulfonylamino, ethylsulfamoylamino aminosulfonylamino, anilinosulfonylamino), amino group (including anilino group, preferably $C_{0-30}$ amino group, e.g., amino, methylamino, dimethylamino, ethylamino, diethylamino, n-butylamino, anilino), alkoxy group (preferably $C_{1-30}$ alkoxy group, e.g., methoxy, ethoxy, isopropoxy, n-butoxy, methoxyethoxy, n-dodecyloxy), aryloxy group (preferably $C_{6-30}$ aryloxy group, e.g., phenoxy, m-chlorophenoxy, p-methoxyphenoxy, o-methoxyphenoxy), silyloxy group (preferably $C_{6-30}$ silyloxy group, e.g., trimethylsilyloxy, t-butyldimethylsilyloxy, cetyldimethylsilyloxy, phenyldimethylsilyloxy), heteryloxy group (preferably heteryloxy group, e.g., tetrahydropyranyloxy, 3-pyridyloxy, 2-(1,3-benzimidazolyl)oxy), alkylthio group (preferably alkylthio group, e.g., methylthio, ethylthio, n-butylthio, t-butylthio), arylthio group (preferably $C_{6-30}$ arylthio group, e.g., phenylthio), heterylthio group (preferably $C_{3-30}$ heterylthio group, e.g., 2-pyridylthio, 2-(1,3-benzoxazolyl)thio, 1-hexadecyl-1,2,3,4-tetrazolyl-5-thio, 1-(3-N-octadecylcarbamoyl)phenyl-1,2,3,4-tetrazolyl-5-thio), heterocyclic group (preferably $C_{3-30}$ heterocyclic group, e.g., 2-benzoxazolyl, 2-benzothiazolyl, 1-phenyl-2-benzimidazolyl, 5-chloro-1-tetrazolyl, 1-pyrrolyl, 2-furanyl, 2-pyridyl, 3-pyridyl), halogen atom (e.g., fluorine, chlorine, bromine), hydroxyl group, nitro group, sulfamoyl group (preferably $C_{0-30}$ sulfamoyl group, e.g., methylsulfamoyl, dimethylsulfamoyl), sulfonyl group (preferably $C_{1-30}$ sulfonyl group, e.g., methanesulfonyl, benzenesulfonyl, toluenesulfonyl), azo group (preferably $C_{3-30}$ azo group, e.g., p-nitrophenylazo), acyloxy group (preferably $C_{3-30}$ acyloxy group, e.g., formyloxy, acetyloxy, benzoyloxy), carbamoyloxy group (preferably $C_{1-30}$ aryl group, e.g., methylcarbamoyloxy, diethylcarbamoyloxy), imido group (preferably $C_{4-30}$ imido group, e.g., succinimido, phthalimido), sulfinyl group (preferably $C_{1-30}$ sulfinyl group, e.g., diethylaminosulfinyl), phosphoryl group (preferably $C_{0-30}$ phosphoryl group, e.g., diaminophosphoryl), and azolyl group (preferably $C_{2-30}$ azolyl group, e.g., 3-pyrazolyl).

Among these specific examples of $R^8$, $\sigma_p$ values other than those described with reference to $R^7$ are 0.00 for hydrogen atom, −0.17 for methyl group, −0.15 for ethyl group, −0.01 for phenyl group, 0.00 for acetylamino group, 0.03 for methanesulfonamido group, −0.15 for carbonylamino group, etc.

$R^8$ preferably represents an electrophilic group having a Hammett's substituent constant $\sigma_p$ of 0.15 or more, i.e., it is synonymous with $R^7$. Particularly preferred examples of $R^8$ include cyano group, formyl group, carbamoyl group, alkoxycarbonyl group, and aryloxycarbonyl group. That is, $R^8$ is preferably a cyano group or —COR wherein R is the same as defined above for $R^7$. More preferred among these groups are cyano group, alkoxycarbonyl group, and aryloxycarbonyl group. Particularly preferred among these groups are alkoxycarbonyl group and aryloxycarbonyl group.

In the present invention, the sum of $\sigma_p$ values of $R^7$ and $R^8$ is 0.65 or more. Any combination of $R^7$ and $R^8$ is possible so far as $R^7$ has a $\sigma_p$ value of 0.15 or more. Examples of such a combination will be set forth below, but the present invention should not be construed as being limited thereto.

| $R^7$ |  | $R^8$ |  | Sum |
|---|---|---|---|---|
| CN | 0.66 | CN | 0.66 | 1.32 |
| CN | 0.66 | COCH$_3$ | 0.50 | 1.16 |
| CN | 0.66 | CO$_2$CH$_3$ | 0.45 | 1.11 |
| CN | 0.66 | CONH$_2$ | 0.36 | 1.02 |
| CONH$_2$ | 0.36 | CONH$_2$ | 0.36 | 0.72 |
| CONH$_2$ | 0.36 | CN | 0.66 | 1.02 |
| CONH$_2$ | 0.36 | CO$_2$CH$_3$ | 0.50 | 0.86 |
| COCH$_3$ | 0.50 | CN | 0.66 | 1.16 |
| COCH$_3$ | 0.50 | COCH$_3$ | 0.50 | 1.00 |
| NO$_2$ | 0.78 | C$_6$H$_5$ | −0.01 | 0.77 |
| CN | 0.66 | CO$_2$C$_6$H$_5$ | 0.44 | 1.10 |
| CO$_2$C$_6$H$_5$ | 0.44 | CHO | 0.42 | 0.86 |
| CN | 0.66 | CONHCH$_3$ | 0.36 | 1.02 |
| CN | 0.66 | CF$_3$ | 0.54 | 1.20 |

Preferred examples of $R^9$ include aryl group, heterocyclic group, and alkyl group. Suitable among these groups is aryl group, preferably $C_{6-36}$, more preferably $C_{6-30}$ aryl group. The aryl group is preferably an unsubstituted aryl group or an aryl group containing substituents (substituent group A) or which may be condensed (e.g., phenyl, 3-nitrophenyl, 4-nitrophenyl, 4-cyanophenyl, 3,4-dicyanophenyl, 3,4-dimethoxycarbonylphenyl, 3-(2-octyloxy-5-t-octyl)phenylsulfonylaminophenyl, 3,5-dichlorophenyl, 4-[1-(2,4-ditamylphenoxy)propanoylamino]phenyl, 4-(2-hexyldecyloxy)phenyl, 2-(2-hexyldecyloxy)phenyl, and 3-(2,4-di-t-amylphenoxyacetylamino)phenyl).

Preferred examples of substituents to be contained in the substituted aryl group include nitro group, halogen atom, cyano group, acylamino group, and sulfonamido group. Particularly preferred among these substituents is chlorine atom.

Z preferably represents a hydrogen atom, halogen atom, $C_{6-36}$ t preferably $C_{6-24}$ arylthio group, $C_{1-36}$, preferably $C_{1-24}$ arylsulfinyl group, $C_{1-36}$, preferably $C_{1-24}$ heterocyclic thio group, or nitroso group. These arylthio group, arylsulfinyl group and heterocyclic thio group may be substituted by the substituent group A.

Preferred examples of Z include hydrogen atom, halogen atom (e.g., fluorine atom, chlorine atom, bromine atom), unsubstituted arylthio group or arylthio group containing substituents such as halogen atom, alkyl group, alkoxy group, cyano group, aryloxycarbonyl group, alkoxycarbonyl group, ureido group, alkoxycarbonylamino group, acylamino group and carboxyl group (e.g., 2-(n-butoxy)-5-(t-octyloxy)phenylthio, 2-(t-amylcarbonylamino)phenylthio, 2-(phenoxycarbonylamino)phenylthio, 2-(phenoxycarbonyl)phenylthio, 2-(3,3-dimethylureido)phenylthio, pentafluorophenylthio, pentachlorophenylthio, 1,3,5-triisopropylphenylthio), unsubstituted arylsulfinyl group or arylsulfinyl group containing substituents such as halogen atom, alkyl group, alkoxy group, cyano group, alkoxycarbonyl group and carboxyl group (e.g., 2-(n-butoxy)-5-(t-octyloxy)phenylsulfinyl, 2-(t-amylcarbonylamino)phenylsulfinyl, 2-(phenoxycarbonylamino)phenylsulfinyl, 2-(phenoxycarbonyl)phenylsulfinyl, 2-(3,3-dimethylureido)phenylsulfinyl, pentafluorophenylsulfinyl, pentachlorophenylsulfinyl, 1,3,5-triisopropylphenylsulfinyl), unsubstituted heterocyclic thio group or heterocyclic thio group containing substituents such as halogen atom, alkyl group, alkoxy group, cyano group, alkoxycarbonyl group, carboxyl group and nitro group (e.g., pyrazolylthio, 5-nitro-2-pyridylthio) or nitroso group.

Preferred among these groups are hydrogen atom, arylthio group, and arylsulfinyl group.

The compound represented by formula (V) also indicates various compounds in equilibrium as shown below:

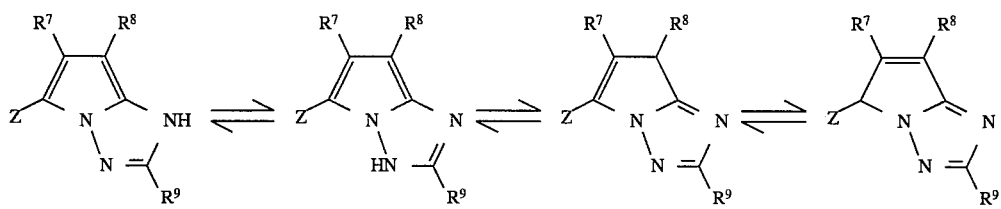

If the compounds of the present invention represented by formulae (I) to (IV) are used as cyan dyes for heat transfer application, substituents are preferably selected such that the molecular weight of these dyes each is 700 or less, more preferably 600 or less.

The dyes of the present invention may contain an atomic group having an effect of inhibiting discoloration in their molecules. Such dyes are desirable particularly when a high image fastness is required.

The atomic group having an effect of inhibiting discoloration may be connected to any position of $R^1$, $R^2$, $R^3$, $R^4$, $R^5$, $R^6$, $R^7$, $R^8$ and $R^9$ in formulae (I) to (IV).

As such an atomic group having an effect of inhibiting discoloration there can be used any of those described in Japanese Patent Application No. Hei 2-277665.

Specific examples of such an atomic group having an effect of inhibiting discoloration will be set forth below, but the present invention should not be construed as being limited thereto.

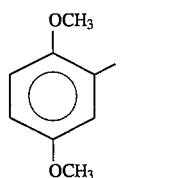

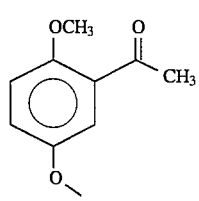

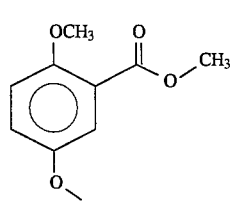

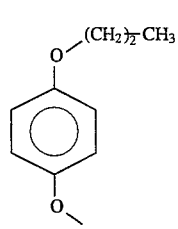

-continued

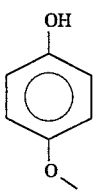

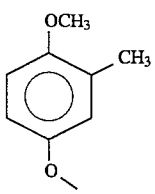

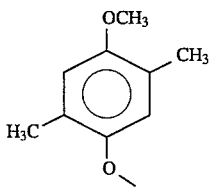

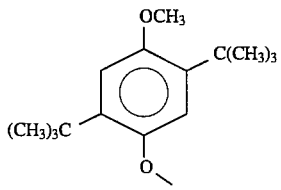

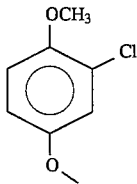

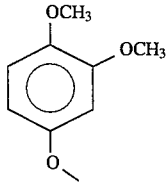

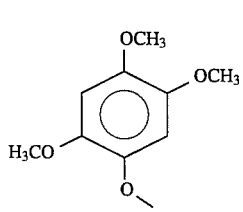

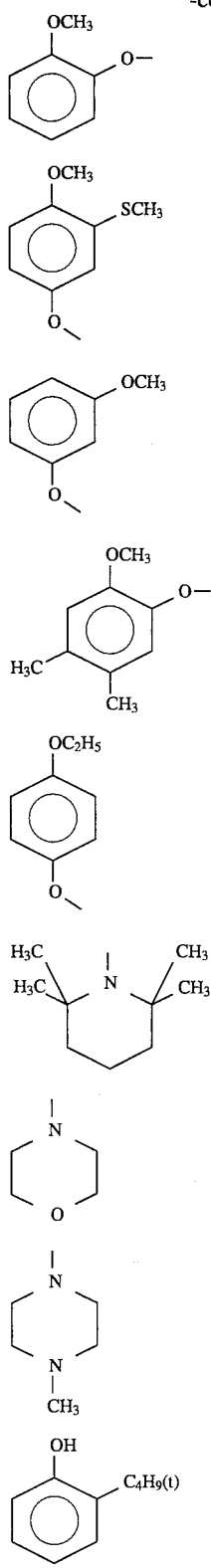
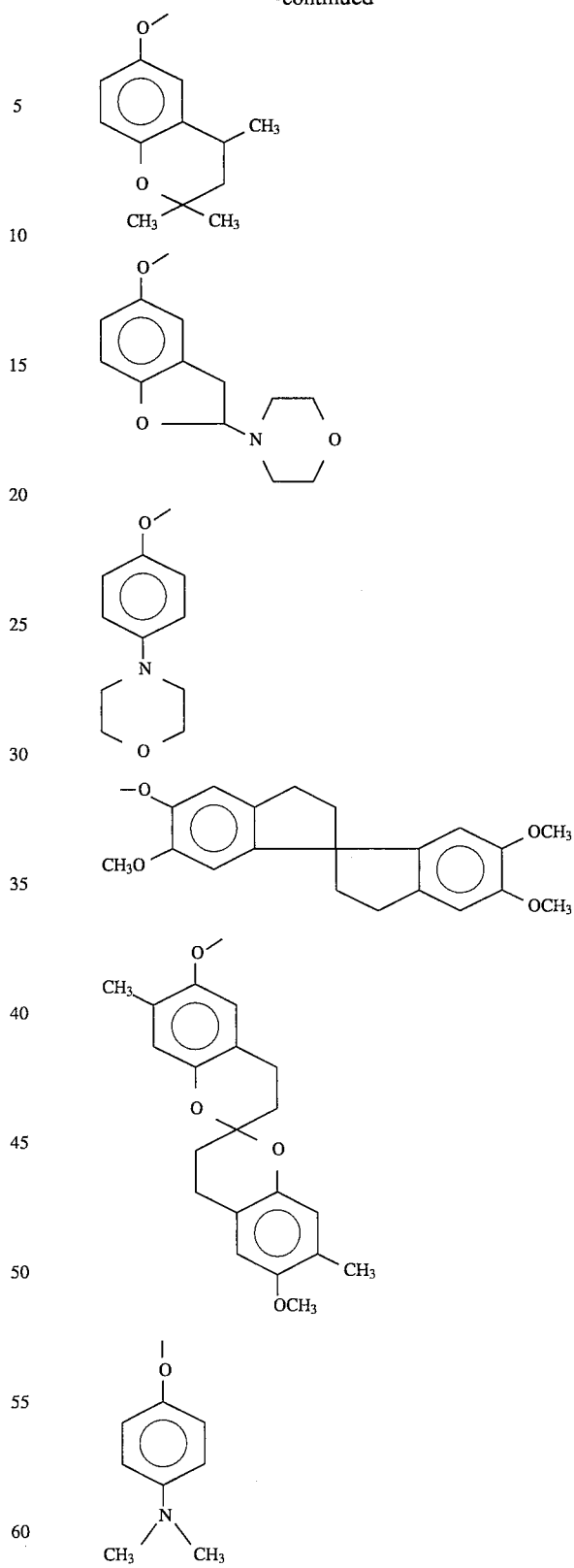

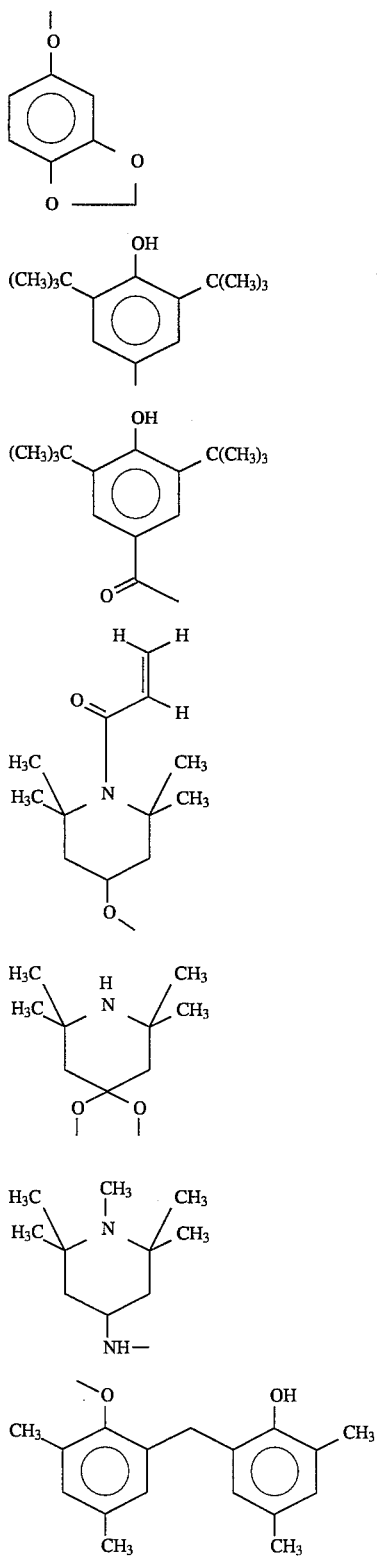
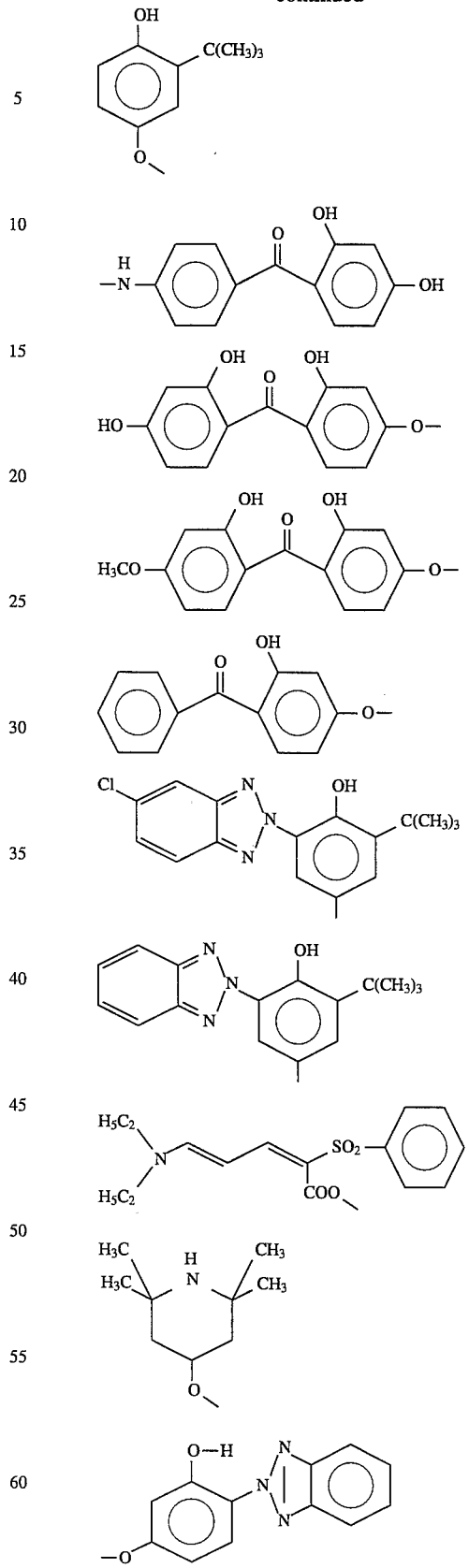

Among the dyes of the present invention, those represented by formulae (I) and (II) are preferred to those represented by formulae (III) and (Iv). In particular, those represented by formula (I) are preferred.

Specific examples of the compound of the present invention will be set forth below, but the present invention should not be construed as being limited thereto.

Firstly, specific examples of the compounds represented by formulae (I) and (V) will be given. In the structural formulae shown below, $(t)C_5H_{11}$ indicates $-C(CH_3)_2C_2H_5$, and $(t)C_8H_{17}$ indicates $-C(CH_3)_2CH_2C(CH_3)_3$. $M^+$ indicates the value ($M^+$) of the master peak of mass spectrum. λmax(nm) indicates the maximum absorption wavelength of ethyl acetate solution of a compound represented by formula (VI) when derived from the compound represented by formula (I):

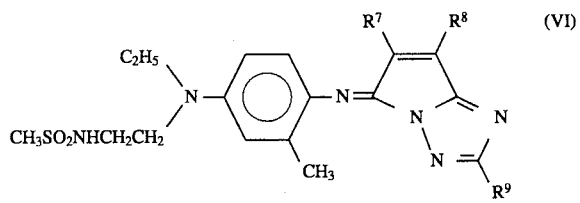

Some examples of the compound represented by formula (V) will be shown with their melting points (m.p.).

| Comp. No. | $R^8$ | $M^+$ | $R^7$ | Z | $R^9$ | λmax (nm) | m.p. | λmax (nm) |
|---|---|---|---|---|---|---|---|---|
| V-1 | CN | 583 | COOCH$_3$ | H | 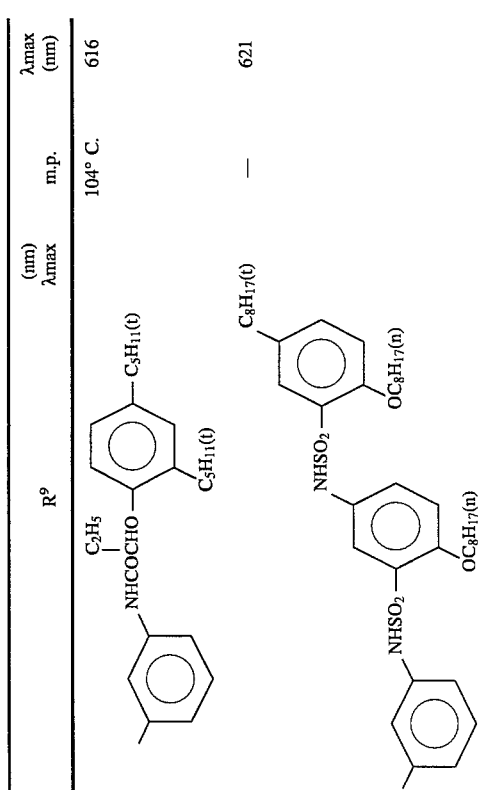 | | 104° C. | 616 |
| V-2 | CN | 1077 | COOCH$_2$CHC$_4$H$_9$(n)<br>　　　　　｜<br>　　　　C$_2$H$_5$ | Cl | 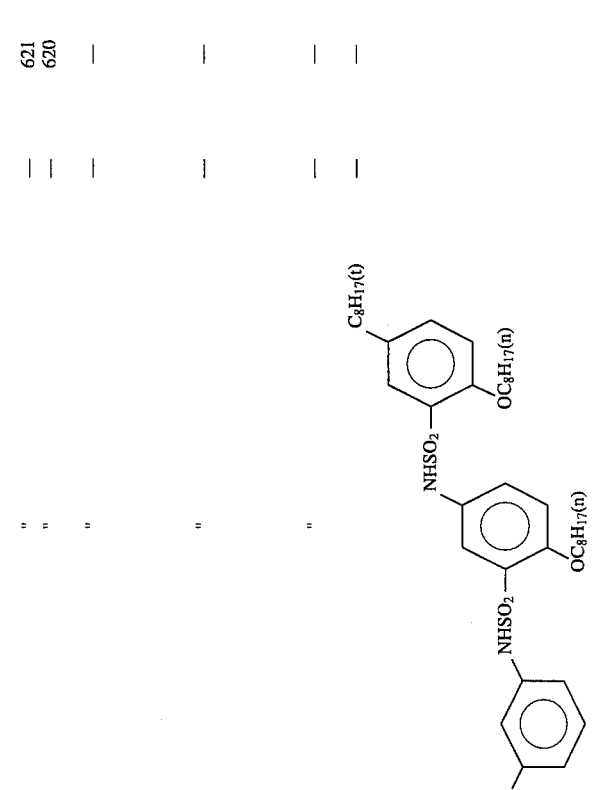 | | — | 621 |
| V-3 | CN | 1021 | COOC$_4$H$_9$(i) | Cl | " | | — | 621 |
| V-4 | CN | 1021 | COOC$_4$H$_9$(n) | Cl | " | | — | 620 |
| V-5 | CN | 1036 | COOC$_4$H$_9$(n)—⟨C$_6$H$_4$⟩—CONH—⟨C$_6$H$_4$⟩—OCH$_3$ | H | " | | — | — |
| V-6 | CN | 1070 | COOC$_4$H$_9$(n)—⟨C$_6$H$_4$⟩—CONH—⟨C$_6$H$_4$⟩—OCH$_3$ | Cl | " | | — | — |
| V-7 | CN | 1007 | COOC$_3$H$_7$(i) | Cl | " | | — | — |
| V-8 | CN | 973 | COOC$_3$H$_7$(i) | H | " | | — | — |

-continued

| Comp. No. | R⁸ | M⁺ | R⁷ | Z | λmax (nm) | m.p. | R⁹ | λmax (nm) |
|---|---|---|---|---|---|---|---|---|
| V-9 | CN | 1237 | COOCH₃ | —S—(2-OC₄H₉(n), 4-C₈H₁₇(t))C₆H₃ | | 130° C. | " | — |
| V-10 | CN | 989 | COOCH₂CH₂OCH₃ | H | | — | " | — |
| V-11 | CN | 987 | COOC₄H₉(i) | H | | 200° C. | " | — |
| V-12 | CN | 1043 | COOCH₂CHC₄H₉(n) / C₂H₅ | H | | 127° C. | " | — |
| V-13 | CN | 987 | COOC₄H₉(n) | H | | — | " | — |
| V-14 | CN | 1279 | COOC₄H₉(n) | —S—(2-OC₄H₉(n), 4-C₈H₁₇(t))C₆H₃ | | — | " | — |
| V-15 | CN | 1208 | COOC₄H₉(i) | —S—(2-NHCOCH₂C₄H₉(t))C₆H₄ | | 205° C. | 3-(NHSO₂-(2-OC₈H₁₇(n))-5-(NHSO₂-(2-OC₈H₁₇(n), 4-C₈H₁₇(t))C₆H₃)-4-methylphenyl) | — |
| V-16 | CN | 1230 | COOC₄H₉(i) | —S—(2-NHCOO-C₆H₅)C₆H₄ | | — | " | — |

-continued
| Comp. No. | $R^8$ | $M^+$ | $R^7$ | Z | $R^9$ | λmax (nm) | m.p. | λmax (nm) |
|---|---|---|---|---|---|---|---|---|
| V-17 | CN | 1215 | $COOC_4H_9(i)$ | 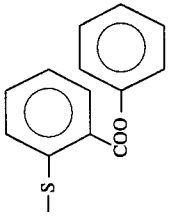 | " | | — | — |
| V-18 | CN | 1208 | $COOC_4H_9(i)$ | 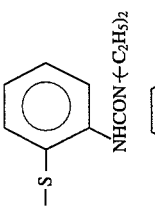 | " | | 194–197° C. | — |
| V-19 | CN | 1141 | $COOC_4H_9(i)$ | 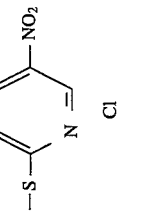 | " | | — | — |
| V-20 | CN | 618 | $COOCH_3$ | Cl | " | | 146° C. | — |
| V-21 | CN | 876 | $COOCH_3$ | 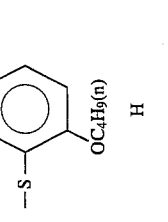 | " | | 103° C. | — |
| V-22 | $COOC_2H_5$ | 959 | CN | H |  | | — | 628 |

-continued

| Comp. No. | R⁸ | M⁺ | R⁷ | Z | R⁹ | λmax (nm) | m.p. | λmax (nm) |
|---|---|---|---|---|---|---|---|---|
| V-23 | COOCH₂CH(C₂H₅)C₄H₉(n) | 1043 | CN | H | " | — | 182° C. | — |
| V-24 | COOC₄H₉(i) | 987 | CN | H | | | 157° C. | 630 |
| V-25 | COOCH₂CH(C₆H₁₃(n))(C₈H₁₇(n)) | 545 | CN | H | 3,5-dichloro-4-methylphenyl | | 97° C. | 629 |
| V-26 | COOC₂H₅ | 597 | CN | H | 4-(2,4-di-t-C₅H₁₁-phenoxy)-N-(p-tolyl)-N-(CH(C₂H₅)COCHO)amino | | 114° C. | 625 |
| V-27 | COOCH₂CH(CH₃)CH₂CH₂C₄H₉(t), CH₂—CH(CH₃)CH₂CH₂C₄H₉(t) | 822 | CN | H | 4-(2,4-di-t-C₅H₁₁-phenoxy)-N-(p-tolyl)-N-(CH(C₂H₅)COCHO)amino | | 78° C. | 627 |
| V-28 | COOC₂H₅ | 675 | CN | H | N-(p-tolyl)-NHSO₂-[4-C₈H₁₇(t)-2-OC₈H₁₇(n)-phenyl] | | — | 624 |
| V-29 | COOC₂H₅ | 675 | CN | H | N-(m-tolyl)-NHSO₂-[4-C₈H₁₇(t)-2-OC₈H₁₇(n)-phenyl] | | 240° C. | 629 |

-continued

| Comp. No. | R⁸ | M⁺ | R⁷ | Z | R⁹ | λmax (nm) | m.p. | λmax (nm) |
|---|---|---|---|---|---|---|---|---|
| V-30 | CH₃ / COOCH₂CHCHCH₂C₄H₉(t) / CH₂CH₂CHCH₂C₄H₉(t) / CH₃ | 900 | CN | H | 〃 | — | — | 640 |
| V-31 | COOC₁₄H₂₀(n) | 844 | CN | H | 〃 | 180° C. | — | — |
| V-32 | cyclohexyl-COO with CH₃ | 743 | CN | H | 〃 | >250° C. | — | — |
| V-33 | bicyclohexyl-COO | 812 | CN | H | [aryl with NHSO₂-tolyl, C₈H₁₇(t), OC₈H₁₇(n)] | 144° C. | — | — |
| V-34 | COOCH₂CH₂SO₂-C₆H₅ | 816 | CN | H | 〃 | 129° C. | — | — |
| V-35 | COOCH₂CH₂(CF₂)₆F | 993 | CN | H | 〃 | 194° C. | — | 638 |
| V-36 | COOCH₂(CF₂)₇H | 861 | CN | H | 〃 | 162° C. | — | 646 |
| V-37 | COOC₂H₅ | 968 | CN | —S—[aryl with C₈H₁₇(t), OC₄H₉(n)] | 〃 | 181° C. | — | — |

-continued

| Comp. No. | R⁸ | M⁺ | R⁷ | Z | R⁹ | λmax (nm) | m.p. | λmax (nm) |
|---|---|---|---|---|---|---|---|---|
| V-38 | COOC₂H₅ | 984 | CN | —S(→O)—(2-OC₄H₉(n), 5-C₈H₁₇(t))C₆H₃ | " | | 142° C. | — |
| V-39 | COOC₂H₅ | 815 | CN | —S—C₆H₄(2-OOC-C₆H₅) | 4-CH₃-C₆H₄-NH-[2-NHSO₂, (2-OC₈H₁₇(n), 5-C₈H₁₇(t))C₆H₃] | | 228° C. | — |
| V-40 | COOC₂H₅ | 817 | CN | —S—C₆F₅ | " | | 108–110° C. | — |
| V-41 | COOC₂H₅ | 900 | CN | —S—C₆Cl₅ | " | | — | — |
| V-42 | COOC₂H₅ | 909 | CN | —S—(2,6-di-C₃H₇(i), 4-C₃H₇(i))C₆H₂ | " | | 194–196° C. | — |

-continued

| Comp. No. | R⁸ | M⁺ | R⁷ | Z | R⁹ | λmax (nm) | m.p. | λmax (nm) |
|---|---|---|---|---|---|---|---|---|
| V-43 | CN | 944 | COOCH₃ | H | 3-methylphenyl-NHSO₂ / 4-OC₈H₁₇(n) substituted phenyl-NH- linked to phenyl with C₈H₁₇(t) and OC₈H₁₇(n), NHSO₂ | | 212° C. | 620 |
| V-44 | CN | 278 | CN | H | 4-NO₂-phenyl (p-tolyl) | | — | — |
| V-45 | COOC₂H₅ | 325 | CN | H | 4-NO₂-phenyl (p-tolyl) | | — | 629 |
| V-46 | COOC₂H₅ | 337 | CN | H | NHCOCH₃-phenyl (p-tolyl) | | 250° C. | — |
| V-47 | CN | 311 | COOCH₃ | H | 4-NO₂-phenyl (p-tolyl) | | — | — |
| V-48 | COOC₂H₅ | 348 | CN | H | 3,5-dichloro-phenyl (p-tolyl) | | — | 628 |
| V-49 | COOC₂H₅ | 325 | CN | H | 4-NO₂-phenyl (p-tolyl) | | — | — |

-continued

| Comp. No. | R⁸ | M⁺ | R⁷ | Z | R⁹ | λmax (nm) | m.p. | λmax (nm) |
|---|---|---|---|---|---|---|---|---|
| V-50 | CONH₂ | 296 | CN | H | 4-nitrophenyl (with NO₂) | — | — | 611 |
| V-51 | CN | 334 | COOCH₃ | H | 3,5-dichlorophenyl | — | 205–208° C. | 619 |
| V-52 | CN | 1023 | COOCH₂CH₂OCH₃ | Cl | bis(sulfonamido-aryl) group with C₈H₁₇(t), OC₈H₁₇(n), NHSO₂-tolyl | — | 143–145° C. | 635 |
| V-53 | CN | 1335 | COOCH₂CHC₄H₉(n) / C₂H₅ | —S— aryl (C₈H₁₇(t), OC₄H₉(n)) | | — | — | — |
| V-54 | COOC₂H₅ | 710 | CN | Cl | aryl with C₈H₁₇(t), OC₈H₁₇(n), NHSO₂-tolyl | — | — | — |
| V-55 | cyclohexyl-CONH- (H) | 378 | CN | H | 4-nitro-3-methylphenyl (NO₂) | — | — | 611 |

-continued
| Comp. No. | $R^8$ | $M^+$ | $R^7$ | Z | $R^9$ | $\lambda$max (nm) | m.p. | $\lambda$max (nm) |
|---|---|---|---|---|---|---|---|---|
| V-56 | COOC$_2$H$_5$ | 280 | CN | H |  | | — | 621 |
| V-57 |  | 504 | CN | H |  | | — | 624 |
| V-58 | COOCH$_3$ | 506 | CN | H |  | | — | — |
| V-59 |  | 808 | CN | H | 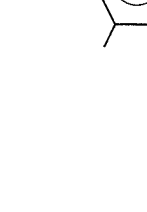 | | — | 644 |

Specific examples of the compounds represented by formulae (I) to (IV) will be given below. In the structural formulae shown below, Ph represents a phenyl group.
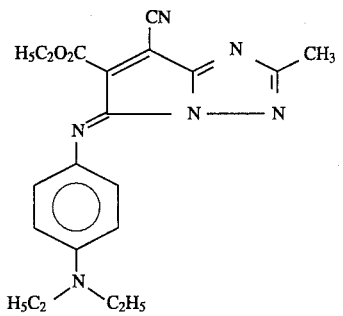
(I-1)
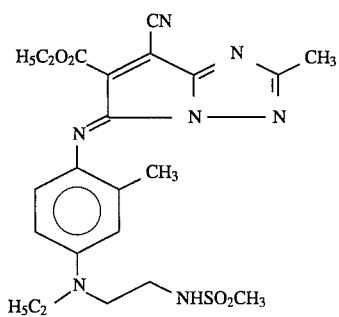
(I-2)
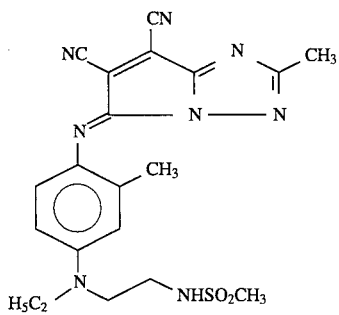
(I-3)
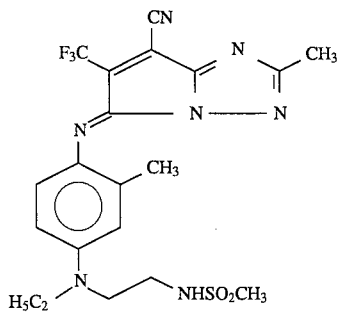
(I-4)
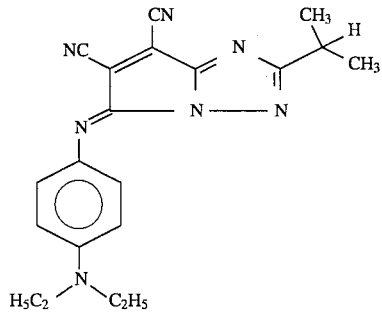
(I-5)

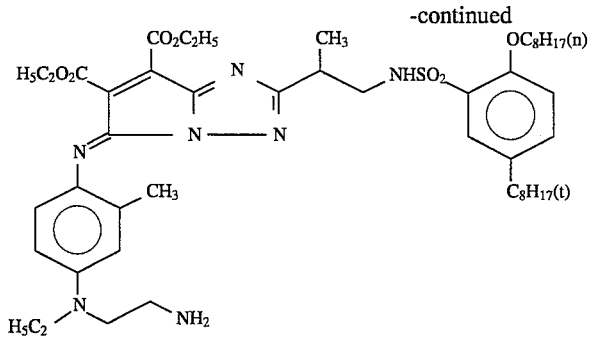 (I-6)
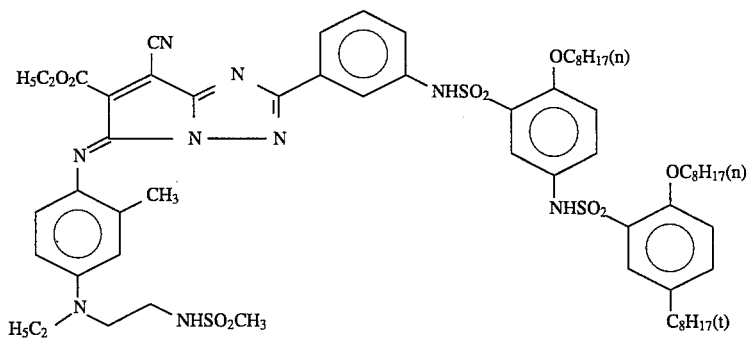 (I-7)
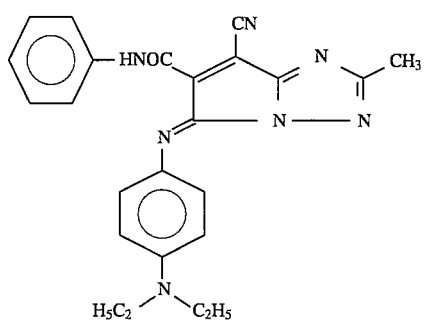 (I-8)
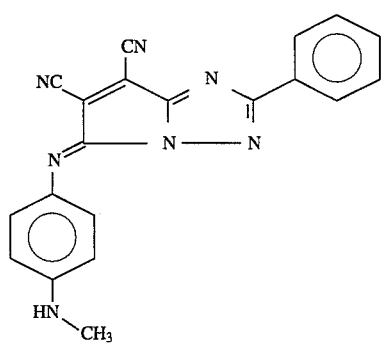 (I-9)
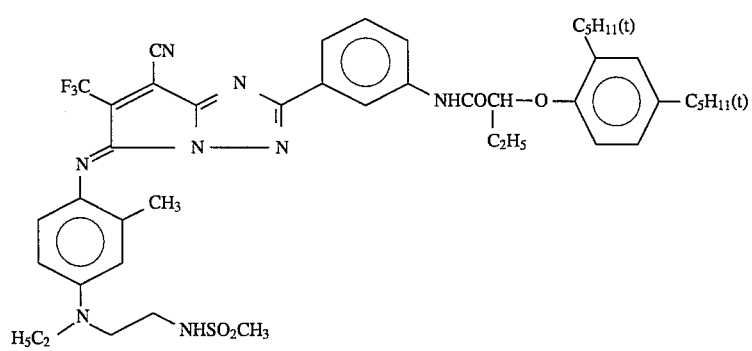 (I-10)

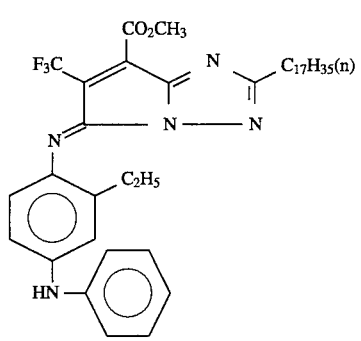
(I-11)
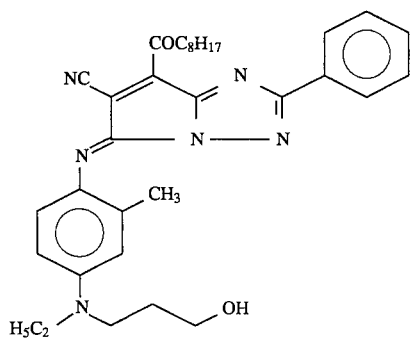
(I-12)
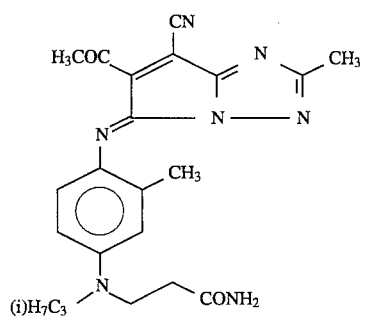
(I-13)
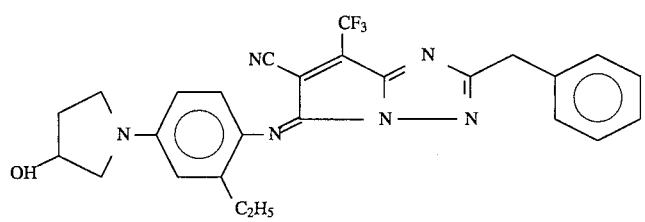
(I-14)
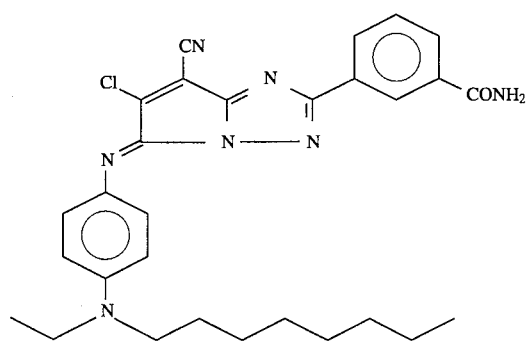
(I-15)

-continued
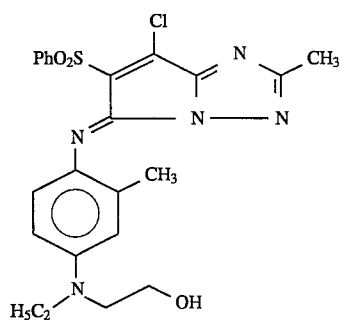
(I-16)
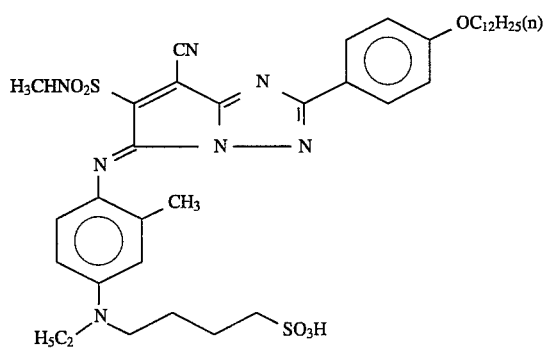
(I-17)
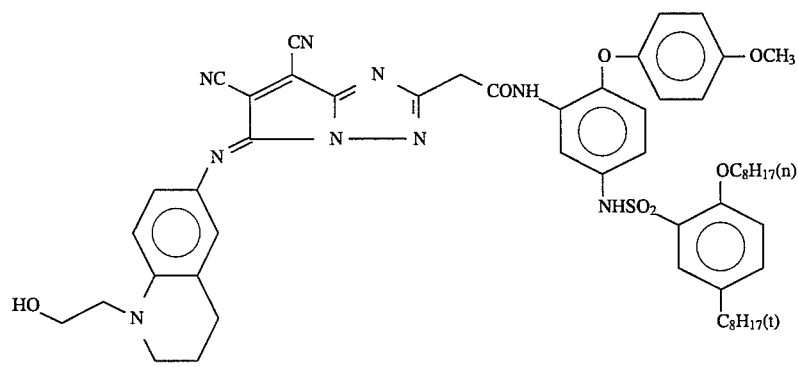
(I-18)
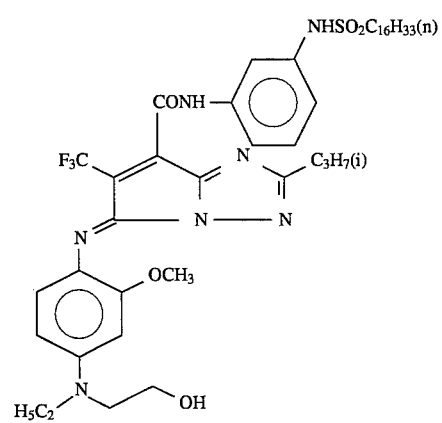
(I-19)

-continued
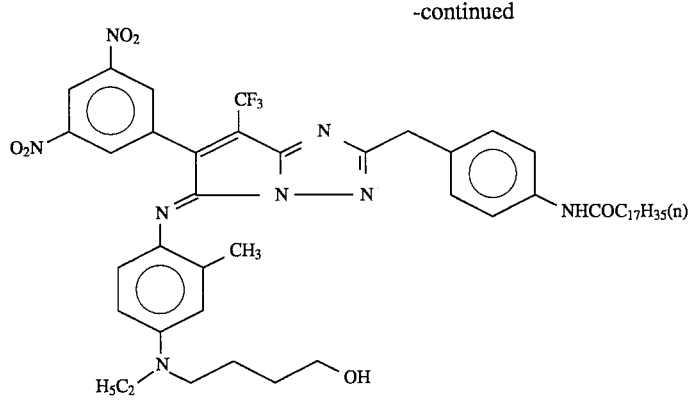
(I-20)
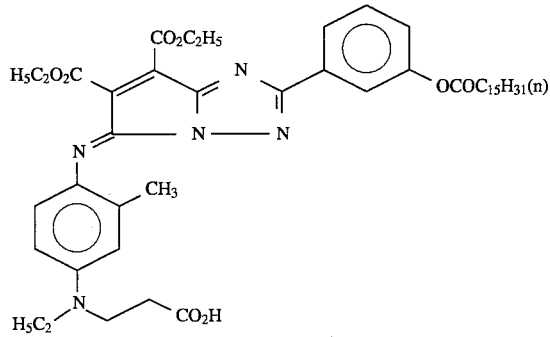
(I-21)
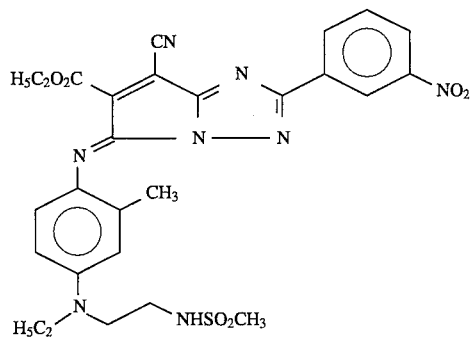
(I-22)
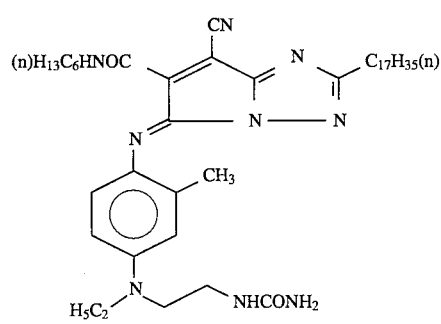
(I-23)
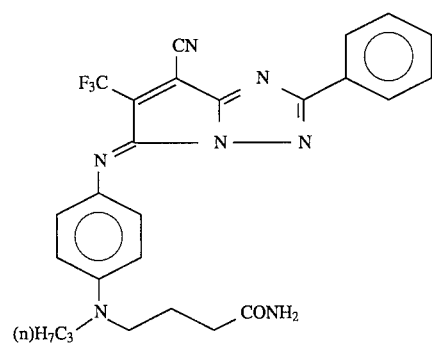
(I-24)

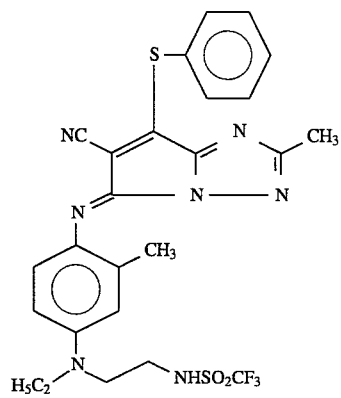
(I-25)
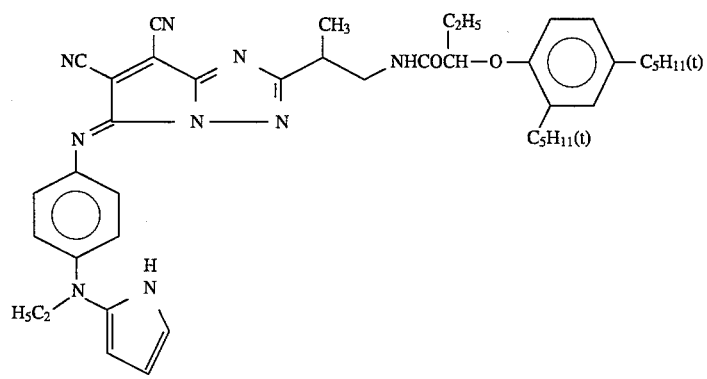
(I-26)
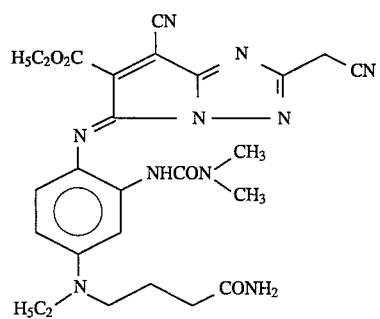
(I-27)
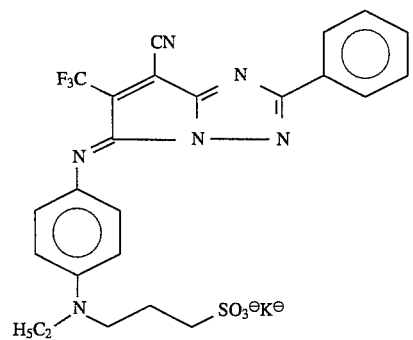
(I-28)

-continued
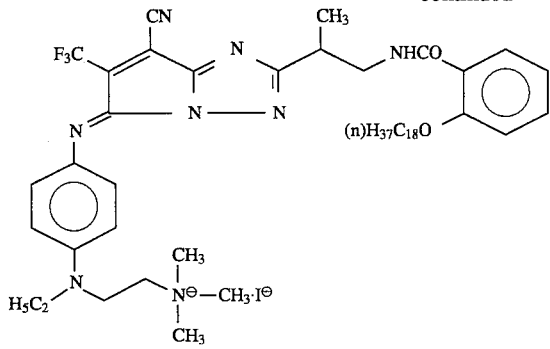
(I-29)
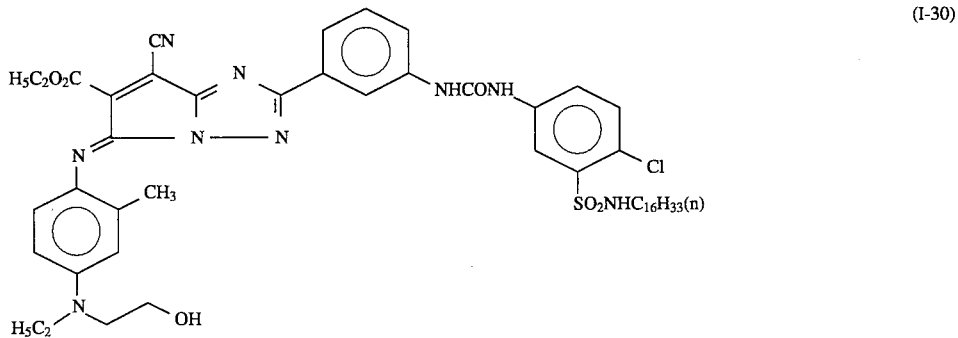
(I-30)
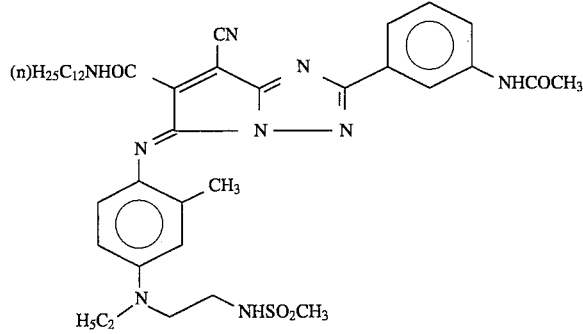
(I-31)
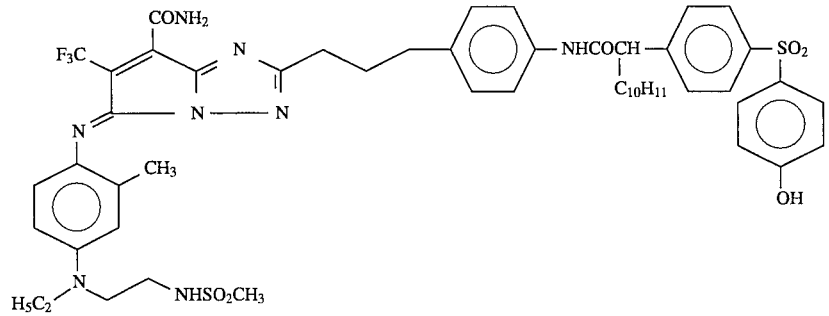
(I-32)

(I-33)
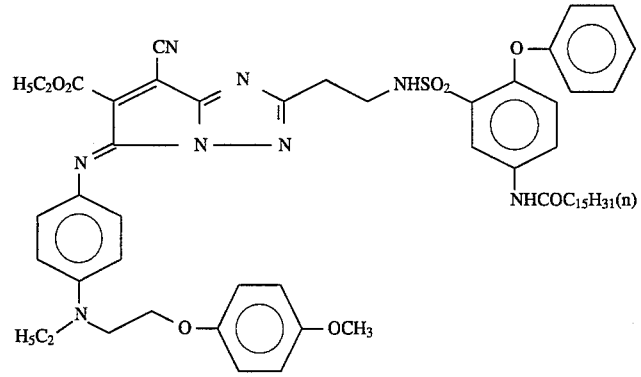
(I-34)
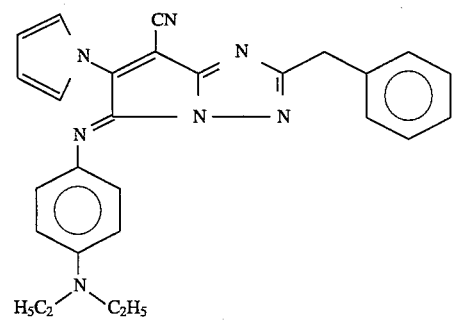
(I-35)
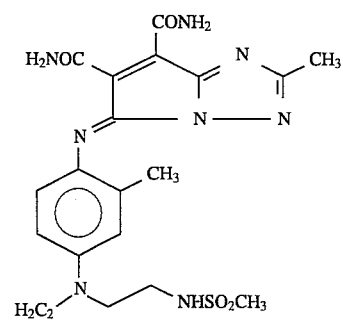
(I-36)
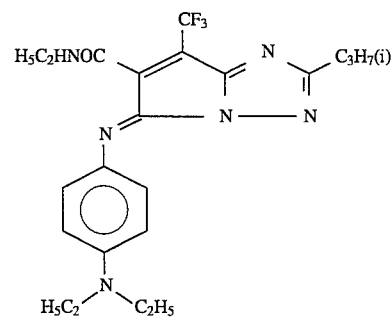
(I-37)
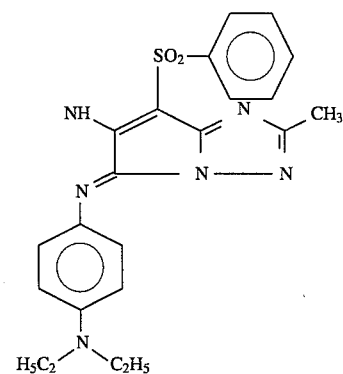

-continued
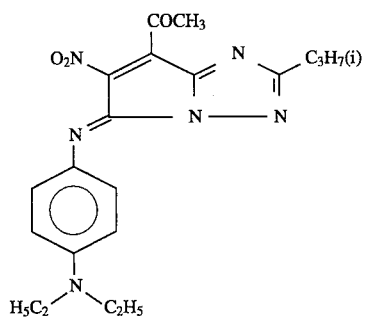
(I-38)
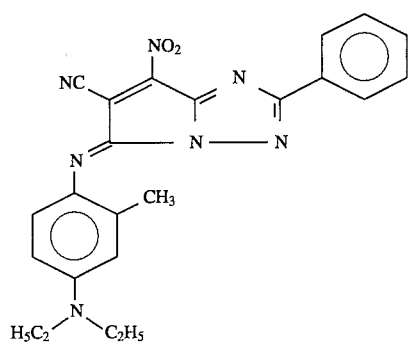
(I-39)
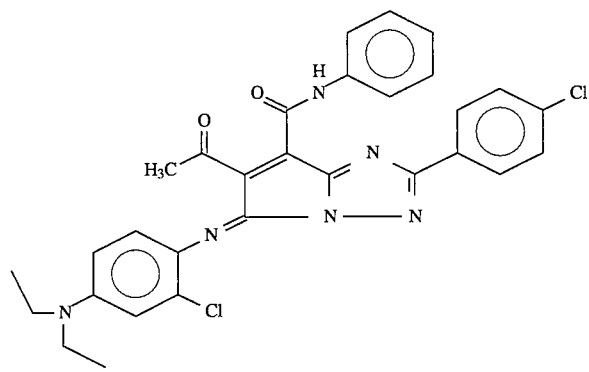
(I-40)
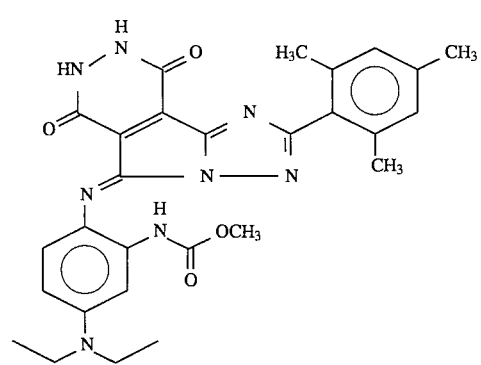
(I-41)

(I-42)
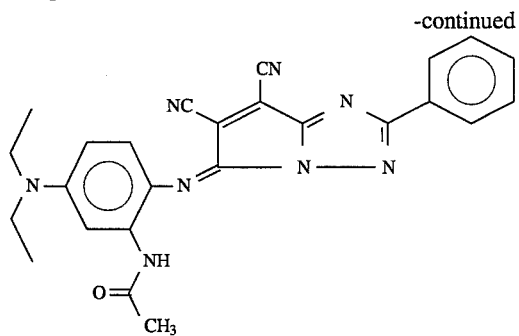
(I-43)
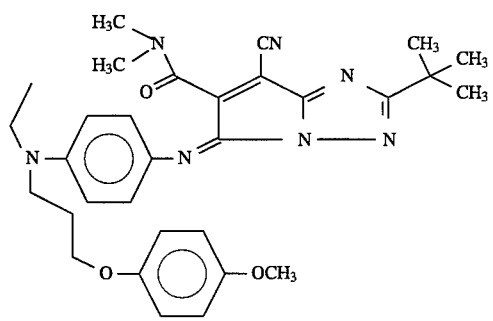
(I-44)
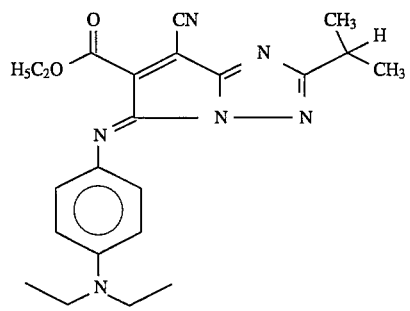
(I-45)
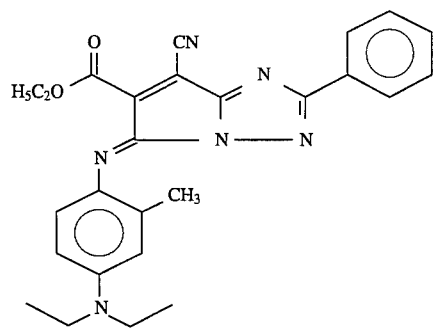
(I-46)
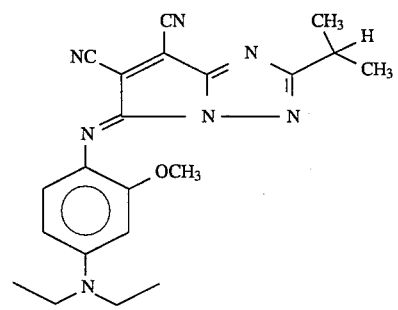

-continued
(I-47)
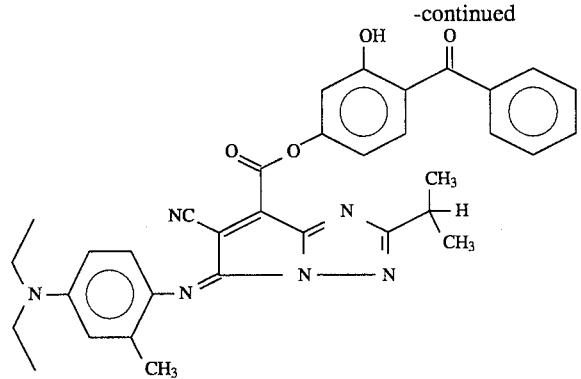
(I-48)
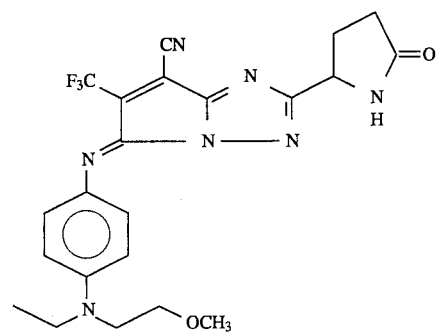
(II-1)
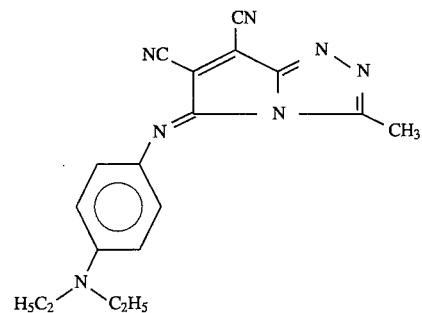
(II-2)
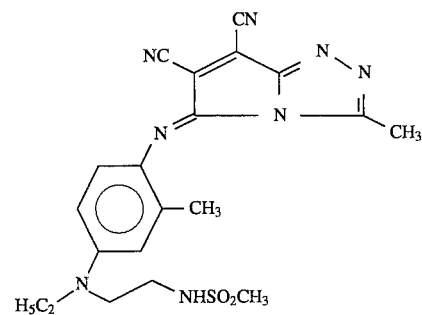
(II-3)
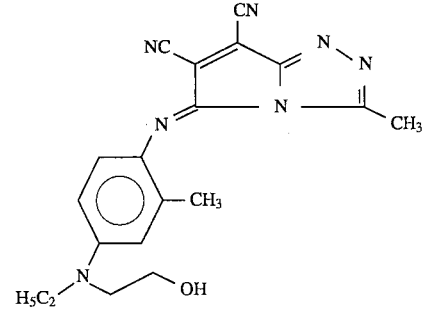

-continued
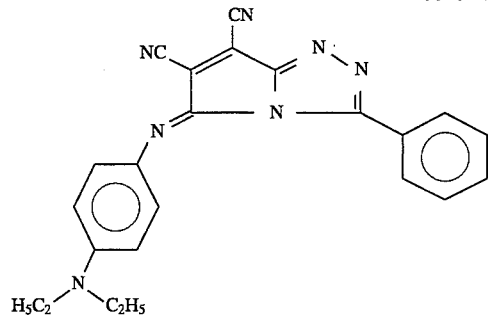
(II-4)
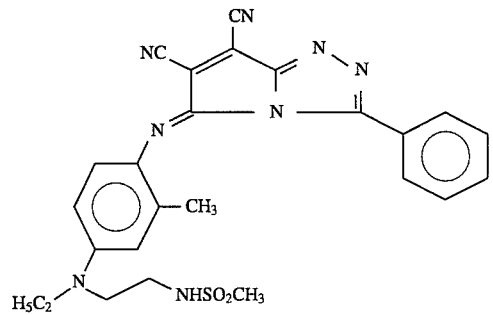
(II-5)
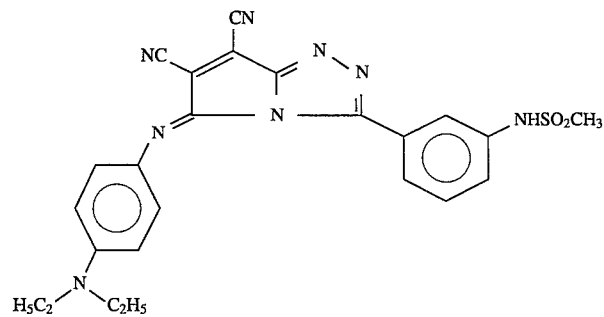
(II-6)
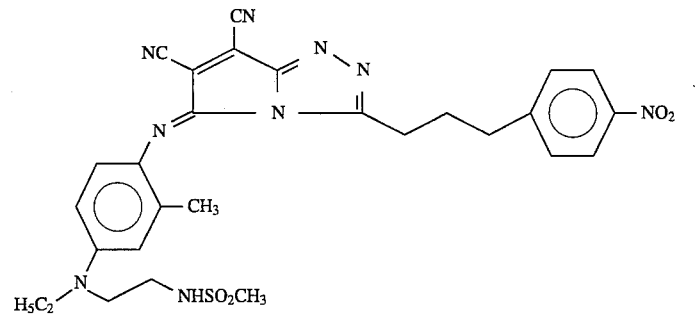
(II-7)
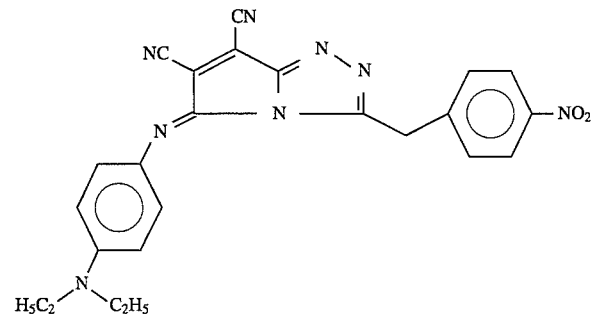
(II-8)

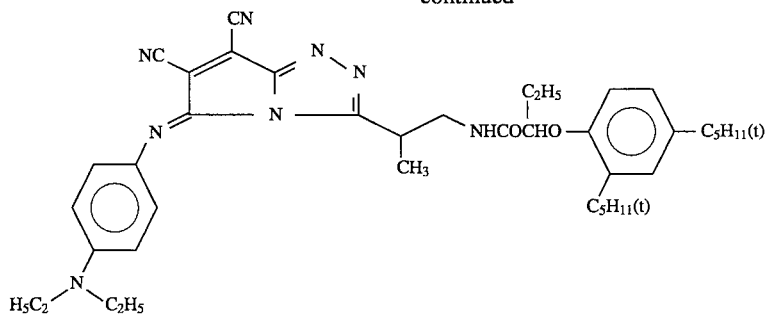
(II-9)
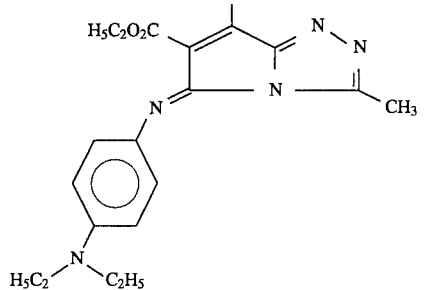
(II-10)
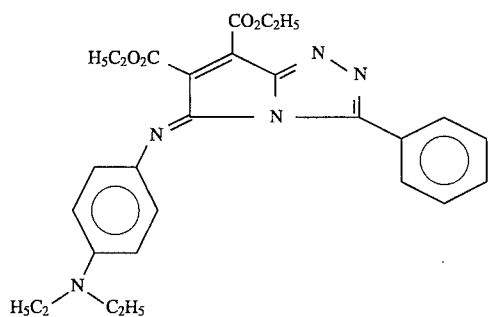
(II-11)
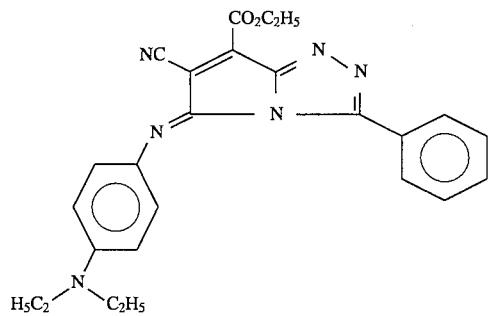
(II-12)
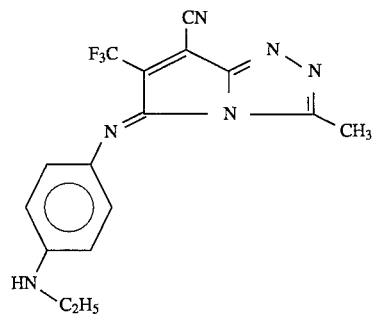
(II-13)

-continued
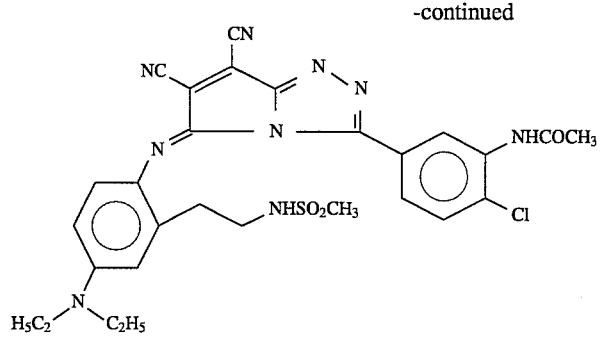 (II-14)
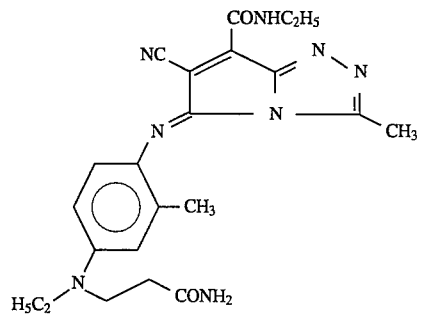 (II-15)
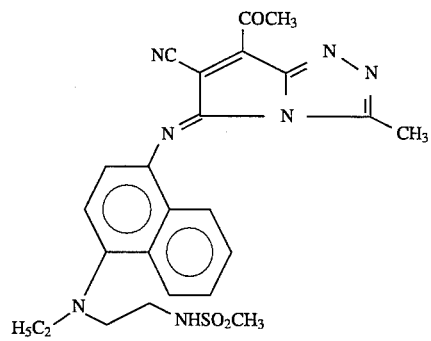 (II-16)
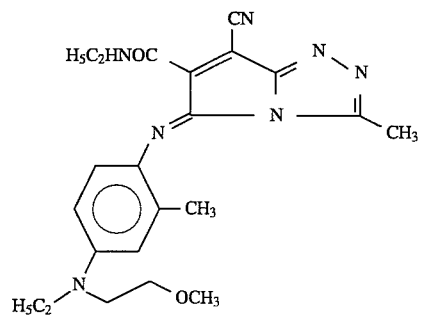 (II-17)
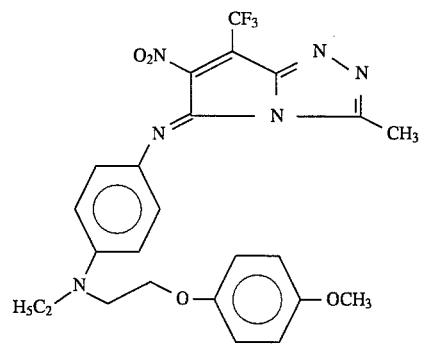 (II-18)

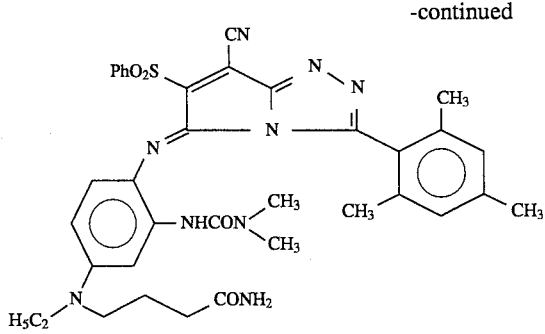
(II-19)
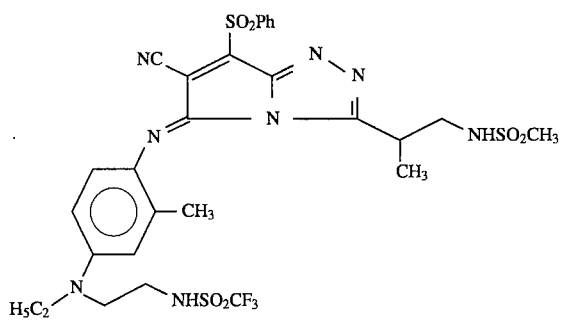
(II-20)
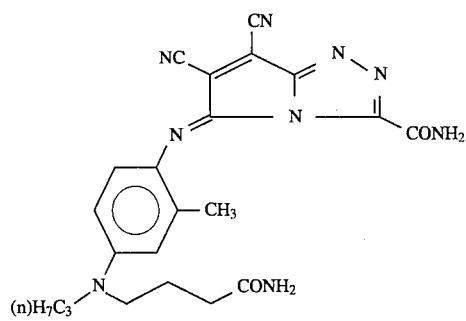
(II-21)
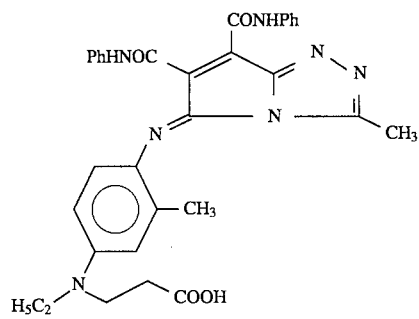
(II-22)
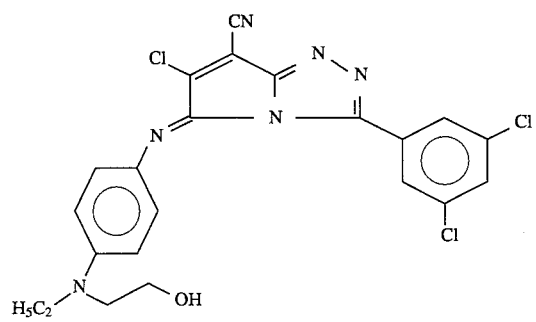
(II-23)

-continued
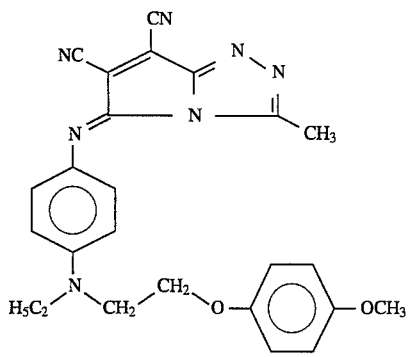 (II-24)
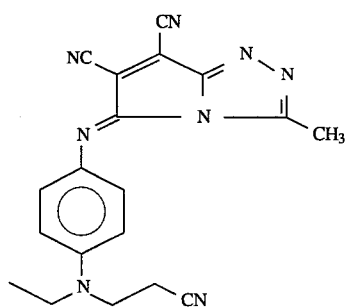 (II-25)
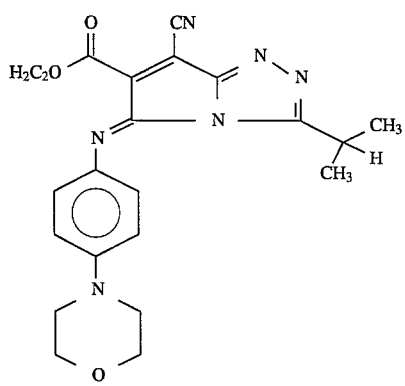 (II-26)
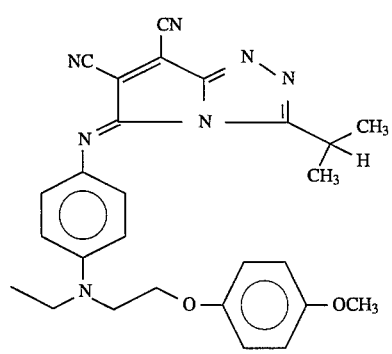 (II-27)

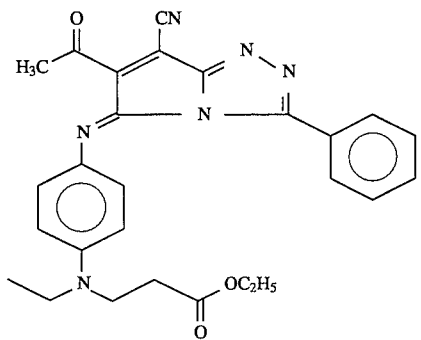 (II-28)
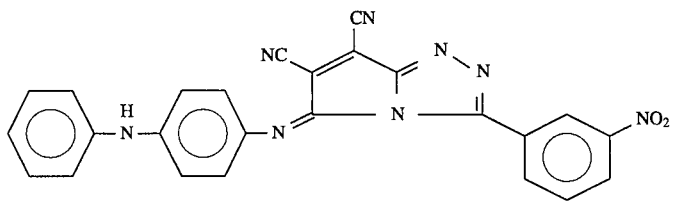 (II-29)
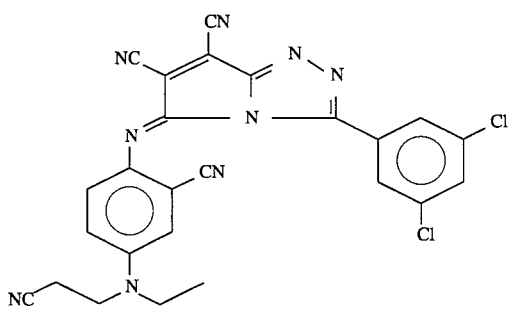 (II-30)
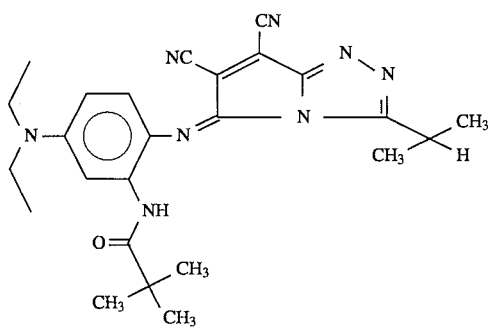 (II-31)
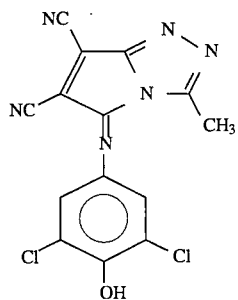 (II-32)

-continued
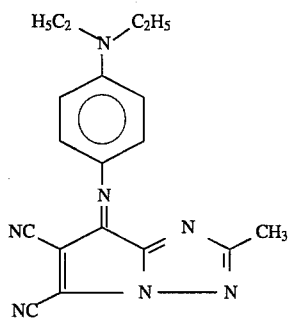
(III-1)
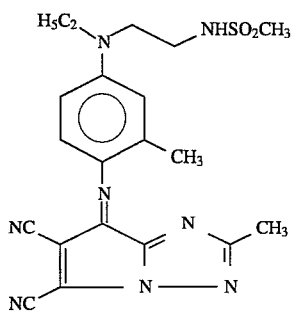
(III-2)
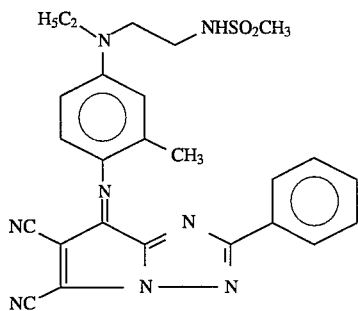
(III-3)
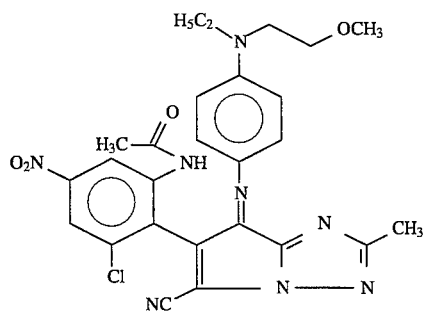
(III-4)
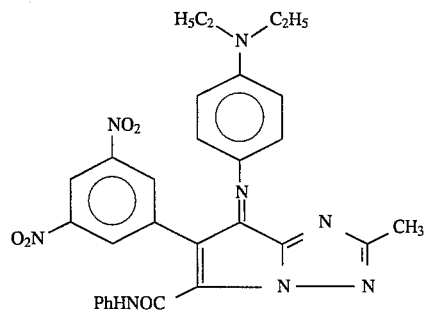
(III-5)

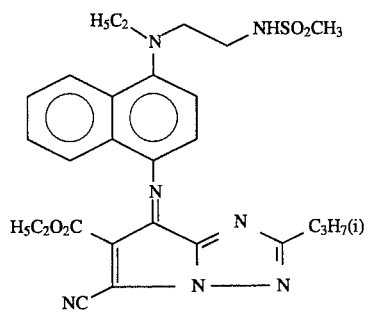
(III-6)
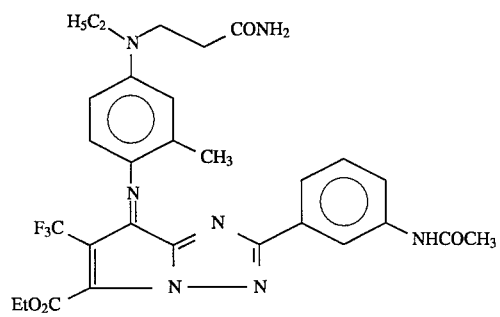
(III-7)
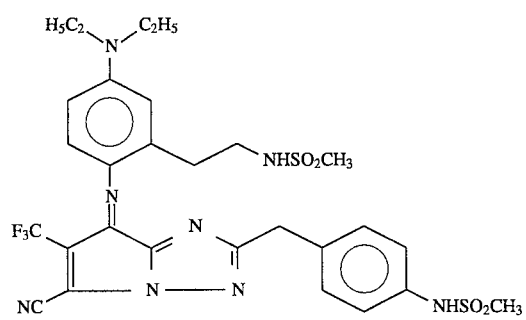
(III-8)
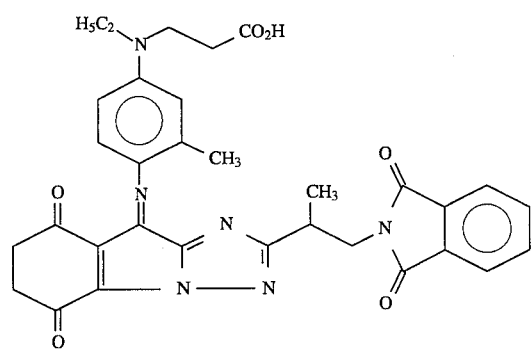
(III-9)
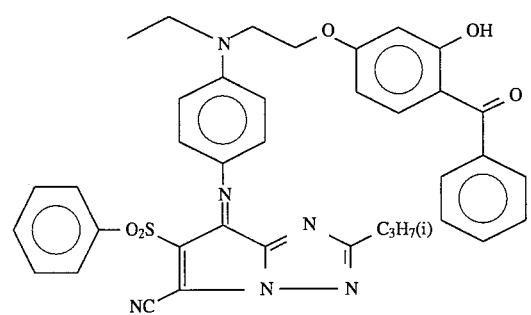
(III-10)

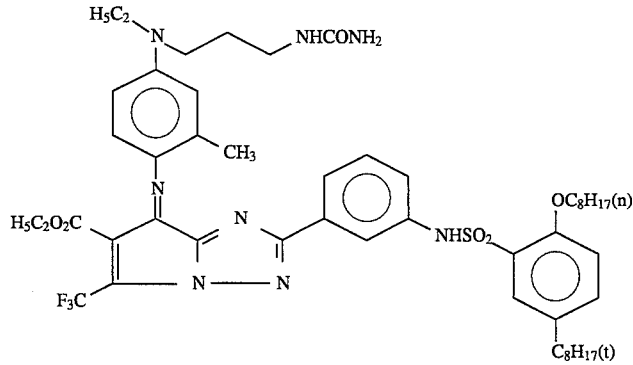
(III-11)
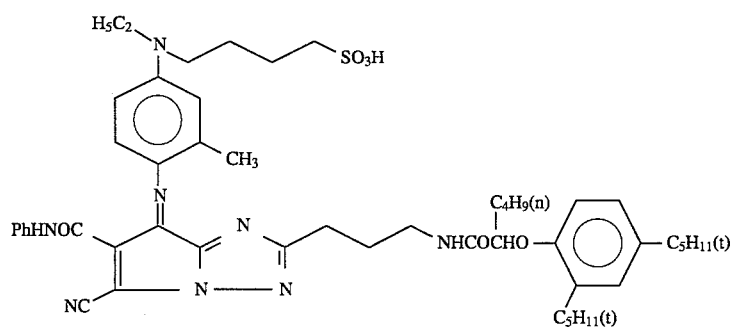
(III-12)
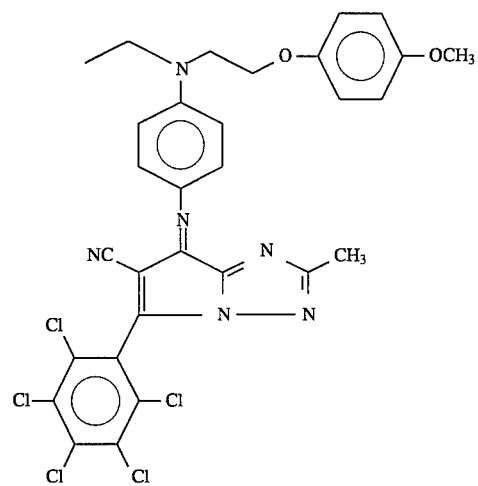
(III-13)
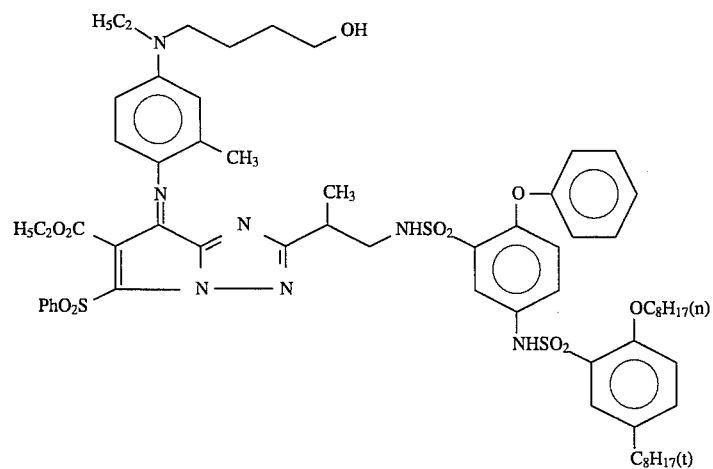
(III-14)

-continued
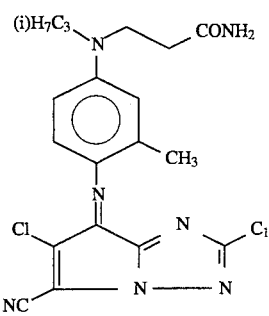
(III-15)
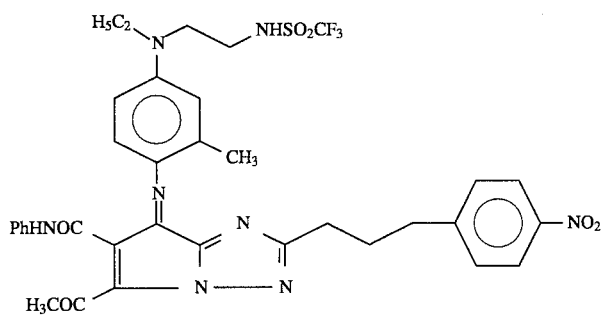
(III-16)
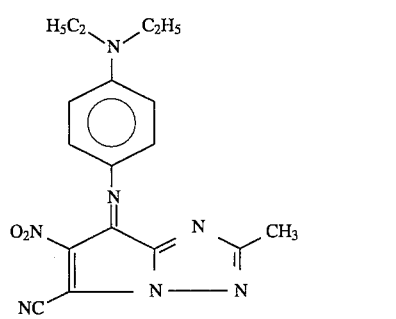
(III-17)
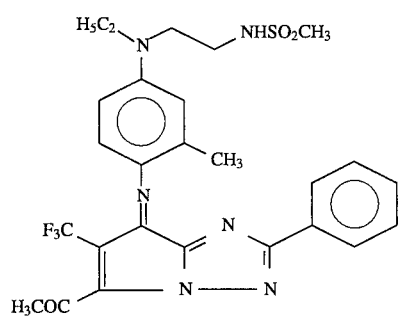
(III-18)
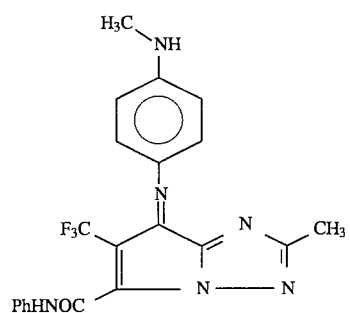
(III-19)

-continued
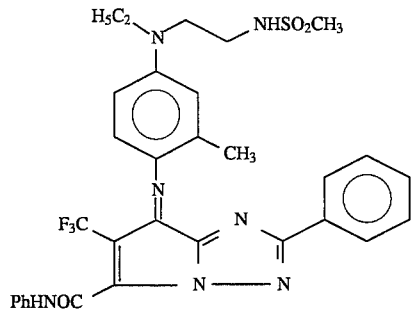 (III-20)
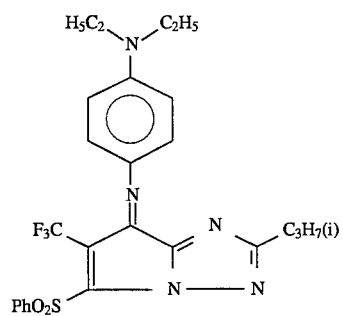 (III-21)
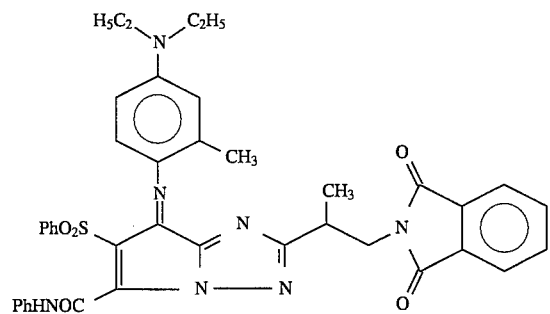 (III-22)
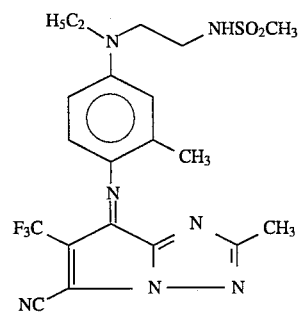 (III-23)
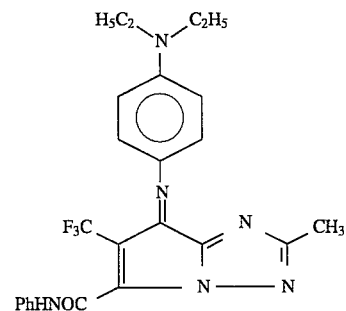 (III-24)

-continued
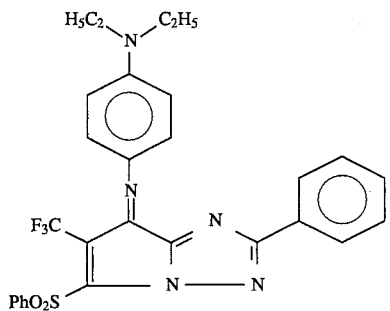
(III-25)
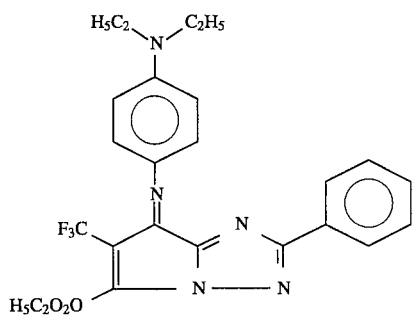
(III-26)
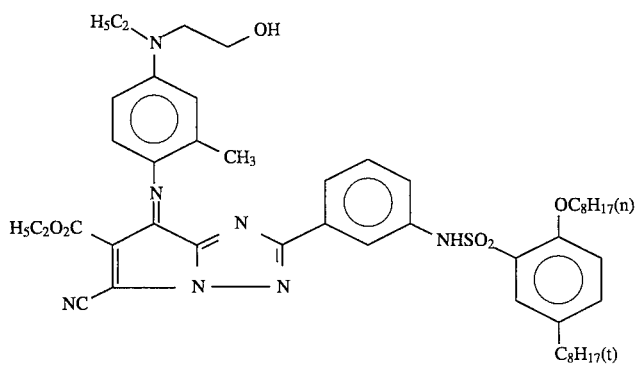
(III-27)
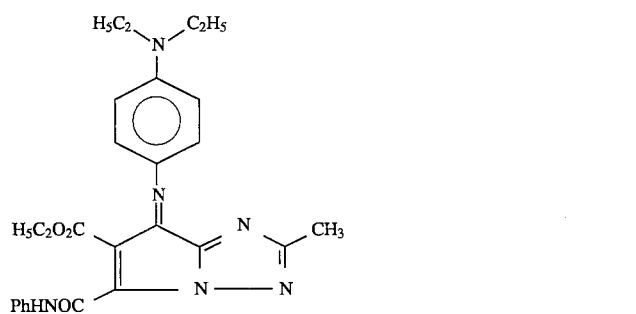
(III-28)
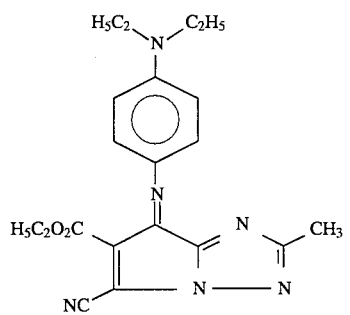
(III-29)

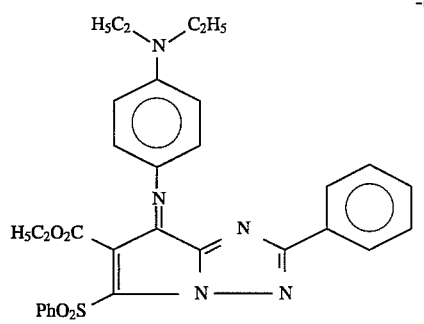
(III-30)
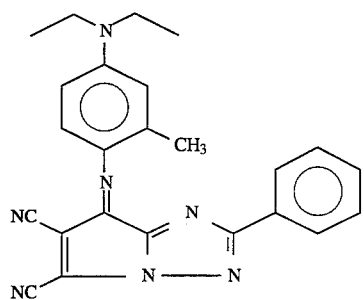
(III-31)
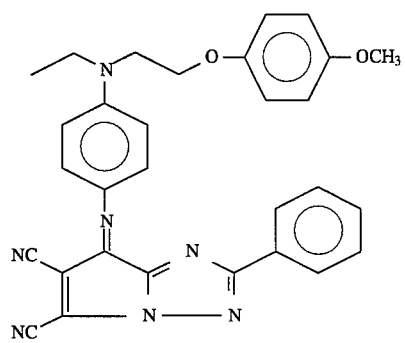
(III-32)
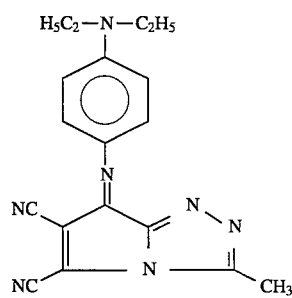
(IV-1)
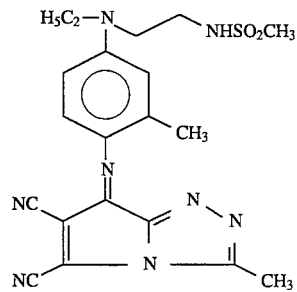
(IV-2)

-continued
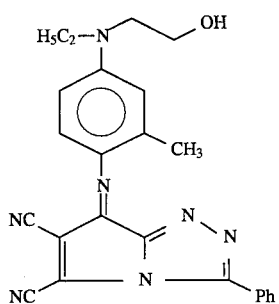
(IV-3)
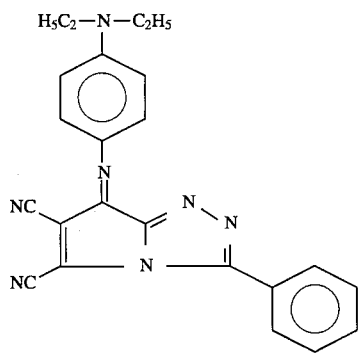
(IV-4)
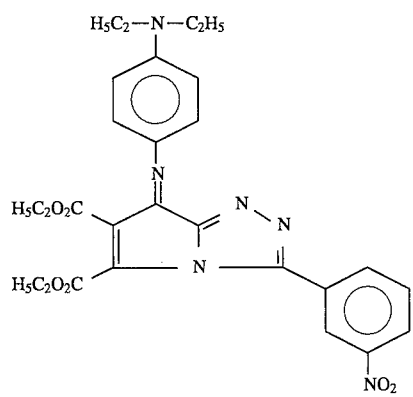
(IV-5)
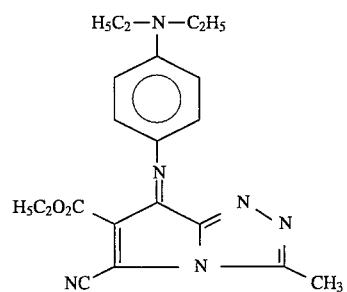
(IV-6)
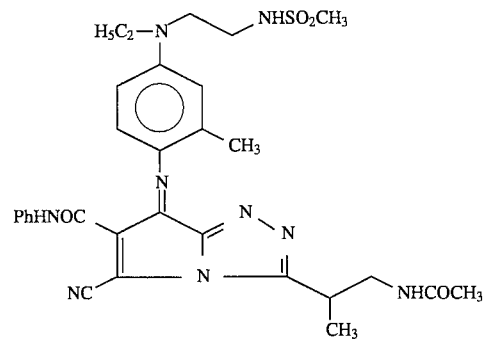
(IV-7)

-continued
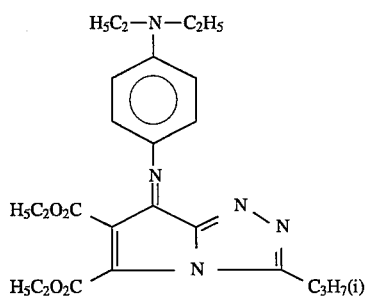 (IV-8)
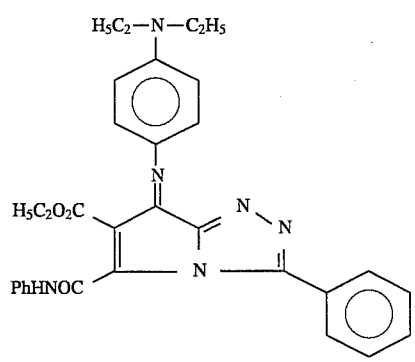 (IV-9)
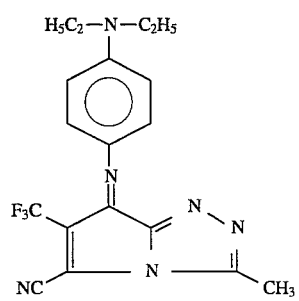 (IV-10)
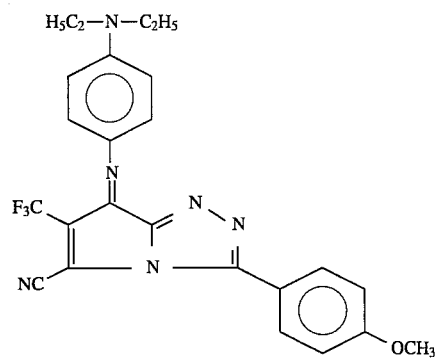 (IV-11)
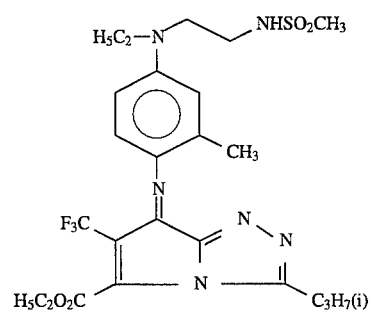 (IV-12)

-continued
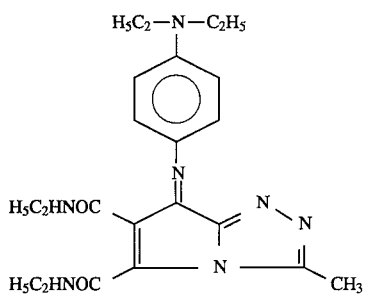
(IV-13)
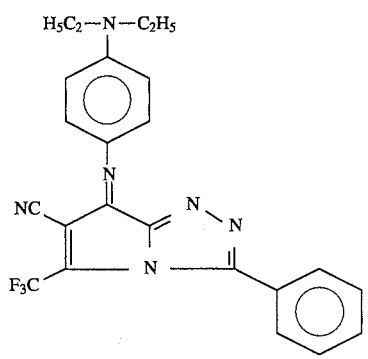
(IV-14)
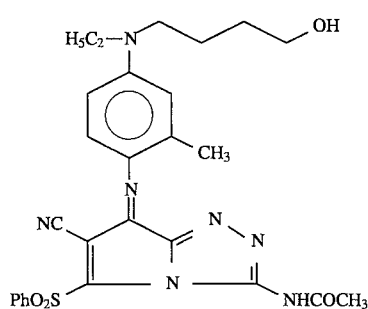
(IV-15)
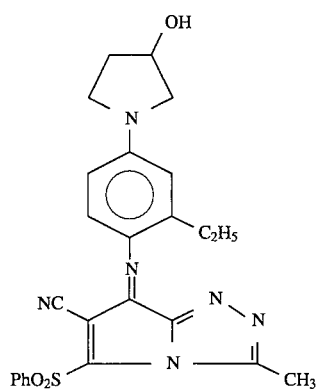
(IV-16)
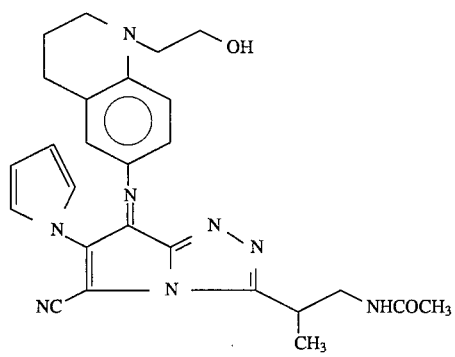
(IV-17)

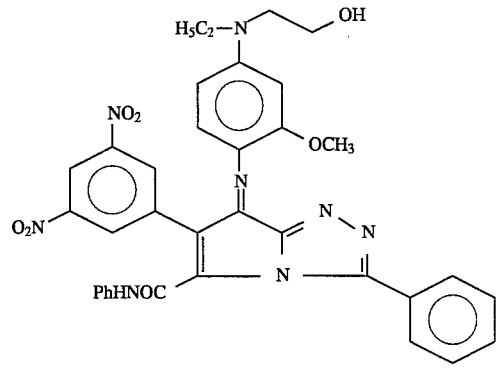
(IV-18)
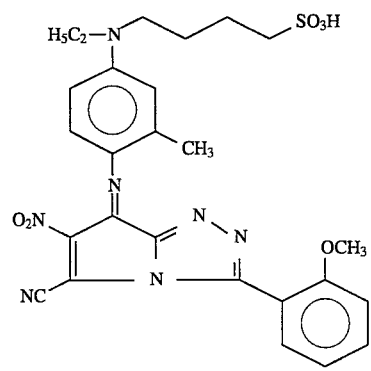
(IV-19)
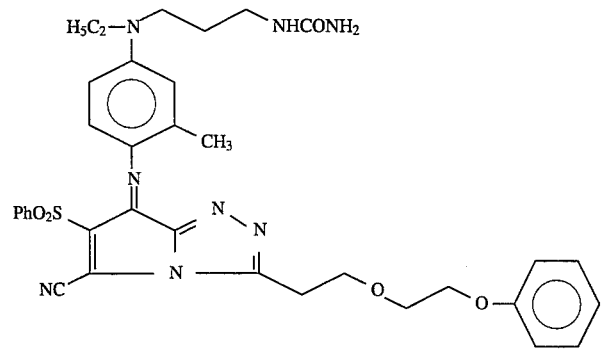
(IV-20)
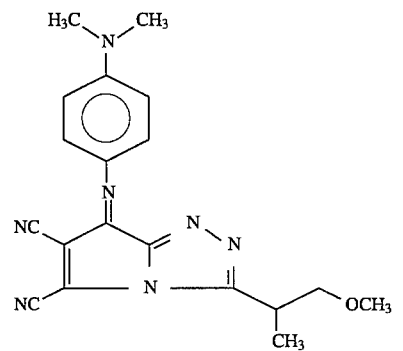
(IV-21)

(IV-22)
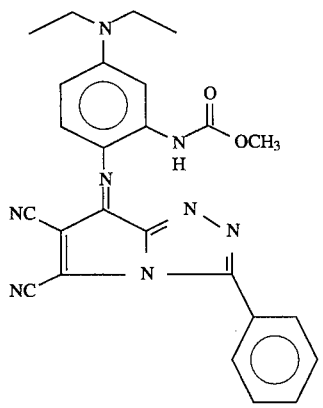
(IV-23)
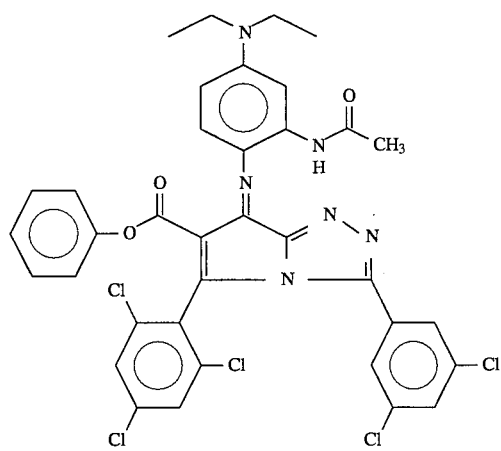
(IV-24)
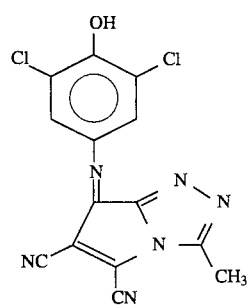
Typical examples of process for the synthesis of the compound represented by formula (V) will be given below.
When $R^7$=COR:
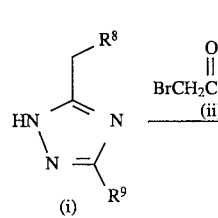
When $R^7$=CN:
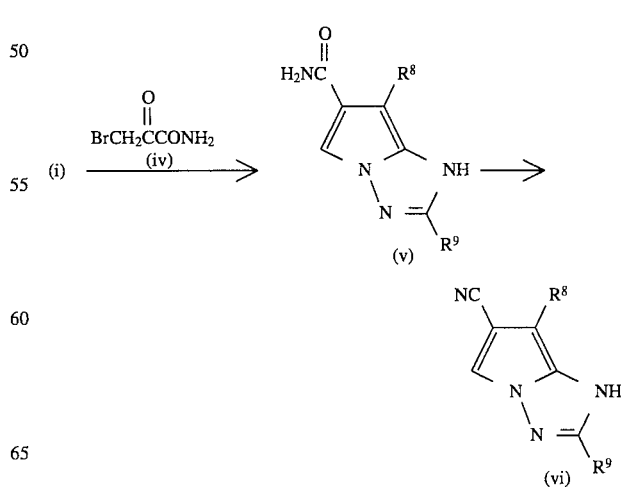

(iii) or (vi) → 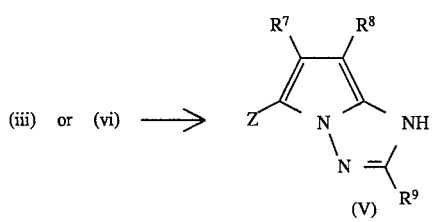

Compound (i) can be synthesized by any known method. For example, synthesis methods as described in *J. C. S.*, 518 (1961), *J. C. S.*, 5149 (1962), *Angew. Chem.*, 72,956 (1960), and *Berichte.*, 97,3436 (1964), and references cited therein, and analogous methods can be used.

The synthesis of Compound (iii) can be accomplished by the nucleophilic displacement reaction from Compound (i) to Compound (ii) and the subsequent cyclization reaction.

In this synthesis, a base such as sodium hydride, triethylamine, diazabicycloundecene, potassium carbonate and sodium carbonate may be preferably used. The reaction may be effected free of solvent or in a solvent such as tetrahydrofuran, acetonitrile, N,N-dimethylformamide, N,N-dimethylacetamide, N,N'-dimethylimidazolidon-2-one, acetone and toluene. The reaction temperature is normally in the range of −20° C. to 150° C., preferably 0° C. to 100° C.

The synthesis of Compound (v) can be accomplished by the nucleophilic displacement reaction from Compound (i) to Compound (iv) and the subsequent cyclization reaction as in the synthesis of Compound (iii).

Compound (vi) is derived by the dehydration reaction of Compound (v). In this reaction, phosphorus oxychloride, phosphorus pentachloride, phosphorus trichloride, etc. may preferably be used. The reaction may be effected free of solvent or in toluene or chloroform. The reaction temperature is normally in the range of −10° C. to 250° C., preferably 20° C. to 200° C.

The compound represented by formula (V) can be synthesized from Compound (iii) or (vi) by a known method.

For example, if an arylthio group or heterocyclic thio group is connected to Compound (V) to obtain a 7-aromatic mercapto or heterocyclic mercapto substituted compound, a method described in U.S. Pat. No. 3,227,554 can be used, i.e., a process can be used which comprises dissolving an arylmercaptan, heterocyclic mercaptan and their disulfides in a halogenated hydrocarbon solvent, treating the solution with chlorine or sulfuryl chloride to produce sulfenyl chloride, and then adding the solution to a solution of Compound (V) in an arotonic polar solvent.

The compounds represented by formulae (I) to (IV) can be synthesized by oxidation coupling of the following Compounds A, B, C and D with the following Compound E:

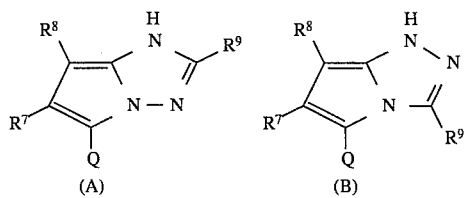

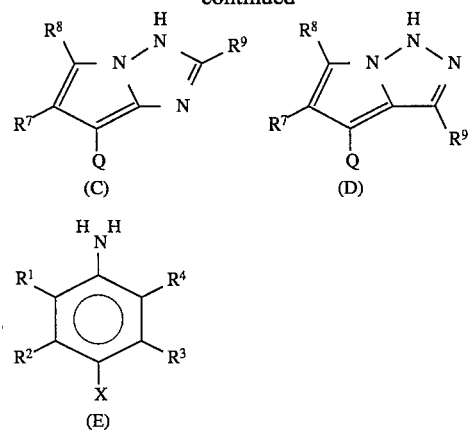

In these formulae, Q represents a hydrogen atom or split-off group which splits off upon coupling reaction, and formula (A) includes formula (V). It goes without saying that Compounds A, B, C and D may be in the form of their tautomers.

Alternatively, the compounds represented by formulae (I) to (IV) can be synthesized by the dehydration condensation of the above mentioned Compounds A, B, C and D with the following Compound F:

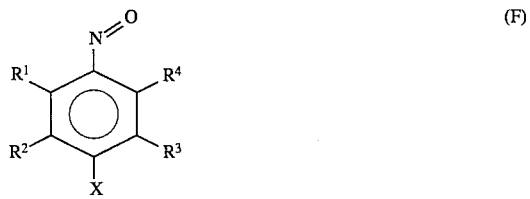

In this case, Q in Compounds A, B, C and D is a hydrogen atom.

For example, the compound represented by formula (I) can be derived from the compound represented by formula (V) by a known method as described in JP-A-63-145281. That is, the compound represented by formula (I) can be synthesized in the presence of a compound represented by formula (V), a phenylenediamine, and an oxidizer.

It is thought that this coupling reaction involves a nucleophilic attack of a coupler anion on quinodimine produced by the oxidation of phenylenediamine to form a leuco dye which is then converted to an azomethine dye as described in T. H. James, *The Theory of the Photographic Process*, 4th ed., Macmillan, 1977. The reaction preferably proceeds under a basic condition. The reaction medium may be any of an organic medium, aqueous organic medium and aqueous solution. If the reaction is effected in a basic aqueous solution, the compound represented by formula (V) may be an oil-in-water dispersion. The oil-in-water dispersion may be present in a hydrophilic colloidal medium such as gelatin. As the oxidizer there may be used any organic or inorganic oxidizer having a potential strong enough to oxidize phenylenediamine. The oxidizer may be used in the form of solution or dispersion in the reaction medium. If Z in formula (V) is a hydrogen atom, phenylenediamine is present in the system in an amount of 0.1 to 10 mol, preferably 0.5 to 2 mol per mol of compound of formula (V), and the oxidizer is used in an amount of at least 4 equivalents, preferably 4.4 to 20 equivalents. If Z is not a hydrogen atom, the compound represented by formula (I) can be synthesized in the same manner as above except that the oxidizer is used in an amount of at least 2 equivalents, preferably 2.2 to 10 equivalents. If the reaction medium is aqueous, coupling may be effected at a pH of 8 or more, preferably 10 to 12. As the oxidizer there can be used silver halide, hydrogen peroxide, manganese dioxide, potassium persulfate, oxygen, or compounds as described in Fieser & Fieser, *Organic Reagents*.

The present invention will be further described in the following examples, but the present invention should not be construed as being limited thereto.

SYNTHESIS EXAMPLE 1

Synthesis of Compound (V-1)

Compound (V-I) was synthesized in the following process:

at a temperature of 0° C. in such a manner that the reaction temperature didn't rise. The reaction system was stirred for hour. 200 ml of a 1 N dilute hydrochloric acid was added to the reaction system. The reaction system was extracted with 300 ml of ethyl acetate three times. The resulting organic phase was washed with water and saturated brine, and then dried over anhydrous sodium sulfate. The solvent was distilled off under reduced pressure. The material was purified through column chromatography (developing solvent: 3:1 mixture of hexane and ethyl acetate) to obtain 7.57 g of Compound (V-1) (yield: 13%).

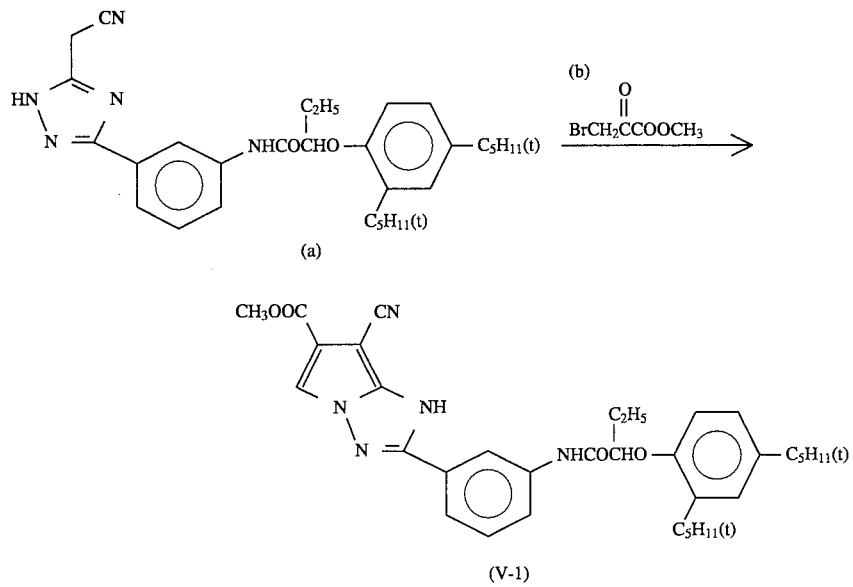

To a solution of Compound (a) (50.1 g; 0.1 mol) and Compound (b) (19.9 g; 0.11 mol) in tetrahydrofuran (300 ml) was added gradually sodium hydride (12.0 g; 0.30 mol)

SYNTHESIS EXAMPLE 2

Synthesis of Compound (V-22)

Compound (V-22) was synthesized in the following process:

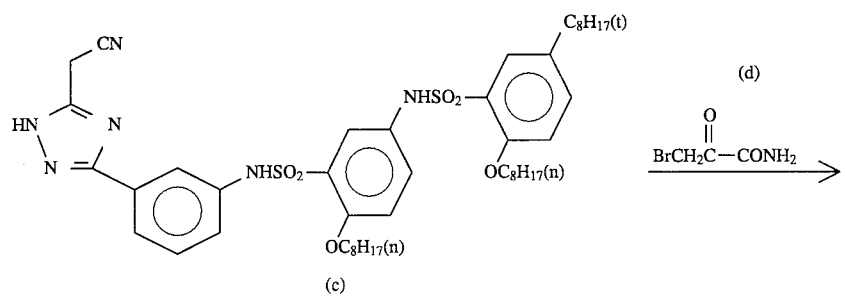

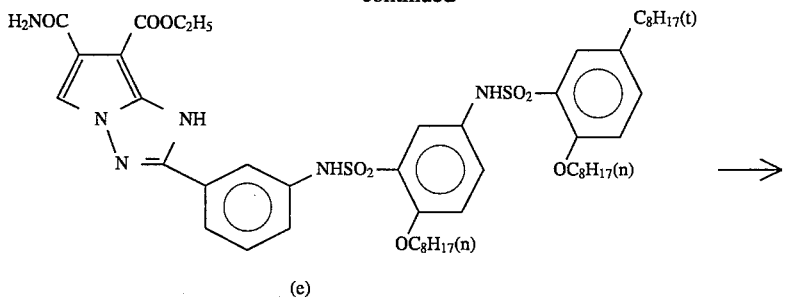

(e)

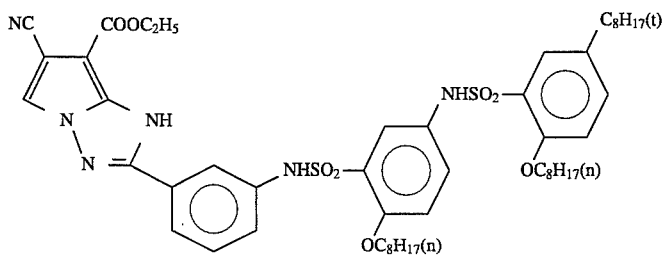

(V-22)

From Compound (c) (45.5 g; 50 mmol) and Compound (d) (9.13 g; 55 mmol) Compound (e) was obtained in the same manner as in Synthesis Example 1 (3.90 g; 8%). To Compound (e) (3.90 g; 4.0 mmol) was added phosphorus oxychloride (1.47 g; 9.6 mmol) at a temperature of 100° C.

The reaction system was stirred for 1 hour. After the reaction system was cooled, 10 cc of water was added thereto. The reaction system was extracted with 30 cc of ethyl acetate three times. The resulting organic phase was washed with saturated brine, and then dried over anhydrous sodium sulfate. The solvent was distilled off under reduced pressure. The material was recrystallized from acetonirile (30 cc) to obtain 3.22 g of Compound (V-22) (yield:84%).

SYNTHESIS EXAMPLE 3

Synthesis of Compound (V-20)

Compound (V-20) was synthesized in the following process:

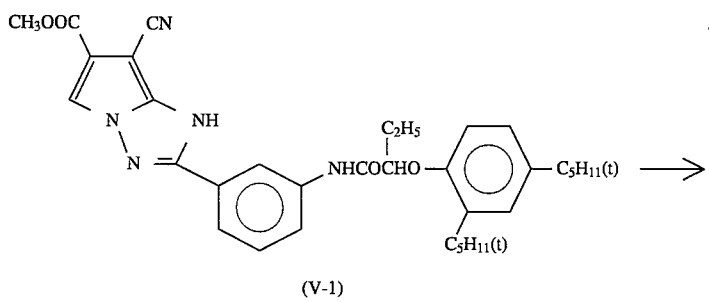

(V-1)

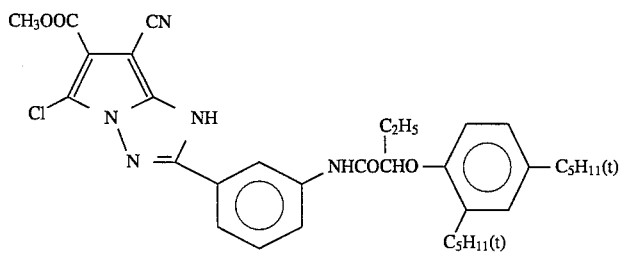

(V-20)

To a solution of Compound (V-1) (2.91 g; 5 mmol) in methylene chloride (30 ml) was added dropwise sulfuryl chloride (0.74 g; 5.5 mmol) at a temperature of 0° C. The reaction system was stirred for 1 hour. Water was added to the reaction system. The reaction system was extracted with 30 cc of methylene chloride three times. The resulting organic phase was washed once with saturated brine, and then dried over anhydrous sodium sulfate. The solvent was distilled off under reduced pressure. The material was recrystallized from acetonirile to obtain 2.83 g of Compound (V-20) (yield: 92%).

SYNTHESIS EXAMPLE 4

Synthesis of Compound (V-21)

Compound (V-21) was synthesized in the following process:

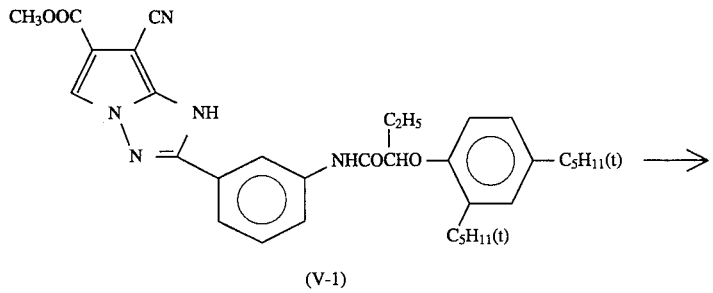

(V-1)

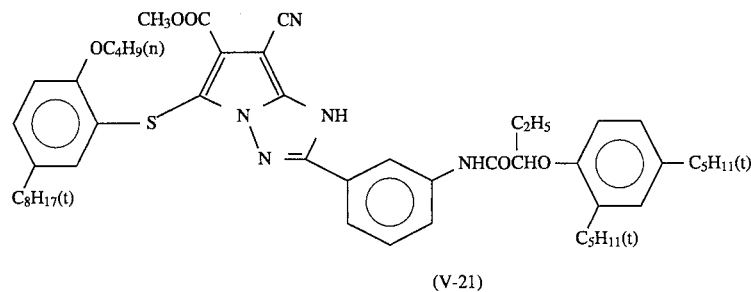

(V-21)

To a solution of di-[(2-n-butoxy-5-t-octyl)phenyl]disulfide (3.53 g; 6 mmol) in methylene chloride (20 ml) was added sulfuryl chloride (1.76 g; 13 mmol) at a temperature of 0° C. The reaction system was stirred for 1 hour. Methylene chloride and sulfuryl chloride were removed under reduced pressure. To the residue was added methylene chloride (20 ml). The solution was added dropwise to a solution of Compound (V-1) (2.91 g; 5 mmol) in N,N-dimethylformamide (10 ml) at a temperature of 0° C. The reaction system was stirred for 1 hour. Water was added to the reaction system. The reaction system was extracted with 30 ml of ethyl acetate twice. The resulting organic phase was washed with water and saturated brine, and then dried over anhydrous sodium sulfate. The solvent was distilled off under reduced pressure. The material was purified through silica gel chromatography (developing solvent: 2:1 mixture of hexane and ethyl acetate) to obtain 2.93 g of Compound (V-21) (yield: 67%).

SYNTHESIS EXAMPLE 5

Synthesis of Compound (V-25)

Compound (V-25) was synthesized in the following process:

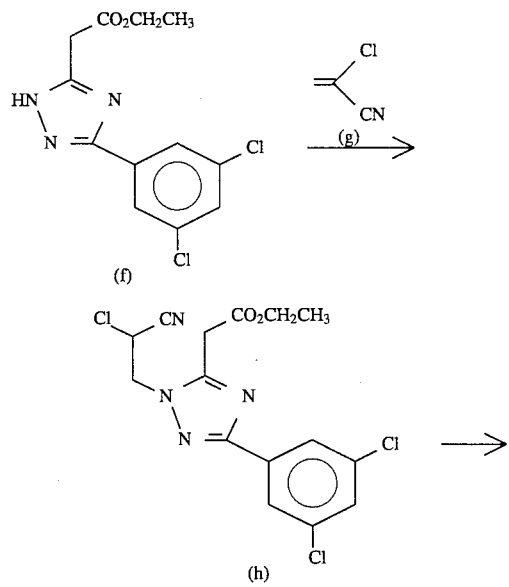

-continued

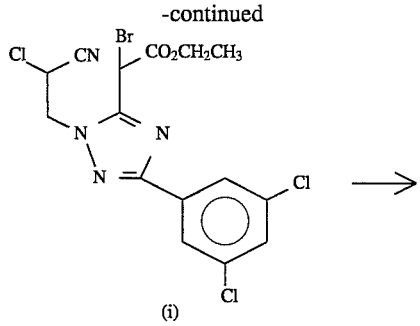

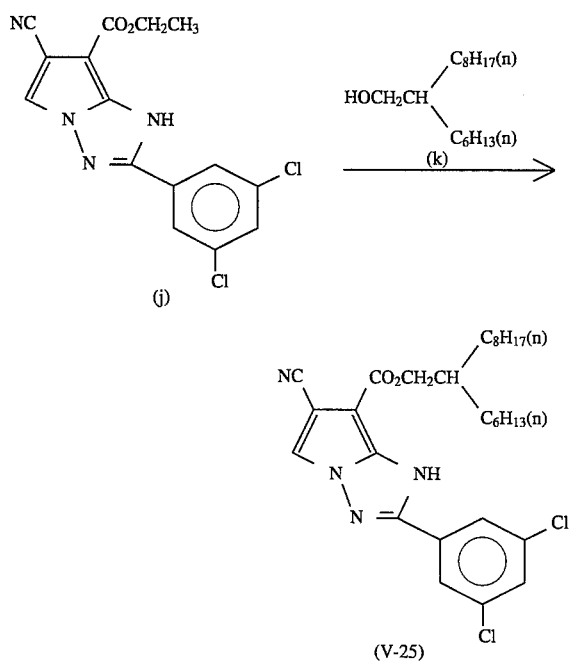

30.0 g of Compound (f) and 11.4 g of Compound (g) were dissolved in 300 ml of tetrahydrofuran. 6.0 ml of tetramethyl guanidine was added to the solution. The material was stirred at room temperature for 5 hours. 500 ml of ethyl acetate was added to the material. The material was then washed with water. The ethyl acetate was dried, and then distilled off. The material was then crystallized from methanol to obtain 27.5 g of Compound (h).

27.4 g of Compound (h) thus obtained was dissolved in 270 ml of tetrahydrofuran. 13.6 g of bromine was gradually dropwise added to the solution under cooling with ice. The material was stirred for 5 hours. 500 ml of ethyl acetate was added to the material. The material was then washed with water until it turned neutral. The resulting ethyl acetate phase was dried, and then distilled off. The residue was purified through column chromatography to obtain 28.0 g of Compound (i).

28.0 g of Compound (i) thus obtained was dissolved in 170 ml of tetrahydrofuran. 9.6 g of 60% sodium hydride was gradually added to the material while the reaction temperature was kept at −10° C. After the completion of the reaction, ethyl acetate was added to the reaction system. The material was then washed with water. The resulting ethyl acetate phase was dried, and then distilled off. The material was purified through column chromatography to obtain 3.0 g of Compound (j).

1.8 g of Compound (j) thus obtained and 12.4 g of Compound (k) were dissolved in 2.0 ml of sulfolane. To the solution was further added 1.5 g of titanium isopropoxide. The reaction system was then allowed to undergo reaction for 1.5 hours while the reaction temperature was kept at 110° C. Ethyl acetate was then added to the material. The material was then washed with water. The resulting ethyl acetate phase was dried, and then distilled off. The residue was then puridied through column chromatography to obtain 1.6 g of Compound (V-25).

The melting point of Compound (V-25) was 97° to 98° C.

SYNTHESIS EXAMPLE 6

Synthesis of Dye of Compound (V-20)

To a solution of Compound (V-20) (9.59 g; 10.0 mmol) in 100 ml of a 1:1 mixture of ethyl acetate and ethanol was added 40 ml of an aqueous solution of sodium carbonate (9 g). Subsequently, 4-(N-ethyl-N-(2-methanesulfonamidoethyl)amino)-2-methylaniline sulfate (6.38 g; 12.2 mmol) was added to the system. The material was then stirred at room temperature for 5 hours. To the material was then added dropwise 20 ml of an aqueous solution of ammonium persulfate (4.5 g). The material was then stirred for 1 hour. The material was then extracted with ethyl acetate three times. The resulting organic phase was washed with saturated aqueous solution of sodium chloride, and then dried over anhydrous sodium sulfate. The solvent was then distilled off under reduced pressure. The material was then purified through column chromatography (developing solvent: 20:1 mixture of methylene chloride and methanol). The material was then recrystallized from methanol to obtain 10.2 g of a dye of Compound (V-20) (yield: 83%).

SYNTHESIS EXAMPLE 7

Synthesis of Compound (I-2)

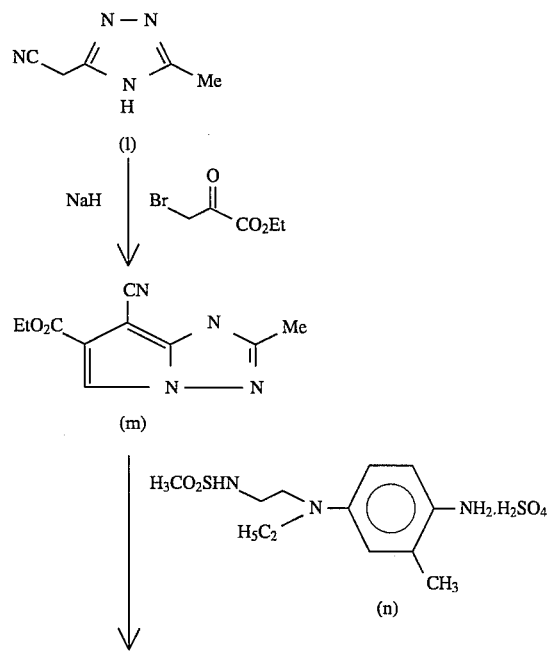

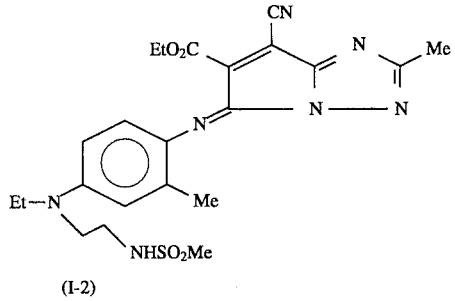

(I-2)

1.5 g of 3-cyanomethyl-5-methyl-1,2,4-triazole (Compound (l)) was dissolved in 30 ml of tetrahydrofuran. To the solution was added 1.0 g (24.6 mmol) of sodium hydride (60% in oil). The material was then heated to a temperature of 50° C. To the material was added 1.9 ml (14.7 mmol) of ethyl bromopyruvate. The material was further heated under reflux for 2 hours. The material was then cooled to room temperature. To the material were then added brine and 2 N hydrochloric acid solution to acidify the solution. The material was extracted with ethyl acetate twice, and then dried. Ethyl acetate was then distilled off under reduced pressure. The residue was then purified through silica gel chromatography to obtain 1.20 g of Compound (m) (yield: 45%).

The synthesis of Compound (l) was accomplished by a method described in *Journal of the Chemical Society*, 5149 (1962).

To 1.0 g of Compound (m), 20 cc of ethyl acetate, 20 cc of ethanol, 24 cc of water, 6.6 g of sodium carbonate and 3.1 g of Compound (n) was added a solution of 4.6 g of ammonium persulfate in 5 cc of water with stirring.

The reaction system was then allowed to undergo reaction at a temperature of 20° C. for 1 hour. The material was then extracted with ethyl acetate. The resulting organic phase was washed with water twice, and then dried over magnesium sulfate. After filtration, the solvent was distilled off. The resulting crude crystal was purified through silica gel chromatography, and then recrystallized from methanol to obtain 0.82 g of Compound (I-2) (yield: 37%; m.p. 223° to 224° C.)

The absorption characteristics of Compound (I-2) of the present invention in a solvent are shown in FIG. 1 together with those of Comparative Dye a.

In FIG. 1, the solid line indicates the absorption characteristics of Compound (I-2) of the present invention, and the broken line indicates the absorption characteristics of Comparative Dye a.

The maximum absorption wavelength (λmax) and half-value width of Compound (I-2) of the present invention and Comparative Dye a are set forth below.

Compound (I-2) of the present invention

λmax: 602.3 nm (in ethyl acetate)

Half-value width: 94.9 nm

Comparative Dye

λmax: 562.6 nm (in ethyl acetate)

Half-value width: 88.1 nm

As the comparative dye there was used Comparative Dye a shown below:

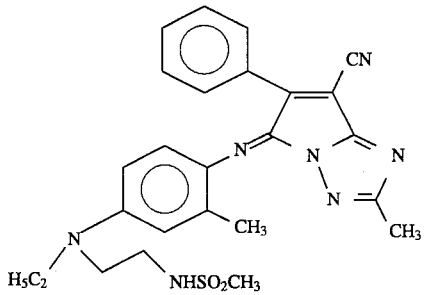

FIG. 1 shows that the dye of the present invention exhibits a sharp absorption, a reduced undesirable absorption in the yellow portion and a maximum absorption suitable as cyan dye.

On the other hand, it is shown that Comparative Dye a wherein the substituent $R^7$ in the coupler portion is a phenyl group ($\sigma_p$ is smaller than 0.15) doesn't exhibit cyan color.

The maximum absorption wavelength (λmax) of other exemplary compounds of the present invention in ethyl acetate are set forth below:

Compound (I-22): 618 nm

Compound (I-4): 606 nm

Compound (I-7): 619 nm

Compound (I-10): 616 nm

SYNTHESIS EXAMPLE 8

Synthesis of Compound (II-2)

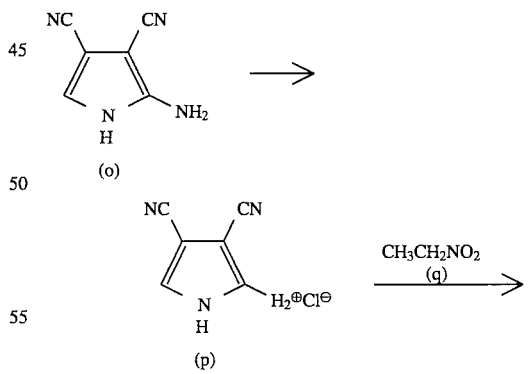

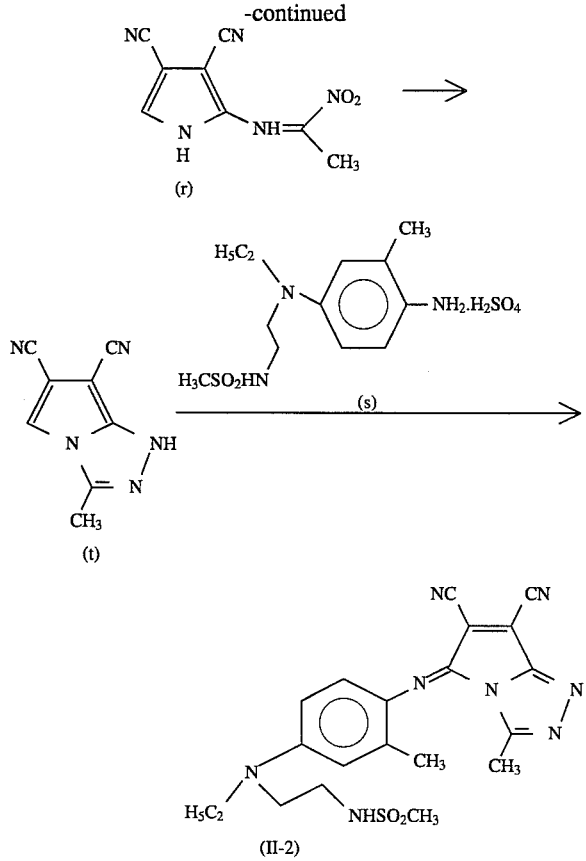

To 2.50 g (18.9 mmol) of 2-amino-3,4-dicyanopyrrole (Compound (o)) was added 15.8 ml of 36% hydrochloric acid. To the material was then added dropwise a solution of 1.44 g (20.8 mmol) of sodium sulfite in 2.9 ml of water with stirring under cooling with ice in 15 minutes. The mixture was further stirred for 30 minutes. The thus obtained solution containing Compound (p) was later used as Solution (1).

9.08 g (227.0 mmol) of sodium hydroxide was dissolved in a mixture of 50 ml of ethanol and 25 ml of water. To the solution was added 2.7 ml (3.78 mmol) of nitroethane (Compound (q)) with stirring under cooling with ice. The material was further stirred for 30 minutes. To the reaction solution was added dropwise Solution (1) in 20 minutes. The reaction solution was further stirred for 2 hours. Ethanol was distilled off under reduced pressure. 19 ml of 2 N hydrochloric acid was then added to the reaction solution so that the pH thereof reached about 5. To the reaction solution were added water and sodium chloride. The reaction solution was extracted with ethyl acetate twice. The reaction solution was washed with saturated brine, and then dried over Glauber's salt. Ethyl acetate was then distilled off under reduced pressure. (Synthesis of Compound (r))

The resulting residue was dissolved in 30 ml of ethanol. To the solution was added 4.2 ml (20.8 mmol) of 28% sodium methylate. The material was then heated under reflux for 2.5 hours. Ethanol was then distilled off under reduced pressure. To the resulting residue was added brine. The solution was extracted with ethyl acetate twice. The solution was dried over Glauber's salt. Ethyl acetate was distilled off under reduced pressure. The residue was then purified through silica gel chromatography to obtain 1.23 g (yield: 38%) of Compound (s).

The synthesis of Compound (o) was accomplished by nitrating 3,4-dicyanopyrrole synthesized according to a method described in *Tetrahedron Letters*, 5337 (1972), and then reducing the material with iron.

To 1.0 g of Compound (s), 20 cc of ethyl acetate, 20 cc of ethanol, 24 cc of water, 5.2 g of sodium carbonate and 2.4 g of Compound (t) was added a solution of 3.6 g of ammonium persulfate in 5 cc of water.

The reaction system was allowed to undergo reaction at a temperature of 20° C. for 1 hour. The reaction system was extracted with ethyl acetate. The resulting organic phase was washed with water twice, dried over magnesium sulfate, and then filtered. The solvent was then distilled off. The residue was then purified through silica gel chromatography to obtain 1.12 g of Compound (II-2) (yield: 44%).

m.p. (decomposed to black at 241° C.)

The absorption characteristics of Compound (II-2) of the present invention in a solvent are shown in FIG. 2 together with those of Comparative Dye b.

In FIG. 2, the solid line indicates the absorption characteristics of Compound (II-2) of the present invention, and the broken line indicates the absorption characteristics of Comparative Dye b.

The maximum absorption wavelength (λmax) and half-value width of Compound (II-2) of the present invention and Comparative Dye b are set forth below.

Compound (II-2) of the present invention

λmax: 641.0 nm (in ethyl acetate)

Half-value width: 79.7 nm

Comparative Dye max: 644.3 nm (in ethyl acetate)

Half-value width: 117.8 nm

As the comparative dye there was used Comparative Dye b shown below:

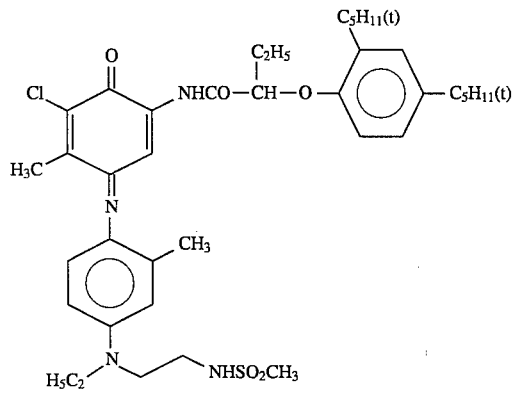

FIG. 2 shows that the dye of the present invention exhibits a sharp absorption, a reduced undesirable absorption in the yellow portion and a maximum absorption suitable as cyan dye.

On the other hand, it is shown that Comparative Dye b exhibits a greater half-value width and thus a broader absorption.

The maximum absorption wavelength (λmax) of other exemplary compounds of the present invention in ethyl acetate are set forth below:

Compound (II-1): 639 nm

Compound (II-4): 653 nm

Compound (II-10): 624 nm

Compound (II-17): 629 nm
Compound (II-24): 639 nm

SYNTHESIS EXAMPLE 9

Synthesis of Compound (II-25)

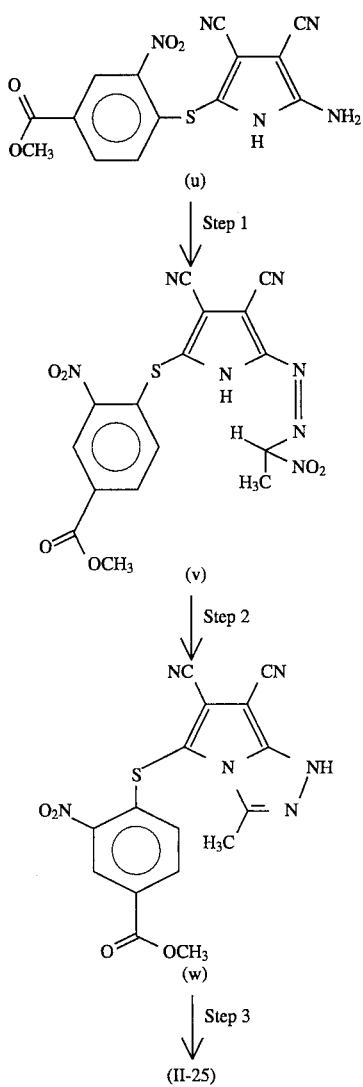

Step 1:

To 10 g of Compound (u), 30 ml of ethanol and 29.5 g of concentrated hydrochloric acid was added 2.2 g of sodium sulfite with stirring at a temperature of 5° C. The reaction mixture was further stirred for 2 hours to prepare a diazo solution of Compound (u).

4.37 g of nitroethane, 14.0 g of sodium hydroxide, 100 ml of ethanol and 50 ml of water were stirred at a temperature of 5° C. for 30 minutes. To the solution was added dropwise the diazo solution of Compound (u). The reaction solution turned red. The reaction solution was then allowed to undergo reaction for 30 minutes. To the reaction solution were added 100 ml of water and concentrated hydrochloric acid in a proper amount so that the pH thereof reached 2. As a result, a red crystal was deposited. The crystal was filtered off, washed with water, and then dried to obtain 11.0 g of Compound (v) (yield: 95.5%).

Step 2:

10.0 g of Compound (v), 500 ml of methanol and 5.1 g of 28 wt. % sodium methylate were stirred at a temperature of 15° C. for 5 hours. To the solution was added concentrated hydrochloric acid so that the pH thereof reached 2. The resulting crystal was filtered off, washed with water, and then dried to obtain 3.5 g of Compound (w) (yield: 38.2%).

Step 3:

To 2.5 g of Compound (w), 100 ml of methylene chloride and 4.6 ml of triethylamine were added alternately 1.28 g of imide N-bromosuccinate and 1.89 g of N,N-diethyl-p-phenylenediamine sulfate with stirring at a temperature of 20° C. The reaction system was then allowed to undergo reaction for 30 minutes. The reaction system was checked by thin layer chromatography. Compound (w) all disappeared. The reaction system were extracted with 500 ml of water and 500 ml of ethyl acetate, separated, dried, and then concentrated.

The concentrate was then purified through silica gel chromatography to obtain 0.50 g of Compound (II-25) (yield: 23.1%).

The compound thus obtained exhibited a maximum absorption wavelength of 636 nm with a half-value width of 84 nm in ethyl acetate.

The heat migrating dye of the present invention is incorporated in a dye providing layer on a support to form a heat transfer dye providing material which is used for the image formation in the heat transfer recording process.

The use of the heat migrating dye of the present invention in the image formation in the heat transfer recording process will be further described hereinafter.

In order to form a multi-color image, three color dyes, i.e., yellow, magenta and cyan dyes are needed.

The compound of the present invention can be used as cyan dye and two other color dyes can be selected from known dyes to form a full color image.

For the same color, a dye of the present invention and known dyes may be used in admixture. Two or more kinds of dyes of the present invention can be used in admixture as the same color dye.

The use of the heat migrating dye of the present invention will be described hereinafter.

The heat transfer dye providing material can be used in the form of sheet, continuous roll or ribbon. The cyan dye of the present invention and magenta, yellow and other dyes to be used in combination therewith are normally located on a support in such an arrangement that they each form an independent region. For example, a yellow dye region, a magenta dye region and a cyan dye region may be sequentially horizontally or vertically laminated on a support. Alternatively, the above mentioned yellow dye, magenta dye and cyan dye may be provided on separate supports to prepare three kinds of heat transfer dye providing materials from which dyes are sequentially heat-transferred to one heat transfer image-receiving material.

The cyan dye of the present invention and magenta and yellow dyes to be used in combination therewith can be coated on a support in the form of solution or dispersion in a proper solvent with a binder resin or can be printed on a support by a printing process such as gravure coating process. The dry thickness of the dye providing layer containing these dyes is normally set to the range of about 0.2 to 5 μm, particularly 0.4 to 2 μm.

The coated amount of the heat migrating dye is preferably in the range of 0.03 to 1.0 g/m$^2$, particularly 0.1 to 0.6 g/m$^2$.

As the binder resin to be used in combination with the above mentioned dye there can be selected any binder resin known for such a purpose which normally exhibits a high heat resistance and doesn't inhibit the migration of the dye on heating. Examples of such a binder resin include polyamide resin, polyester resin, epoxy resin, polyurethane resin, polyacrylic resin (e.g., polymethyl methacrylate, polyacrylamide, polystyrene-2-acrylonitrile), vinyl resin such as polyvinyl pyrrolidone, polyvinyl chloride resin (e.g., vinyl chloride-vinyl acetate copolymer), polycarbonate resin, polystyrene, polyphenylene oxide, cellulose resin (e.g., methyl cellulose, ethyl cellulose, carboxymethyl cellulose, cellulose acetate hydrogen phthalate, cellulose acetate, cellulose acetate propionate, cellulose acetate butyrate, cellulose triacetate), polyvinyl alcohol resin (e.g., partially-saponified polyvinyl alcohol such as polyvinyl alcohol, polyvinyl acetal and polyvinyl butyral), petroleumresin, rosin derivative, coumarone-indene resin, terpene resin, and polyolefin resin (e.g., polyethylene, polypropylene).

In the present invention, such a binder resin may be preferably used in the amount of about 20 to 600 parts by weight based on 100 parts by weight of dye.

In the present invention, as an ink solvent for dissolving or dispersing the above mentioned dye and binder resin therein there can be used a known ink solvent.

As the support for the heat transfer dye providing material there can be used any known material. Examples of such a material include polyethylene terephthalate, polyamide, polycarbonate, glassine paper, capacitor paper, cellulose ester, fluoropolymer, polyether, polyacetal, polyolefin, polyimide, polyphenylene sulfide, polypropylene, polysulfone, and cellophane.

The thickness of the support for the heat transfer dye providing material is normally in the range of 2 to 30 µm.

In order to prevent the heat head from sticking to the dye providing material, a slipping layer may be provided. The slipping layer comprises a lubricating substance containing or free of polymer binder such as surface active agent, solid or liquid lubricant or mixture thereof.

In order to prevent the heat head from sticking to the dye providing material due to heat and provide better slipperiness when printed on its back side, the dye providing material is preferably subjected to anti-sticking treatment on the side opposite the dye providing layer.

For example, a heat-resistant slipping layer comprising (1) a reaction product of polyvinyl butyral resin and isocyanate, (2) an alkali metal salt or alkaline earth metal salt of phosphoric ester, and (3) a filler is preferably provided. As such a polyvinyl butyral resin there can be preferably used such a resin having a molecular weight of 60,000 to 200,000 and a glass transition point of 80° C. to 110° C. or such a resin whose vinyl butyral portion is in the proportion of 15 to 40% by weight in the light of the number of sites of reaction with isocyanate. As the alkaline metal salt or alkaline earth metal salt of phosphoric ester there can be used Gafac RD720 produced by Toho Chemical Industry Co., Ltd. Such a material is used in an amount of 1 to 50% by weight, preferably 10 to 40% by weight based on the weight of polyvinyl butyral resin.

The heat-resistant slipping layer preferably exerts its heat resisting effect upon its underlayers. Such a heat-resistant slipping layer can be formed by coating a combination of a thermosetting synthetic resin and its hardener such as combination of polyvinyl butyral and polyhydric isocyanate, combination of acrylic polyol and polyhydric isocyanate, combination of cellulose acetate and titanium chelating agent and combination of polyester and organic titanium compound.

The dye providing material may optionally comprise a hydrophilic barrier layer for preventing the dye from diffusion toward the support. The hydrophilic dye barrier layer comprises a hydrophilic substance useful for the intended purpose. In general, excellent results can be obtained by the use of gelatin, poly(acrylamide), poly(isopropylacrylamide), butyl methacrylate graft gelatin, ethyl methacrylate graft gelatin, cellulose monoacetate, methyl cellulose, poly(vinyl alcohol), poly(ethyleneimine), poly(acrylic acid), mixture of poly(vinyl alcohol) and poly(vinyl acetate), mixture of poly(vinyl alcohol) and poly(acrylic acid), or mixture of cellulose monoacetate and poly(acrylic acid). Particularly preferred among these hydrophilic substances are poly(acrylic acid), cellulose monoacetate, and poly(vinyl alcohol).

The dye providing material may comprise a subbing layer. In the present invention, any subbing layer which exerts the desired effects can be used. Specific preferred examples of such a material include acrylonitrile/vinylidene chloride/acrylic acid copolymer (weight proportion: 14:80: 6), butyl acrylate/2-aminoethyl methacrylate/2-hydroxyethyl methacrylate copolymer (weight proportion: 30:20:50), linear/saturated polyester such as Bostik 7650 (Emheart, Bostik Chemical Group), and chlorinated high-density poly(ethylenetrichloroethylene) resin. The coated amount of the subbing layer is not specifically limited but is normally in the range of 0.1 to 2.0 g/m$^2$.

In accordance with the present invention, heat energy is applied by a heating means such as heat head to a lamination of the heat transfer dye providing material and the heat transfer image-receiving material on either side, preferably on the back side of the heat transfer dye providing material depending on the image data. In this manner, the dye on the dye providing layer can be transferred to the heat transfer image-receiving material depending on the magnitude of heating energy to obtain a color image with excellent sharpness and high definition and gradation. A discoloration inhibitor can be similarly transferred.

The heating means is not limited to heat head. For example, known means such as laser (e.g., semiconductor laser), infrared flash and heat pen can be used.

In the case where laser is used as the heat source, the heat transfer dye providing material may preferably comprise a material which strongly absorbs laser. When the heat transfer dye providing material is irradiated with laser, the laser-absorbing material converts the light energy to a heat energy which is then transferred to the nearest dye until it is heated to a temperature high enough to cause it to migrate to the heat transfer dye providing material.

The laser-absorbing material may be present under the dye in a layer form and/or mixed with the dye.

This process is further described in British Patent 2,083, 726A.

As the above mentioned laser there can be used various lasers such as ion gas laser (e.g., argon, krypton), metallic vapor laser (e.g., copper, gold, cadmium), solid laser (e.g., ruby, YAG), or semiconductor laser which emits light in the infrared range of 750 nm to 870 nm (e.g., Ga-As).

Preferred among these lasers is semiconductor laser in the light of size, cost, stability, reliability, durability and ease of modulation.

Specific examples of semiconductor laser include Laser Model SDL-2420-H2 (trademark) produced by Spectrodiode Labs, and Laser Model SLD-304v/w (trademark) produced by Sony Corporation.

In the present invention, the heat transfer dye providing material can be combined with a heat transfer image-receiving material to give application in printing or facsimile using various heat printers or image printing or printing image from television or CRT screen by magnetic recording process, magneto-optical recording process, photo recording process, etc.

For the details of heat transfer recording process, reference can be made to JP-A-60-34895.

The heat transfer image-receiving material to be used in combination with the heat transfer dye providing material of the present invention comprises on a support an image-receiving layer for receiving a dye which has migrated from the dye providing material. The image-receiving layer is preferably a film having a thickness of about 0.5 to 50 μm containing singly, or in combination with other binder substances, a heat migrating dye-receiving substance which receives and is dyed with a heat migrating dye that has migrated from the heat transfer dye providing material upon printing. Examples of polymers as typical examples of such a heat migrating dye-receiving substance include the following resins:

(a) Resins having ester bond

Examples of such resins include polyester resins obtained by the condensation of dicarboxylic component such as terephthalic acid, isophthalic acid and succinic acid (these dicarboxylic acid components may be substituted by sulfonic acid group, carboxyl group, etc.) with ethylene glycol, diethylene glycol, propylene glycol, neopentyl glycol, bisphenol A, or the like, polyacrylic ester resins or polymethacrylic ester resins such as polymethyl methacrylate, polybutyl methacrylate, polymethyl acrylate and polybutyl acrylate, polycarbonate resins, polyvinyl acetate resins, styrene acrylate resins, and vinyl toluene acrylate resins. Specific examples of these resins include those described in JP-A-59-101395, JP-A-63-7971, JP-A-63-7972, JP-A-63-7973, and JP-A-60-294862. As commercially available resins there can be used Vylon 290, Vylon 200, Vylon 280, Vylon 300, Vylon 103, Vylon GK-140, and Vylon GK-130 produced by Toyobo Co., Ltd., and ATR-2009 and ATR-2010 produced by Kao Corporation.

(b) Resins having urethane bond

Polyurethane resins, etc.

(c) Resins having amido bond

Polyamide resins, etc.

(d) Resins having urea bond

Urea resins, etc.

(e) Resins having sulfone bond

Polysulfone resins, etc.

(f) Resins having high polarity bond

Polycaprolactone resins, styrene-maleic anhydride resins, polyvinyl chloride resins, polyacrylonitrile resins, etc.

In addition to these synthetic resins, mixtures or copolymers thereof can be used.

In the heat transfer image-receiving material, particularly in the image-receiving layer, can be incorporated a high boiling organic solvent or heat solvent as a substance capable of receiving a heat migrating dye or a dye diffusion aid.

Specific examples of such a high boiling organic solvent and heat solvent include compounds as described in JP-A-62-174754, 62-245253, 61-209444, 61-200538, 62-8145, 62-9348, 62-30247, and 62-136646.

The image-receiving layer in the heat transfer image-receiving material may carry a substance capable of receiving a heat migrating dye in the form of dispersion in a water-soluble binder. As the water-soluble binder to be used in this arrangement there can be used any known water-soluble polymer. A water-soluble polymer containing a group which can undergo crosslinking reaction by a film hardener may be preferably used.

The image-receiving layer may consist of two or more layers. This layer structure is preferably arranged such that the layer closest to the support contains a synthetic resin having a low glass transition point or a high boiling organic solvent or heat solvent to enhance its dyeability with dyes while the outermost layer contains a synthetic resin having a higher glass transition point or a mimimum required amount of a high boiling organic solvent or heat solvent or no such solvents to inhibit failures such as surface stickiness, adhesion to other substances, re-transfer to other substances after transfer and blocking with the heat transfer dye providing material.

The total thickness of the image-receiving layer is preferably in the range of 0.5 to 50 μm, particularly 3 to 30 μm. In the case of two-layer structure, the thickness of the outermost layer is preferably in the range of 0.1 to 2 μm, particularly 0.2 to 1 μm.

The image-receiving layer may optionally contain a dye fixing agent. As the dye fixing agent there can be used a mordant as described in JP-A-3-83685 or compound as described in JP-A-1-188391.

Desirable results can be obtained particularly when a dye of the present invention wherein X is —OH is used.

The heat transfer image-receiving material may comprise an interlayer interposed between the support and the image-receiving layer.

The interlayer serves as any one of or two or more of cushioning layer, porous layer and dye diffusion inhibiting layer by the materials constituting the interlayer. In some cases, it also serves an adhesive.

The dye diffusion inhibiting layer serves to inhibit the diffusion of a heat migrating dye into the support. The binder constituting the diffusion inhibiting layer may be soluble in water or organic solvent. A water-soluble binder may be preferably used. As such a water-soluble binder there can be used the water-soluble binder as described as the binder for the image-receiving layer, particularly gelatin.

The porous layer serves to inhibit the diffusion of heat applied upon heat transfer from the image-receiving layer to the support so that the heat can be effectively utilized.

The image-receiving layer, cushioning layer, porous layer, diffusion inhibiting layer, adhesion layer and other layers constituting the heat transfer image-receiving material may contain finely divided powder of silica, clay, talc, diatomaceous earth, calcium carbonate, calcium sulfate, barium sulfate, aluminum silicate, synthetic zeolite, zinc oxide, lithopone, titanium oxide, alumina or the like.

As the support for the heat transfer image-receiving material there can be used any material which can withstand the transferring temperature and satisfy the requirements such as smoothness, whiteness, sliperiness, friction properties, antistatic properties and depression after transfer. Examples of such a material include paper support such as synthetic paper (e.g., polyolefin paper, polystyrene paper), wood-free paper, art paper, coated paper, cast coat paper, wall paper, backing paper, synthetic resin or emulsion-impregnated paper, synthetic rubber latex-impregnated paper, synthetic resin-containing paper, cardboard, cellulose fiber paper and polyolefin-coated paper (particularly polyethylene double-coated paper), film or sheet of various plastics such as polyolefin, polyvinyl chloride, polyethylene terephthalate, polystyrene methacrylate and polycarbonate, film or sheet obtained by rendering these plastics white reflective, and laminate of a combination thereof.

The heat transfer image-receiving material may comprise a fluorescent brightening agent. Examples of such a fluorescent brightening agent include compounds as disclosed in K. Veenkataraman, *The Chemistry of Synthetic Dyes*, vol. V, Chapter 8, and JP-A-61-143752. Specific examples of such compounds include stilbene compounds, coumarin compounds, biphenyl compounds, benzoxazolyl compounds, naphthalimide compounds, pyrazoline compounds, carbostyryl compounds, and 2,5-dibenzoxazole thiophene compounds.

The fluorescent brightening agent can be used in combination with a discoloration inhibitor.

In the present invention, in order to improve the release of the heat transfer dye providing material from the heat transfer image-receiving material, the layers constituting the dye providing material and/or image-receiving material, particularly the outermost layer in contact with both the materials may preferably contain a release agent.

As such a release agent there can be used any known release agent such as solid or wax substance (e.g., polyethylene wax, amide wax, Teflon powder), surface active agent (e.g., fluorine surface active agent, phosphoric ester) and oil (e.g., paraffin, silicone, fluorine). Particularly preferred among these release agents is silicone oil.

As such a silicone oil there can be used unmodified silicone oil as well as modified silicone oil such as carboxy-modified, amino-modified and epoxy-modified silicone oils. Examples of such modified silicone oils include various modified silicone oils as described in *Modified Silicone Oil*, Shin-Etsu Silicone Co., Ltd., pp. 6–18B. If incorporated in an organic solvent-based binder, an amino-modified silicone oil containing a group capable of reacting a crosslinking agent in the binder (e.g., group capable of reacting with isocyanate) can be effectively used. If used in the form of emulsion dispersion in a water-soluble binder, a carboxy-modified silicone oil (e.g., X-22-3710 produced by Shin-Etsu Silicone Co., Ltd.) can be effectively used.

The layers constituting the heat transfer dye providing material and heat transfer image-receiving material to be used in the present invention may have been cured by a film hardener.

If an organic solvent-based polymer is cured, a film hardener as described in JP-A-61-199997 and JP-A-58-215398 can be used. For polyester resins, the use of an isocyanate-based film hardener is particularly preferred.

In order to cure a water-soluble polymer, there may be preferably used film hardeners as described in U.S. Pat. No. 4,678,739, 41st column, JP-A-59-116655, JP-A-62-245261, and JP-A-61-18942. Specific examples of such film hardeners include aldehyde-based film hardeners (e.g., formaldehyde), aziridine-based film hardeners, epoxy-based film hardeners (e.g., compound represented by the following formula),

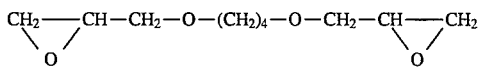

vinylsulfone-based film hardeners (e.g., N,N'-ethylenebis(vinylsulfonylacetamido)ethane), N-methylol-based film hardeners (e.g., dimethylolurea), and high-molecular weight film hardeners (e.g., compounds as described in JP-A-62-234157).

The heat transfer dye providing material and heat transfer image-receiving material may comprise a discoloration inhibitor. Examples of such a discoloration inhibitor include antioxidants, ultraviolet absorbents, and certain kinds of metal complexes.

Examples of such antioxidants include chroman compounds, coumaran compounds, phenol compounds (e.g., hindered phenols), hydroquinone derivatives, hindered amine derivatives, and spiroindane compounds. Further, compounds as described in JP-A-61-159644 can be effectively used.

Examples of the ultraviolet absorbents include benzotriazole compounds (as described in U.S. Pat. No. 3,533,794), 4-thiazolidone compounds (as described in U.S. Pat. No. 3,352,681), benzophenone compounds (as described in JP-A-56-2784), and compounds as described in JP-A-54-48535, JP-A-62-136641, and JP-A-61-88256. Further, ultraviolet-absorbing polymers as described in JP-A-62-260152 can be effectively used.

Examples of the metal complexes include compounds as described in U.S. Pat. Nos. 4,241,155, 4,245,018 (3rd to 36th columns), and 4,254,195 (3rd to 8th columns), and JP-A-62-174741, JP-A-61-88256 (pp. 27–29), JP-A-1-75568, and JP-A-63-199248.

Useful examples of discoloration inhibitors are described in JP-A-62-215272 (pp. 125–137).

The discoloration inhibitor for inhibiting the discoloration of a dye which has been transferred to the image-receiving material may have previously been incorporated in the image-receiving material or may be supplied externally, e.g., may be transferred from the dye providing material.

These antioxidants, ultraviolet light absorbents and metal complexes can be used in combination.

The layers constituting the heat transfer dye providing material and heat transfer image-receiving material may comprise various surface active agents for the purpose of facilitating coating, improving release properties and slipperiness, inhibiting electrification, accelerating development or like purposes.

Examples of surface active agents which can be used in the present invention include nonionic surface active agents such as saponin (steroid series), alkylene oxide derivatives (e.g., polyethylene glycol, polyethylene glycol alkyl ether, polyethylene glycol alkylaryl ether, polyethylene glycol ester, polyethylene glycol sorbitan ester, polyalkylene glcyol alkylamine, polyalkylene glycol alkylamide, polyethylene oxide adduct of silicone), glycidol derivatives (e.g., alkenylsuccinic polyglyceride, alkylphenol polyglyceride), aliphatic esters of polyhydric alcohol and alkyl esters of saccharide, anionic surface active agents containing acidic groups such as carboxyl group, sulfo group, phospho group, sulfuric ester group and phosphoric ester group (e.g., alkylcarboxylates, alkyl sulfonates, alkyl naphthalenesulfonates, alkyl sulfates, alkyl phosphates, N-acyl-N-alkyltaurines, sulfosuccinic esters, sulfoalkylpolyethylene alkylphenyl ethers, polyoxyethylene alkyl phosphates), amphoteric surface active agents such as amino acids, aminoalkylsulfonic acids, aminoalkylsulfuric esters, aminoalkylphosphoric esters, alkylbetaines and amine oxides, and cationic surface active agents such as alkylamine salts, aliphatic quaternary ammonium salts, aromatic quaternary ammonium salts, heterocyclic quaternary ammonium salts (e.g., pyridinium, imidazolium) and phosphonium or sulfonium salts containing aliphatic or heterocyclic groups. Specific examples of these surface active agents are given in JP-A-62-173463 and JP-A-62-183457.

When the substance capable of receiving a heat migrating dye, the release agent, the discoloration inhibitor, the ultraviolet light absorbent, the fluorescent brightening agent and other hydrophobic compounds are dispersed in a water-soluble binder, a surface active agent may be preferably used as a dispersing agent. For this purpose, there can be preferably used the above mentioned surface active agent. In addition, surface active agents as described in JP-A-59-157636, pp. 37–38, are particularly preferred.

The layers constituting the heat transfer dye providing material and heat transfer image-receiving material may comprise an organic fluoro compound for the purpose of improving slipperiness and release properties, inhibiting electrification or like purposes. Typical examples of such an organic fluoro compound include fluorine surface active agents as described in JP-B-57-9053 (8th–17th columns), JP-A-61-20944, and JP-A-62-135826, and hydrophobic fluorine compounds such as oily fluorine compound (e.g., fluorine oil) and solid fluorine compound resin (e.g., tetrafluoroethylene resin).

The heat transfer dye providing material and heat transfer image-receiving material may comprise a matting agent. Examples of such a matting agent include compounds as described in JP-A-61-88256, page 29, such as silicon dioxide, polyolefin and polymethacrylate. Other examples of such a matting agent include compounds as described in JP-A-63-274944 and JP-A-63-274952, such as benzoguanamine resin beads, polycarbonate resin beads and AS resin beads.

EXAMPLE 1

The dyes of the present invention were examined for fastness to light in a solution system. The dyes thus examined and the test results are set forth in Table 1.

Condition: merry-go-round type xenon radiator (produced by Dojun Koki K.K.; output: 500 W, 100,000 lux)

Cell: quartz cell

Solvent: acetonitrile

Concentration: $3.0 \times 10^{-5}$ (mol/l)

Percent residue: represented by the change (%) in the concentration at $\lambda$max from before to after forced discoloration test

TABLE 1

| Dye | Irradiation Time | Ultraviolet Light Filter | Percent Residue | Remarks |
|---|---|---|---|---|
| I-2 | 60 min. | None | 50 | Invention |
| I-4 | " | " | 59 | " |
| I-7 | " | " | 54 | " |
| I-10 | " | " | 62 | " |
| c | " | " | 43 | Comparison |

Comparative Dye c:

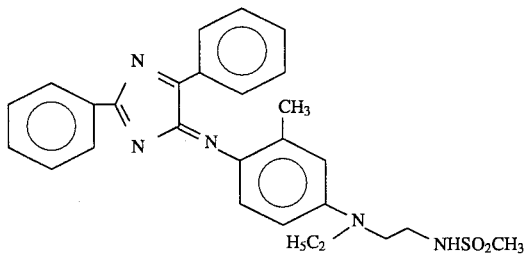

EXAMPLE 2

The dyes of the present invention were examined for fastness to light in a solution system. The dyes thus examined and the test results are set forth in Table 2.

Condition: merry-go-round type xenon radiator (produced by Dojun Koki K.K.; output: 500 W, 100,000 lux)

Cell: quartz cell

Solvent: acetonitrile

Density: $4.0 \times 10^{-5}$ (mol/l)

Percent residue: represented by the change (%) in the density at $\mu$max from before to after forced discoloration test

TABLE 2

| Dye | Irradiation Time | Ultraviolet Light Filter | Percent Residue | Remarks |
|---|---|---|---|---|
| II-2 | 10 min. | None | 61 | Invention |
| II-4 | " | " | 69 | " |
| II-10 | " | " | 67 | " |
| II-17 | " | " | 67 | " |
| II-24 | " | " | 80 | " |
| b | " | " | 80 | Comparison |

EXAMPLE 3

In order to demonstrate the usefulness of the dyes of the present invention as filter dyes, the following model filters were prepared and examined for fastness to light.

Onto a 100-μm thick polyethylene terephthalate film (produced by Teijin Limited) which had been rendered heat resistant and smoothened on its back side as a support was coated a dye dispersion layer coating composition having the following formulations by a wire bar coating process to prepare a model filter. The thickness of the coating was adjusted such that the density after drying reached 2.0.

| Dye dispersion layer coating composition: | |
|---|---|
| Dye (I-1) | 1.0 g |
| Polyvinyl butyral resin (Denka Butyral 5000-A produced by Denki Kagaku Kogyo K.K.) | 3.0 g |
| Toluene | 50 cc |
| Methyl ethyl ketone | 50 cc |
| Polyisocyanate (Takenate D110N produced by Takeda Chemical Industries, Ltd.) | 0.2 cc |

Model filters were prepared in the same manner as above except that Dye (I-1) was replaced by other dyes set forth in Table 3.

The model filters thus prepared were irradiated with light from a 17,000 lux fluorescent lamp for 14 days to examine the stability of the dyes. For evaluation of the dye stability, the ratio of the density measured before to after irradiation was determined. The results are set forth in Table 3.

TABLE 3

| Dye | Percent REsidue | Remarks |
|---|---|---|
| I-1 | 95 | Invention |
| I-2 | 93 | " |
| I-4 | 94 | " |
| I-7 | 94 | " |
| I-10 | 95 | " |
| II-2 | 97 | " |
| II-4 | 98 | " |
| II-10 | 98 | " |
| II-17 | 97 | " |
| II-24 | 98 | " |

TABLE 3-continued

| Dye | Percent REsidue | Remarks |
| --- | --- | --- |
| b | 89 | Comparison |
| c | 85 | " |

The results set forth above show that the dyes of the present invention exhibit a remarkable fastness to light as compared with the comparative dyes.

EXAMPLE 4

Onto a commercially available uncoated base paper (basis weight: 64 g/m$^2$) was coated a coating solution consisting of 43 parts (by weight calculated in terms of solid content, hereinafter the same) of finely divided hollow grains of a styrene-acrylic ester copolymer (grain diameter: 0.3 to 0.4 μm), 17 parts of vapor phase process anhydrous silica (grain diameter: 12 nm), 12 parts of a styrene-butadiene copolymer latex, 18 parts of a polyvinyl acetate latex and 10 parts of finely divided grains of polymethyl methacrylate (grain diameter: about 8 μm) by means of a wire bar in such an amount that the solids content reached 10 g/m$^2$ to prepare a paper for ink jet recording.

Ink jet recording was made on this recording paper with Ink A having the following formulations. In this ink jet recording, an electrostatic acceleration type ink jet apparatus equipped with a head having a nozzle pore diameter of 50 μm and a dot density of 8/mm was used.

| Ink A: | |
| --- | --- |
| Dye (I-1) of the present invention | 6 g |
| Diethyl phthalate | 30 g |
| Diisopropyl adipate | 44 g |
| N,N-Diethyldodecanamide | 20 g |

This ink exhibited an excellent dischargeability, and a sharp and high density cyan image was obtained.

Similar ink jet recording tests were effected except that Dye (I-1) was replaced by Dyes (I-7), (I-10), (II-4), (II-10) and (II-24), respectively, in the same gram equivalent. As a result, all these dyes exhibited an excellent ink dischargeability and thus provided sharp and high density cyan images.

After these images were allowed to stand under indoor light for 3 months, the density thereof showed a drop of 1% or less.

EXAMPLE 5

Preparation of Heat Transfer Material

The following materials were sufficiently dispersed in admixture to prepare a coating solution for smooth heat-resistant protective layer.

| Methyl methacrylate | 10 g |
| --- | --- |
| n-Butyl acrylate | 2 g |
| Benzoyl peroxide | 0.1 g |
| Silica | 35 g |
| Isopropyl alcohol (IPA) | 15 g |

The coating solution was diluted with a proper amount of a mixture of toluene and IPA. The coating solution was then coated on a 6-μm thick polyethylene terepthalate film (hereinafter referred to as "PET") as a substrate by means of a wire bar. The coated material was then dried at a temperature of 100° C. for 1 minute to form a smooth heat-resistant protective layer with a thickness of about 1.5 μm.

A hot-melt ink having the following formulations was prepared.

| Formulations of hot-melt ink: | |
| --- | --- |
| Dye (I-1) | 10 g |
| Barium salt of lanolin fatty acid | 30 g |
| Carnauba wax | 20 g |
| Paraffin wax | 20 g |
| Dispersant | 0.5 g |
| Liquid paraffin | 5 g |

The ink having the above mentioned formulations was then sufficiently dispersed with a mixture of 100 cc of methyl ethyl ketone and 130 cc of toluene at a temperature of 68° C. by a ball mill for about 48 hours.

To the ink dispersion was added 300 g of a 20 wt. % vinyl chloride-vinyl acetate copolymer resin solution (10 parts of resin, 20 parts of toluene, 20 parts of methyl ethyl ketone). The mixture was then dispersed by a ball mill for about 1 hour to prepare a coating solution of heat-sensitive transfer composition.

This coating solution was coated on the surface of the above mentioned PET film opposite the smooth heat-resistant protective layer by means of a wire bar, and then dried at a temperature of 100° C. for 1 minute to form a hot-melt ink layer having a thickness of about 5 μm.

The heat transfer material thus obtained was laminated with a plain paper as a heat transfer image-receiving material in such an arrangement that the transfer layer (hot-melt ink layer) in the heat transfer material was brought into contact with the plain paper. Printing was effected by a heat head on the heat transfer material from the support side to cause transfer. As a result, a sharp cyan color recording was provided.

Heat transfer materials were prepared in the same manner as above except that Dye (I-1) was replaced by Dyes (I-7), (I-10), (II-4), (II-10) and (II-24), respectively, in the same gram equivalent weight. Using these heat transfer materials, transfer was similarly effected. As a result, a sharp cyan color recording was provided.

These recorded sheets were then examined for stability of image to light. A high image stability to light was obtained.

EXAMPLE 6

Preparation of Heat Transfer Dye Providing Material (6-1)

Onto a 6-μm thick polyethylene terephthalate film (produced by Teijin Limited) which had been rendered heat resistant and smoothened on its back side as a support was coated a heat transfer dye providing layer coating composition having the following formulations by a wire bar coating process in such an amount that the dry thickness thereof reached 1.5 μm to prepare a heat transfer dye providing material (6-1).

| Heat transfer dye providing layer coating composition: | |
|---|---|
| Dye (I-42) | 10 mmol |
| Polyvinyl butyral resin (Denka Butyral 5000-A produced by Denka Kagaku Kogyo K.K.) | 3 g |
| Toluene | 40 cc |
| Methyl ethyl ketone | 40 cc |
| Polyisocyanate (Takenate D110N produced by Takeda Chemical Industries, Ltd.) | 0.2 cc |

The present and comparative heat transfer dye providing materials (6-2) to (6-6) were prepared in the same manner as above except that Dye (I-42) was replaced by other dyes set forth in Table 4.

Preparation of Heat Transfer Image-Receiving Material

Onto a 150-μm thick synthetic paper (YUPO-FPG-150 produced by Oji Yuka Goseishi Co., Ltd.) as a support was coated an image-receiving layer coating composition having the following formulations by a wire bar coating process to a dry thickness of 8 μm to form a heat transfer image-receiving material. Drying was tentatively effected by means of a dryer, and then completed at a temperature of 100° C. in an oven for 30 minutes.

| Image-receiving layer coating composition: | |
|---|---|
| Polyester resin (Vylon 280 produced by Toyobo Co., Ltd.) | 22 g |
| Polyisocyanate (KP-90 produced by Dainippon Ink and Chemicals, Inc.) | 4 g |
| Amino-modified silicone oil (KF-857 produced by Shin-Etsu Silicone Co., Ltd.) | 0.5 g |
| Methyl ethyl ketone | 85 cc |
| Toluene | 85 cc |
| Cyclohexanone | 15 cc |

The heat transfer dye providing materials (6-1) to (6-6) thus prepared were each laminated with the heat transfer image-receiving material thus obtained in such an arrangement that the heat transfer dye providing layer was brought into contact with the image-receiving layer. Printing was effected on these heat transfer dye providing materials from the support side by means of a heat head under the conditions of heat head output of 0.25 W/dot, pulse width of 0.15 to 15 msec., and dot density of 6/mm. Thus, the image-receiving layer on the image-receiving material was imagwise dyed with a cyan dye. As a result, a sharp image recording was provided free of uneven transfer.

These heat transfer image-receiving materials on which recording had been made were then irradiated with light from a 17,000 lux fluorescent lamp for 7 days to examine the dye stability. For evaluation of the dye stability, percent residue was determined by calculating the percentage of the change in Status A reflection density from before to after irradiation (Before irradiation, a portion at which Status A reflection density is 1.0 is selected. After irradiation, the same portion is measured). The results are set forth in Table 4.

TABLE 4

| Heat transfer dye providing material No. | Dye | Maximum density | Light fastness (percent residue) | Remarks |
|---|---|---|---|---|
| 6-1 | I-42 | 1.5 | 89 | Invention |
| 6-2 | I-46 | 1.9 | 90 | " |
| 6-3 | II-25 | 2.0 | 92 | " |
| 6-4 | II-27 | 1.8 | 94 | " |
| 6-5 | III-31 | 1.9 | 89 | " |
| 6-6 | d | 2.0 | 87 | Comparison |

Comparative dye d:

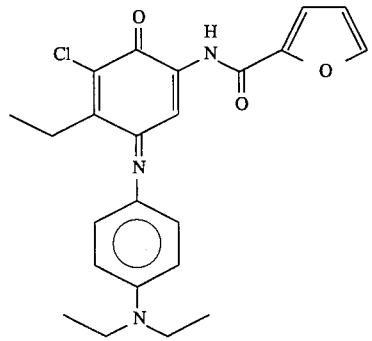

(disclosed in JP-A-2-98492)

The above mentioned results show that the dye images derived from the dyes of the present invention exhibit a high fastness to light as compared with the dye image derived from the known azomethine dye d.

EXAMPLE 7

Heat transfer dye providing materials (7-1) to (7-7) were prepared in the same manner as in Example 6 except that Dye (I-42) to be incorporated in the heat transfer dye providing layer coating composition was replaced by other dyes set forth in Table 5, respectively.

Using the same image-receiving material as prepared in Example 6, printing was made on these heat transfer dye providing materials. All these heat transfer dye providing materials provided a sharp and high density image recording free of uneven transfer. Further, the images thus obtained exhibited an excellent fastness to light.

TABLE 5

| Heat transfer dye providing material No. | Dye |
|---|---|
| 7-1 | I-43 |
| 7-2 | I-44 |
| 7-3 | I-45 |
| 7-4 | II-28 |
| 7-5 | III-32 |
| 7-6 | IV-21 |
| 7-7 | IV-22 |

EXAMPLE 8

Heat transfer dye providing materials (8-1) and (8-2) were prepared in the same manner as in Example 6 except that the polyvinyl butyral resin and dye to be incorporated in the heat transfer dye providing layer coating composition were replaced by the resins and dyes set forth in Table 6, respectively.

Using the same image-receiving material as used in Example 6, printing was made on these heat transfer dye providing materials. As a result, a sharp image recording was provided free of uneven transfer as shown in Table 6. Further, the images thus obtained exhibited an excellent fastness to light.

TABLE 6

| Heat transfer dye providing material | Resin | Dye | Fastness to light (percent residue) |
|---|---|---|---|
| 8-1 | Ethyl cellulose | I-46 | 89 |
| 8-2 | Cellulose acetobutyrate | II-25 | 92 |

Examples 9 to 13 will be described hereinafter with reference to the combination of other heat transfer image-receiving materials with the above mentioned heat transfer dye providing materials of the present invention.

EXAMPLE 9

Preparation of Heat Transfer Image-Receiving Material

Onto a 150-μm thick synthetic paper (YUPO-FPG-150 produced by Oji Yuka Goseishi Co., Ltd.) as a support was coated an image-receiving layer coating composition having the following formulations by a wire bar coating process to a dry thickness of 10 μm to form a heat transfer image-receiving material. Drying was tentatively effected by means of a dryer, and then completed at a temperature of 100° C. in an oven for 30 minutes.

| Image-receiving layer coating composition: | |
|---|---|
| Polyester resin No. 1 (compound having the following structural formula) | 2.0 g |
| Epoxy-modified silicone oil (KF-100T produced by Shin-Etsu Silicone Co., Ltd.) | 0.5 g |
| Methyl ethyl ketone | 85 cc |
| Toluene | 85 cc |
| Cyclohexanone | 30 cc |

Polyester Resin No. 1

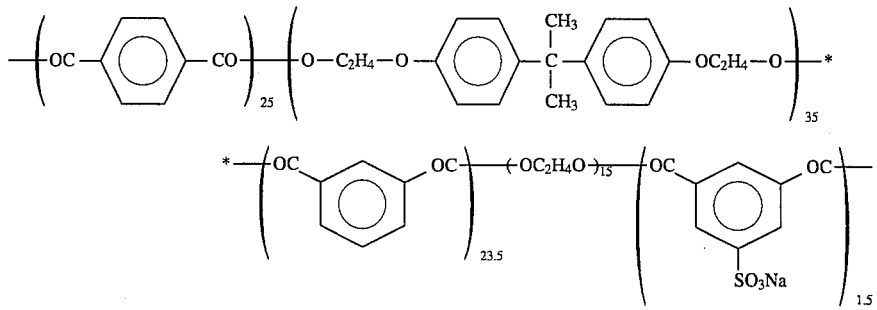

This heat transfer image-receiving material was combined with the heat transfer dye providing materials comprising the dyes of the present invention prepared in Examples 6 and 7. Printing was made on these recording materials. As a result, a sharp image recording was provided. The images thus obtained exhibited an excellent fastness to light.

EXAMPLE 10

Preparation of Heat Transfer Image-Receiving Material

A 200-μm thick paper was laminated with polyethylene to a thickness of 15 Bm on one side and to a thickness of 25 Bm on the other side to prepare a resin coated paper. An image-receiving layer coating composition having the following formulations was coated on the 15-μm thick polyethylene-laminated side of the resin coated paper to a dry thickness of 10 μm, and then dried to prepare a heat transfer image-receiving material.

| Image-receiving layer coating composition: | |
|---|---|
| Polyester resin No. 1 (compound having the structural formula set forth above) | 25 g |
| Amino-modified silicone oil (KF-857 produced by Shin-Etsu Silicone Co., Ltd.) | 0.8 g |
| Polyisocyanate (KP-90 produced by Dainippon Ink and Chemicals, Inc.) | 4 g |
| Methyl ethyl ketone | 100 cc |
| Toluene | 100 cc |

Printing was made in the same manner as in Example 6. As a result, a sharp and high density image recording was provided. The image thus obtained exhibited an excellent fastness to light.

EXAMPLE 11

Preparation of Heat Transfer Image-Receiving Material

A solution of a dye-receiving polymer in an organic solvent having the following formulations (B') was emulsion-dispersed in an aqueous solution of gelatin having the following formulations (A') by means of a homogenizer to prepare a gelatin dispersion of a dye-receiving substance.

| (A') Aqueous solution of gelatin: | |
|---|---|
| Gelatin | 2.3 g |
| 5% Aqueous solution of sodium dodecylbenzenesulfonate | 20 cc |
| Water | 80 cc |

-continued

| (B') Solution of dye-receiving polymer: | |

| Polyester resin (Vylon 300 produced by Toyobo Co., Ltd.) | 7.0 g |
| Carboxy-modified silicone oil (X-22-3710 produced by Shin-Etsu Silicone Oil Co., Ltd.) | 0.7 g |
| Methyl ethyl ketone | 20 cc |
| Toluene | 10 cc |
| Triphenyl phosphate | 1.5 g |

To the dispersion thus obtained was added a solution of 0.5 g of a fluorine-based surface active agent (a) in 10 cc of a 1:1 mixture of water and methanol to obtain an image-receiving layer coating composition.

Fluorine-based surface active agent (a):

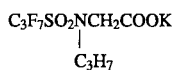

This coating solution was coated on a 150-μm thick corona-discharged synthetic paper (YUPO-SGG-150 produced by Oji Yuka Goseishi Co., Ltd.) by a wire bar coating process to a wet thickness of 75 μm, and then dried to obtain a heat transfer image-receiving material.

Using the heat transfer dye providing materials comprising the dyes prepared in Examples 6 and 7 and the heat transfer image-receiving material thus obtained, image recording was effected in the same manner as in Example 6.

The image thus obtained exhibited a high density, sharpness and fastness to light.

EXAMPLE 12

Preparation of Heat Transfer Image-Receiving Material

Using the following image-receiving layer coating composition, a heat transfer image-receiving material was prepared in the same manner as in Example 6.

Image-receiving layer coating composition

An image-receiving layer coating composition was prepared in the same manner as in Example 6 except that 7 g of an ultraviolet light absorbent having the following structural formula was further added to the system.

Ultraviolet light absorbent:

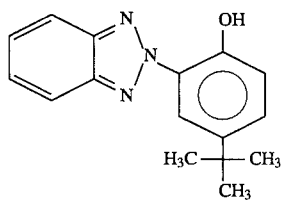

Using the heat transfer dye providing materials comprising the dyes prepared in Examples 6 and 7 and the heat transfer image-receiving material thus obtained, image recording was effected in the same manner as in Example 6. As a result, a sharp and high density image was obtained. The image thus obtained exhibited a higher fastness to light than obtained with the image-receiving material of Example 6.

EXAMPLE 13

Heat transfer dye providing materials (13-1) to (13-5) were prepared in the same manner as in Example 6 except that Dye (I-42) (10 mmol) to be incorporated in the heat transfer dye providing layer coating composition was replaced by two other kinds of dyes (5 mmol each) set forth in Table 7, respectively. Heat transfer dye providing materials (13-6) and (13-7) were prepared in the same manner as in Example 6 except that Dye (I-42) (10 mmol) to be incorporated in the heat transfer dye providing layer coating composition was replaced by another kind of dye (10 mmol) set forth in Table 7.

In order to examine the storage stability of these heat transfer dye providing materials at an elevated temperature, these specimens were dry stored at a temperature of 50° C. in an oven for 1 week.

The evaluation criterion is as follows:

E: No dye agglomeration or crystallization observed under microscope

F: Slight agglomeration or crystallization observed under microscope

P: Dye agglomeration or crystallization visually observed all over the surface

The results are set forth in Table 7.

TABLE 7

| No. | Dye providing material | Dye | Storage stability | Remarks |
| --- | --- | --- | --- | --- |
| 1 | 13-1 | (I-42) + (I-44) | E | Invention |
| 2 | 13-2 | (I-42) + (I-46) | E | " |
| 3 | 13-3 | (I-42) + (II-25) | E | " |
| 4 | 13-4 | (II-25) + (II-27) | E | " |
| 5 | 13-5 | (I-44) + (II-25) | E | " |
| 6 | 13-6 | (I-46) | F | " |
| 7 | 13-7 | d | P | Comparison |

The comparison of No. 6 and No. 7 and Nos. 1 to 5 show that the dyes of the present invention provide the heat transfer dye providing materials with a better storage stability when used in admixture than when used singly.

Using the heat transfer image-receiving material as used in Example 6 and the heat transfer dye providing materials (13-1) to (13-7) which had been subjected to heat stability test, printing was effected in the same manner as in Example 6. As a result, all the heat transfer dye providing materials (13-1) to (13-6) of the present invention provided a sharp image recording free of uneven transfer while the comparative heat transfer dye providing material (13-7) provided an uneven image.

The derivatives represented by formula (V) of the present invention are useful as synthesis intermediates of physiologically active substances such as pharmaceutical preparations and pesticides. These derivatives are also useful as couplers in the field of photographic chemistry.

On the other hand, the compounds represented by formulae (I) to (IV) are useful dyes which are advantageous in that they exhibit a reduced secondary absorption and a primary absorption wavelength of 600 nm or more.

When used as an image forming dye in ink jet recording process, heat-sensitive transfer recording process, etc., the novel pyrrolotriazole azomethine dye of the present invention provides a high density image free of discoloration because of its remarkably excellent fastness to light.

Also, when used as various filter dyes, the azomethine dye of the present invention provides a filter with an excellent stability and a remarkably reduced density drop because of its excellent fastness to light.

Furthermore, when image formation is effected on a heat transfer dye providing material comprising the pyrrolotriazole azomethine dye of the present invention, it provides an image with a high fastness to heat and light and an excellent color reproducibility.

Moreover, the pyrrolotriazole azomethine dye of the present invention provides the heat transfer dye providing material with a better storage stability when used in admixture with one or more present azomethine dyes than when used singly.

While the invention has been described in detail and with reference to specific embodiments thereof, it will be apparent to one skilled in the art that various changes and modifications can be made therein without departing from the spirit and scope thereof.

What is claimed is:

1. A pyrrolotriazole azomethine dye represented by any one of formulae (I) or (II):

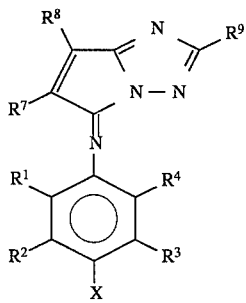

(I)

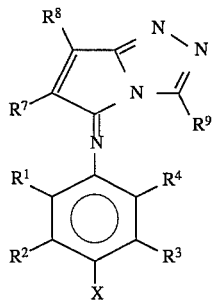

(II)

wherein:

$R^1$, $R^2$, $R^3$ and $R^4$ each independently represents hydrogen, halogen, alkyl, aryl, a heterocyclic substituent, cyano, hydroxyl, nitro, carboxyl, a sulfonic acid substituent, amino, alkoxy, aryloxy, acylamino aminocarbonylamino, sulfamoylamino, alkylthio, arylthio, alkoxycarbonylamino, sulfonylamino, carbamoyl, sulfamoyl, sulfonyl, alkoxycarbonyl, heterocyclic oxy, azo, acyloxy, carbamoyloxy, silyloxy, aryloxycarbonyl, imido, heterocyclic thio, sulfinyl, phosphoryl, formyl, acyl, or azolyl;

X represents —OH or —NR$^5$R$^6$;

$R^5$ and $R^6$ each independently represents hydrogen, alkyl, aryl, or a heterocyclic substituent;

$R^7$ represents an electrophilic group having a Hammett's substituent constant $\sigma_p$ of 0.15 or more;

$R^8$ and $R^9$ each independently represents hydrogen, aryl, a heterocyclic substituent, alkyl, cyano, carboxyl, formyl, acyl, carbamoyl, alkoxycarbonyl aryloxycarbonyl, acylamino alkoxycarbonylamino, aryloxycarbonylamino, sulfonylamino, aminocarbonylamino, sulfamoylamino, amino, alkoxy, aryloxy, silyloxy, heteryloxy, alkylthio, arylthio, heterylthio, halogen, hydroxyl, nitro, sulfamoyl, sulfonyl, azo, acyloxy, carbamoyloxy.

2. A heat transfer dye providing material comprising a support having thereon a dye providing layer containing a heat migrating dye, said dye providing layer containing at least one pyrrolotriazole azomethine dye represented by any one of formulae (I) or (II):

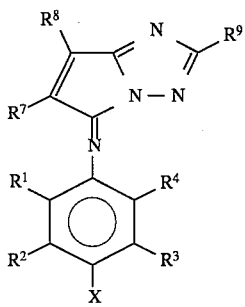

(I)

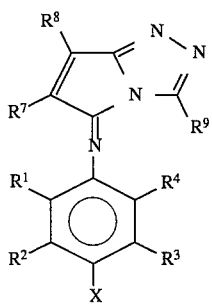

(II)

wherein:

$R^1$, $R^2$, $R^3$ and $R^4$ each independently represents hydrogen, halogen, alkyl, aryl, a heterocyclic substituent, cyano, hydroxyl, nitro, carboxyl, a sulfonic acid substituent, amino, alkoxy, aryloxy, acylamino, aminocarbonylamino, sulfamoylamino, alkylthio, arylthio, alkoxycarbonylamino, sulfonylamino, carbamoyl, sulfamoyl, sulfonyl, alkoxycarbonyl, heterocyclic oxy, azo, acyloxy, carbamoyloxy, silyloxy, aryloxycarbonyl, imido, heterocyclic thio, sulfinyl, phosphoryl, formyl, acyl, or azolyl;

X represents —OH or —NR$^5$R$^6$;

$R^5$ and $R^6$ each independently represents hydrogen, alkyl, aryl, or a heterocyclic substituent;

$R^7$ represents an electrophilic group having a Hammett's substituent constant op of 0.15 or more;

$R^8$ and $R^9$ each independently represents hydrogen, aryl, a heterocyclic substituent, alkyl, cyano, carboxyl, formyl, acyl, carbamoyl, alkoxycarbonyl, aryloxycarbonyl, acylamino, alkoxycarbonylamino, aryloxycarbonylamino, sulfonylamino, aminocarbonylamino, sulfamoylamino, amino, alkoxy, aryloxy, silyloxy, heteryloxy alkylthio, arylthio, heterylthio, halogen, hydroxyl, nitro, sulfamoyl, sulfonyl, azo, acyloxy, carbamoyloxy, imido, sulfinyl, phosphoryl or azolyl;

the sum of Hammett's substituent constant $\sigma_p$ of $R^7$ and $R^8$ is 0.65 or more;

$R^1$ and $R^2$, $R^2$ and $R^5$, $R^5$ and $R^6$, $R^6$ and $R^3$, and $R^3$ and $R^4$ each are pairs of substituents selected from the group consisting of substituents which are independent from each other and substituents which are combined with each other to complete a ring;

$R^7$ and $R^{87}$ are a pair of substituents selected from the group consisting of substituents which are independent from each other and substituents which are combined with each other to complete a ring; and Z represents hydrogen, halogen, arylthio, heterocyclic thio, arylsulfinyl, or nitroso.

3. A heat transfer dye providing material as in claim 2, wherein said pyrrolotriazole azomethine dye is a pyrrolotriazole azomethine dye represented by formula (I).

4. A heat transfer dye providing material as in claim 2, wherein $R^2$, $R^3$ and $R^4$ each represents hydrogen; and $R^1$ represents hydrogen, alkyl, or acylamino.

5. A heat transfer dye providing material as in claim 2, wherein said electrophilic group having a Hammett's substituent constant $\sigma_p$ of 0.15 or more for $R^7$ is formyl, acyl, acyloxy group, carbamoyl, alkoxycarbonyl, aryloxycarbonyl, cyano, carboxyl, nitro group, dialkylphosphono, diarylphosphono, diarylphosphinyl, alkylsulfinyl, arylsulfinyl, alkylsulfonyl, arylsulfonyl, arylthio, sulfonyloxy, acylthio, sulfamoy, isocyanato, thiocyanato, thiocarbonyl, alkyl substituted by at least two halogen atoms, alkoxy group substituted by at least two halogen atoms, aryloxy substituted by at least two halogen atoms, alkylamino substituted by at least two halogen atoms, alkylthio substituted by at least two halogen atoms, aryl substituted by other electrophilic groups having a Hammett's substituent constant $\sigma_p$ of 0.15 or more, a heterocyclic substituent, chlorine, bromine, or selenocyanato.

6. A pyrrolotriazole azomethine dye as in claim 1, wherein $R^9$ is unsubstituted aryl of aryl substituted by at least one substituent selected from the group consisting of halogen, hydroxyl, carboxyl, sulfo, cyano, nitro, amino, alkyl, alkenyl, alkynyl, aryl, alkoxy, aryloxy, alkylthio, arylthio, alkylsulfonyl, arylsulfonyl, acyl, acyloxy, alkoxycarbonyl, aryloxycarbonyl, carbonamido, sulfonamido, carbamoyl, sulfamoyl, ureido, alkoxycarbonylamino, sulfamoylamino, alkoxysulfonyl, imido, and heterocyclic substituents.

7. A heat transfer dye providing material as in claim 2, wherein the at least one pyrrolotriazole azomethine dye is a cyan dye having a primary absorption wavelength of at least 600 nm.

8. A heat transfer dye providing material as in claim 2, wherein the at least one pyrrolotriazole azomethine dye is coated in an amount of from 0.03 to 1.0 g/m².

9. A heat transfer dye providing material as in claim 2, wherein the Hammett's substituent constant for $R^7$ is from 0.15 to 0.92, and the sum of the Hammett's substituent constant for $R^7$ and $R^8$ is from 0.65 to 1.32. imido, sulfinyl, phosphoryl, or azolyl;

the sum of Hammett's substituent constant $\sigma_p$ of $R^7$ and $R^8$ is 0.65 or more;

$R^1$ and $R^2$, $R^2$ and $R^5$, $R^5$ and $R^6$, $R^6$ and $R^3$, and $R^3$ and $R^4$ each pairs of substituents selected from the group consisting of substituents which are independent from each other and substituents which are combined with each other to complete a ring;

$R^7$ and $R^8$ are a pair of substituents selected from the group consisting of substituents which are independent from each other and substituents which are combined with each other to complete a ring; and Z represents hydrogen, halogen, arylthio, heterocyclic thio, arylsulfinyl, or nitroso.

* * * * *